US012745910B2

(12) United States Patent
Reuvenny et al.

(10) Patent No.: US 12,745,910 B2
(45) Date of Patent: Sep. 29, 2026

(54) INTRAORAL SCANNER

(71) Applicant: LUMINX IL LTD, Hod Hasharon (IL)

(72) Inventors: Amitai Reuvenny, Kfar-Saba (IL); Benny Pesach, Rosh Haayin (IL); Blanc Zach Lehr, Tel-Aviv (IL); Ygael Grad, Tel-Aviv (IL)

(73) Assignee: Luminx IL LTD, Hod Hasharon (IL)

(*) Notice: Subject to any disclaimer, the term of this patent is extended or adjusted under 35 U.S.C. 154(b) by 588 days.

(21) Appl. No.: 17/923,454

(22) PCT Filed: May 6, 2021

(86) PCT No.: PCT/IL2021/050523

§ 371 (c)(1),
(2) Date: Nov. 4, 2022

(87) PCT Pub. No.: WO2021/224929

PCT Pub. Date: Nov. 11, 2021

(65) Prior Publication Data

US 2023/0190109 A1 Jun. 22, 2023

Related U.S. Application Data

(60) Provisional application No. 63/020,602, filed on May 6, 2020.

(51) Int. Cl.
*A61B 5/00* (2006.01)
*G03B 15/14* (2021.01)
(Continued)

(52) U.S. Cl.
CPC .......... *A61B 5/0088* (2013.01); *A61B 5/0079* (2013.01); *A61B 5/4547* (2013.01);
(Continued)

(58) Field of Classification Search
None
See application file for complete search history.

(56) References Cited

U.S. PATENT DOCUMENTS 9,939,714 B1 4/2018 Matthews
11,598,632 B2 * 3/2023 Pesach ................ H04N 13/254
(Continued)

FOREIGN PATENT DOCUMENTS

CA 2816265 A1 * 11/2014 ......... A61B 1/00105
CH 714414 A2 * 6/2019 ............. A61C 19/04
(Continued)

OTHER PUBLICATIONS

International Preliminary Report on Patentability Dated Nov. 17, 2022 From the International Bureau of WIPO Re. Application No. PCT/IL2021/050523. (7 Pages).
(Continued)

*Primary Examiner* — Ricky Chin
(74) *Attorney, Agent, or Firm* — Fenwick & West LLP

(57) ABSTRACT

A dental add-on for an electronic communication device having a screen and an imager, the add-on including: a body comprising: a distal portion sized and shaped to be at least partially inserted into a human mouth within, in one or more dimension, one or both dental arches; and an optical path extending from an optical element of the electronic communication device, through the body to the distal portion and configured to adapt a FOV of the optical element for dental imaging; a connector for connection of the add-on body to the electronic communication device.

24 Claims, 28 Drawing Sheets

(51) Int. Cl.
*G03B 17/17* (2021.01)
*G03B 17/56* (2021.01)

(52) U.S. Cl.
CPC ............ *A61B 5/6898* (2013.01); *A61B 5/742* (2013.01); *G03B 17/565* (2013.01); *A61B 2560/0443* (2013.01); *G03B 15/14* (2013.01); *G03B 17/17* (2013.01)

(56) References Cited

U.S. PATENT DOCUMENTS

| | | | | |
|---|---|---|---|---|
| 12,268,367 | B2 * | 4/2025 | Pesach | A61B 5/1077 |
| 2001/0026315 | A1 | 10/2001 | Ooshima et al. | |
| 2006/0154198 | A1 | 7/2006 | Durbin et al. | |
| 2013/0209954 | A1 * | 8/2013 | Prakash | A61B 1/00172 433/29 |
| 2015/0065803 | A1 * | 3/2015 | Douglas | G06T 7/143 600/200 |
| 2015/0087926 | A1 * | 3/2015 | Raz | A61B 5/01 600/301 |
| 2015/0103317 | A1 * | 4/2015 | Goldfain | A61B 3/156 351/207 |
| 2016/0092711 | A1 * | 3/2016 | Powell | G06K 7/10831 235/462.06 |
| 2017/0042421 | A1 * | 2/2017 | Wallace | A61B 3/107 |
| 2018/0064326 | A1 | 3/2018 | Patrick et al. | |
| 2018/0078128 | A1 | 3/2018 | Adamson et al. | |
| 2018/0092534 | A1 * | 4/2018 | Nabhan | G16H 30/20 |
| 2018/0176349 | A1 * | 6/2018 | Aberle | G02B 13/001 |
| 2018/0284580 | A1 * | 10/2018 | Matthews | A61B 1/00042 |
| 2019/0000309 | A1 * | 1/2019 | Yamamoto | A61B 1/05 |
| 2019/0021656 | A1 | 1/2019 | Suri et al. | |
| 2019/0192262 | A1 | 6/2019 | Pesach | |
| 2019/0200903 | A1 | 7/2019 | Watson | |
| 2019/0223993 | A1 | 7/2019 | Mason et al. | |
| 2019/0254529 | A1 * | 8/2019 | Pesach | A61B 5/0064 |
| 2019/0269485 | A1 | 9/2019 | Elbaz et al. | |
| 2020/0005422 | A1 * | 1/2020 | Subramanian | G06N 3/0464 |
| 2020/0060550 | A1 * | 2/2020 | Pesach | G06T 7/11 |
| 2020/0214811 | A1 | 7/2020 | Verker et al. | |
| 2020/0359777 | A1 * | 11/2020 | Pesach | G06V 40/165 |
| 2020/0383559 | A1 * | 12/2020 | Lynn | A61B 1/04 |
| 2021/0060352 | A1 * | 3/2021 | Kim | G16H 40/67 |
| 2021/0361396 | A1 * | 11/2021 | Yancey | A61B 5/4547 |
| 2022/0115127 | A1 | 4/2022 | Hokmabadi | |
| 2023/0184707 | A1 * | 6/2023 | Alizadeh | C04B 40/0096 324/694 |
| 2023/0190109 | A1 * | 6/2023 | Reuvenny | A61B 5/4547 433/29 |
| 2024/0268935 | A1 * | 8/2024 | Pesach | A61B 5/0088 |
| 2025/0044079 | A1 * | 2/2025 | Pesach | A61B 1/045 |

FOREIGN PATENT DOCUMENTS

| | | | | | |
|---|---|---|---|---|---|
| CN | 204903874 | U | * | 12/2015 | |
| CN | 107951465 | A | * | 4/2018 | A61B 3/032 |
| CN | 207704106 | U | * | 8/2018 | |
| CN | 109270774 | A | * | 1/2019 | H04M 1/0272 |
| CN | 109964148 | A | * | 7/2019 | G01J 1/4228 |
| CN | 210158573 | U | | 3/2020 | |
| CN | 111344592 | A | * | 6/2020 | G02B 6/425 |
| DE | 102006041020 | A1 | | 3/2008 | |
| DE | 202013012494 | U1 | * | 3/2017 | |
| EP | 3543761 | A1 | * | 9/2019 | G03B 17/565 |
| JP | 2006-081842 | A | | 3/2006 | |
| JP | 2018175909 | A | * | 11/2018 | |
| KR | 2013067710 | A | * | 6/2013 | |
| KR | 10-1584737 | B1 | | 1/2016 | |
| KR | 1584737 | B1 | * | 1/2016 | A61B 5/0077 |
| KR | 2018131684 | A | * | 12/2018 | G06F 3/14 |
| RU | 2017146963 | A | * | 6/2019 | |
| WO | WO 2013/148367 | | | 10/2013 | |
| WO | WO-2015016377 | A1 | * | 2/2015 | A61B 5/0077 |
| WO | WO-2015116656 | A1 | * | 8/2015 | F21L 4/00 |
| WO | WO-2018030969 | A1 | * | 2/2018 | |
| WO | WO-2018155630 | A1 | * | 8/2018 | |
| WO | WO 2019/102480 | A1 | | 5/2019 | |
| WO | WO-2019148154 | A1 | * | 8/2019 | A61B 90/13 |
| WO | WO-2019153096 | A1 | * | 8/2019 | A61B 34/10 |
| WO | WO-2019207588 | A2 | * | 10/2019 | G06T 7/90 |
| WO | WO-2020008447 | A1 | * | 1/2020 | H04M 1/05 |
| WO | WO 2020/130598 | A1 | | 6/2020 | |
| WO | WO 2020/173955 | A1 | | 9/2020 | |
| WO | WO 2021/175713 | | | 9/2021 | |
| WO | WO 2021/191070 | | | 9/2021 | |
| WO | WO 2021/224929 | | | 11/2021 | |
| WO | WO 2021/224929 | A1 | | 11/2021 | |
| WO | WO 2021/236616 | | | 11/2021 | |
| WO | WO 2023/012792 | | | 2/2023 | |
| WO | WO 2023/209718 | | | 11/2023 | |

OTHER PUBLICATIONS

International Search Report and the Written Opinion Dated Aug. 5, 2021 From the International Searching Authority Re. Application No. PCT/IL2021/05523. (12 Pages).

International Search Report and the Written Opinion Dated Dec. 29, 2022 From the International Searching Authority Re. Application No. PCT/IL2022/050833. (21 Pages).

Invitation to Pay Additional Fees and Communication Relating to the Results of the Partial International Search Dated Nov. 9, 2022 From the International Searching Authority Re. Application No. PCT/IL2022/050833. (5 Pages).

Uthoff et al. "Point-of-Care, Smartphone-Based, Dual-Modality, Dual-View, Oral Cancer Screening Device with Neural Network Classification for Low-Resource Communities", PLOS One, (12):e0207493:1-21, Dec. 5, 2018.

International Preliminary Report on Patentability Dated Feb. 15, 2024 From the International Bureau of WIPO Re. Application No. PCT/IL2022/050833 (12 Pages).

Supplementary European Search Report and the European Search Opinion Dated Apr. 29, 2024 From the European Patent Office Re. Application No. 2179991.5. (15 Pages).

International Search Report and the Written Opinion Dated Aug. 13, 2023 From the International Searching Authority Re. Application No. PCT/IL2023/050429. (20 Pages).

Communication Pursuant to Article 94(3) EPC Dated Dec. 9, 2024 From the European Patent Office Re. Application No. 2179991.5. (5 Pages).

International Preliminary Report on Patentability Dated Nov. 7, 2024 From the International Bureau of WIPO Re. Application No. PCT/IL2023/050429. (13 Pages).

Supplementary European Search Report and the European Search Opinion Dated Sep. 24, 2025 From the European Patent Office Re. Application No. 22852491.4. (12 Pages).

* cited by examiner

INTRAORAL SCANNER

RELATED APPLICATIONS

This application is a National Phase of PCT Patent Application No. PCT/IL2021/050523 having International filing date of May 6, 2021, which claims the benefit of priority under 35 USC § 119 (e) of U.S. Provisional Patent Application No. 63/020,602 filed on May 6, 2020. The contents of the above applications are all incorporated by reference as if fully set forth herein in their entirety.

FIELD AND BACKGROUND OF THE INVENTION

The present invention, in some embodiments thereof, relates to dental measurement devices and methods and, more particularly, but not exclusively, to intraoral scanning devices and methods.

SUMMARY OF THE INVENTION

Following is a non-exclusive list including some examples of embodiments of the invention. The invention also includes embodiments which include fewer than all the features in an example and embodiments using features from multiple examples, also if not expressly listed below.

Example 1. A dental add-on for an electronic communication device having a screen and an imager, said add-on comprising:

a body comprising:

a distal portion sized and shaped to be at least partially inserted into a human mouth within, in one or more dimension, one or both dental arches; and an optical path extending from an optical element of said electronic communication device, through said body to said distal portion and configured to adapt a FOV of said optical element for dental imaging;

a connector for connection of said add-on body to said electronic communication device.

Example 2. The dental add-on according to example 1, wherein said optical path adapts said FOV for dental imaging by directing said FOV into said human mouth.

Example 3. The dental add-on according to any one of examples 1-2, wherein said optical element comprises said imager.

Example 4. The dental add-on according to examples 3, wherein said optical path comprises transfers a FOV including a view of at least a portion of said human mouth to said imager.

Example 5. The dental add-on according to any one of examples 1-4, wherein said optical element comprises an illuminator of said electronic communication device.

Example 6. The dental add-on according to example 5, wherein said optical path includes a patterning element.

Example 7. The dental add-on according to example 4, comprising a second optical path extending from an illuminator of said electronic communication device through said body to said distal portion, said second optical path configured to adapt a FOV of said illuminator for dental imaging.

Example 8. The dental add-on according to example 7, wherein said second optical path includes a patterning element.

Example 9. The dental add-on according to any one of example 1-8, wherein said screen is disposed on a front face of said electronic communication device, said camera is disposed on a back face of said electronic communication device; and wherein, when said body is connected to said electronic communication device, said optical path extends in a direction generally parallel to one or both of an orientation of said front face and an orientation of said back face.

Example 10. The dental add-on according to any one of examples 1-9, wherein said add-on comprises an add-on illuminator, where a FOV of said illuminator overlaps with said imaging FOV.

Example 10.1 The dental add-on according to example 10, wherein said add-on illuminator is powered by an add-on power source.

Example 10.2 The dental add-on according to any one of examples 10-10.1, wherein said add-on illuminator is powered by said electronic communication device.

Example 11. The dental add-on according to any one of examples 1-10.2, wherein said add-on comprises a pattern projector.

Example 12. The dental add-on according to any one of examples 10-11, wherein said pattern projector comprises said add-on illuminator and a patterning element disposed within an optical path between said illuminator and said FOV of said illuminator.

Example 13. The dental add-on according to example 5, wherein said pattern projector comprises one or more lens disposed within said optical path between said illuminator and said FOV of said illuminator.

Example 14. The dental add-on according to any one of examples 3-13, wherein said optical path includes one or more optical path element which changes optical power of light received by said optical path element to focus light within said optical path.

Example 15. The dental add-on according to example 14, wherein said one or more optical path elements are selected from the group comprising; curved mirror, lens, prism, and combinations thereof.

Example 16. The dental add-on according to any one of examples 1-15, wherein said optical path includes one or more mirror changing a direction of said optical path.

Example 17. The dental add-on according to any one of examples 1-16, wherein said connector is configured to align said optical path with said imager of said electronic communication device.

Example 18. The dental add-on according to example 17, wherein a position of said connector is adjustable with respect to said body.

Example 19. The add-on according to any one of examples 1-18, when said add-on body is elongate.

Example 20. The add-on according to any one of example 1-19, wherein a ratio of a length of said body measured along a longitudinal axis is at least 2 times a maximum transverse dimension of said body taken perpendicular to said longitudinal axis.

Example 21. The add-on according to examples 1-20, wherein said body, when attached to said electronic communication device, extends from a body of said electronic communication device by 2-10 cm in a direction of elongation of said body.

Example 22. The add-on according to examples 22, wherein said distal portion of said body has maximal dimensions perpendicular to said direction of elongation of 5-20 mm.

Example 24. The add-on according to any one of examples 19-22, wherein said direction of elongation of said body is 45-90 degrees to an orientation of said front face and said back face of said electronic communication device.

Example 25. The add-on of according to any one of examples 19-22, wherein said direction of elongation of said body is less than 20 degrees to an orientation of said front face and said back face of said electronic communication device.

Example 26. The add-on according to any one of examples 4-25, wherein said at least a portion of said human mouth includes a buccal and/or lingual view of one or more tooth.

Example 26.1 The add-on according to any one of examples 4-26, comprising one or more calibration target appearing within said FOV of said imager.

Example 27. A method of manufacture of an add-on according to any one of examples 1-26 comprising:

providing a first portion of said add-on, said first portion comprising said distal portion of said add-on;

Example 3D printing a second portion of said add-on, said second portion comprising said connector; and connecting said first portion and said second portion.

Example 28. The method of manufacture according to example 27, comprising receiving customization data; and wherein said 3D printing is according to said customization data.

Example 29. The method of manufacture according to example 28, wherein said receiving is from said electronic communication device.

Example 30. A method of intraoral imaging comprising: re-directing one or more electronic communication device optical element FOV into a mouth by transferring said optical element FOV in a direction generally parallel to a face of said optical element, using one or more intraoral optical element;

directing said device optical element FOV toward one or more dental surface; adapting said one or more FOV for dental scanning.

Example 31. The method of intraoral imaging according to example 30, wherein said re-directing is into said mouth within, in one or more dimension, one or both dental arches.

Example 32. The method according to any one of said examples 30-31, wherein said one or more electronic optical element FOV comprises an imaging FOV of an imager of said electronic communication device.

Example 33. The method according to example 32, comprising illuminating with an illumination FOV which overlaps with said imaging FOV for a plurality of dental measurement distances.

Example 34. The method according to example 33, comprising patterning said illuminating.

Example 35. The method according to example 33, wherein said one or more device optical element FOV comprises an illuminator FOV.

Example 36. The method according to any one of examples 30-35, wherein adapting includes focusing said device optical element FOV.

Example 37. The method according to any one of examples 16-18, wherein said re-directing comprises changing an orientation of said device optical element FOV.

Example 38. The method according to any one of examples 32-37, comprising receiving one or more image through said imaging FOV.

Example 39. The method according to example 38, comprising determining one or more measurement from said one or more image.

Example 40. The method according to any one of examples 38-39, comprising generating a 3D model of dental features using said one or more image.

Example 41. The method according to example 40, wherein said one or more image comprises a plurality of images;

wherein said generating comprises combining said plurality of images.

Example 42. The method according to example 41, wherein said plurality of images comprise images across a dental arch;

wherein said generating comprises generating a 3D model of said dental arch.

Example 43. The method according to example 42, comprising collecting one or more image from an additional FOV;

wherein said generating comprises combining said plurality of images using said one or more image from an additional FOV.

Example 44. A method of intraoral imaging comprising: aligning one or more optical element of an electronic communication device to one or more optical path of an add-on to transfer a FOV of said optical element into said add-on optical path;

attaching said add-on to said electronic communication device; and positioning said FOV of said optical element within a mouth, by positioning at least a portion of said add-on within said mouth.

Example 45. The method according to example 44, wherein said one or more optical element comprises an imager; and wherein said method comprises acquiring one or more image of a dental feature using said imager.

Example 46. A dental add-on for an electronic communication device having a screen on a front face and a camera on a back face of the electronic communication device, said add-on comprising:

a body comprising:

a distal portion;

a connector for connection of said add-on body to said electronic communication device; and one or more optical path, when said body is connected to said electronic communication device, said optical path extending in a direction generally parallel to one or both of an orientation of said front face and an orientation of said back face, where said optical path is configured to adapt one or more of an illumination FOV of said electronic communication device and an imaging FOV of said electronic communication device for dental imaging.

Example 47. A method of intraoral imaging comprising:

re-directing one or more electronic communication device optical element FOV into a mouth within, in one or more dimension, one or both dental arches using one or more intraoral optical element;

directing said optical element FOV toward one or more dental surface;

adapting said one or more FOV for dental scanning.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such collecting dental measurements, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
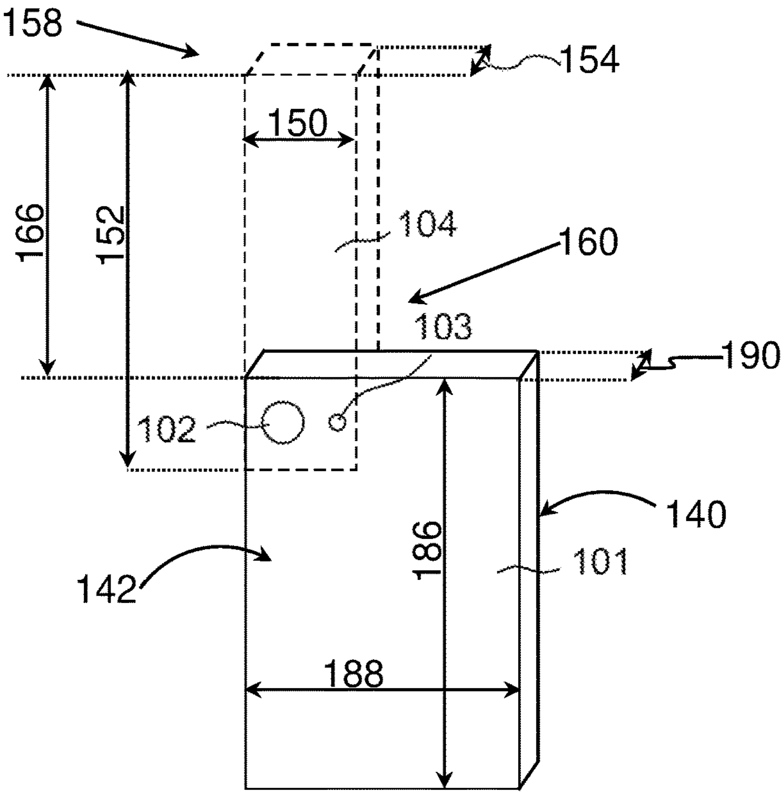
FIG. 1 is a simplified schematic of an add-on connected to a smartphone, according to some embodiments of the invention.

The present invention, in some embodiments thereof, relates to dental measurement devices and methods and, more particularly, but not exclusively, to intraoral scanning devices and methods.

Overview

A broad aspect of some embodiments of the invention relates to adapting an electronic communication device and/or a handheld electronic device (e.g. smartphone) for intraoral scanning. Where intraoral scanning, in some embodiments, includes collecting one or more optical measurement (e.g. image) of dental feature/s and, optionally, other dental measurements. In some embodiments, an add-on is connected to the smartphone, for example, enabling one or more feature of the smartphone to be used for intraoral scanning e.g. within a subject's mouth.

An aspect of some embodiments relates to an add-on device which adapts one or more optical element of the smartphone for dental imaging. Optical elements including, for example, one or more imager and/or illuminator.

In some embodiments, adapting of optical elements includes transferring a FOV of the optical element (or at least a portion of the FOV of the optical element) to a different position.

In this document, regarding imagers and/or imaging, description is of transfer of the FOV of the imager through an optical path of the add-on. However, it should be understood that this refers to an optical path through the add-on providing light emanating from a FOV region (e.g. outside the add-on) to the imager. In some embodiments, the light includes light emanating from (e.g. reflected by) one or more internal surface within the add-on.

In some embodiments, the FOV region and/or a portion of an add-on is positioned within and/or inside a subject's mouth and/or oral cavity e.g. during scanning with the add-on and smartphone. Where, in some embodiments, positioning is within a space defined by a dental arch of one or more of the subject's jaws. An imaging FOV and/or images acquired with the add-on for example, including lingual region/s of one or more dental feature (e.g. tooth and/or dental prosthetic) and/or buccal region/s of dental feature/s e.g. the features including pre-molars and/or molars.

In some embodiments, the add-on moves a FOV of one or more imager and/or one or more illuminator away from a body of the smartphone. For example, by 1-10 cm, in one or more direction, or lower or higher or intermediate ranges or distances. For example, by 1-10 cm in a first direction, and by less than 3 cm, or less than 2 cm, or lower or higher or intermediate distances, in other directions.

In some embodiments, the add-on, once attached to the smartphone extends (e.g. a central longitudinal axis of the add-on e.g. elongate add-on body) in a parallel direction (or at most 10 or 20 or 30 degrees from parallel) to one or both faces of the smartphone.

In some embodiments, the add-on, once attached to the smartphone extends (e.g. a central longitudinal axis of the add-on e.g. elongate add-on body) in a perpendicular direction (or at or at most 10 or 20 or 30 degrees from perpendicular) to one or both faces of the smartphone. A potential benefit being ease of viewing of the smartphone screen. For example, directly e.g. where the add-on extends from a screen face of the smartphone. For example, indirectly e.g. via a mirror generally opposite the subject.

In some embodiments, an angle of extension is between perpendicular and parallel. For example an angle of extension of the add-on from the smartphone of 30-90 degrees.

Where the add-on moves and/or transfers the FOV/s, for example, in a direction (e.g. a direction of a central longitudinal axis of the add-on body) generally parallel (e.g. within 5, or 10, or 20 degrees of parallel) to a front and/or back face of the smartphone. Where, in some embodiments, the front face hosts a smartphone screen and the back face hosts one or more optical element of the smartphone (e.g. imager, e.g. illuminator). In some embodiments, a smallest cuboid shape enclosing outer surfaces of the smartphone defines faces and edges of the smartphone. Where, in some embodiments, faces are defined as two opposing largest sides of the cuboid and edges are the remaining 4 sides of the cuboid.

Where in some embodiments, including perpendicular, parallel and between perpendicular and parallel directions of extension of the add-on elongate body from an orientation the smartphone face, FOVs emanating from the add-on body (e.g. imaging and/or illuminating) are perpendicular from the longitudinal axis of the add-on body (or at most 10 degrees, or 20 degrees, or 30 degrees from perpendicular).

Where in some embodiments, including perpendicular, parallel and between perpendicular and parallel directions of extension of the add-on elongate body from an orientation the smartphone face, FOVs emanating from the add-on body (e.g. imaging and/or illuminating) are parallel from the longitudinal axis of the add-on body (or at most 10 degrees, or 20 degrees, or 30 degrees from perpendicular). For example extending from a distal tip of the add-on body.

In some embodiments, at least a portion (e.g. a body of the add-on) of the add-on is sized and/or shaped for insertion into a human mouth. One or more FOV, in some embodiments, emanating from this portion.

In some embodiments, transfer is by one or more transfer optical element, the element/s including mirror/s and/or prism/s and/or optical fiber. In some embodiments, one or more of the transfer element/s has optical power, e.g. a mirror optical element has a curvature.

In some embodiments, transfer is through an optical path, and the add-on includes one or more optical path for one or more device optical element e.g. smartphone imager/s and/or illuminator/s. In some embodiments, optical path/s pass through a body of the add-on. In some embodiments, transfer of FOV/s includes shifting a point and/or region of emanation of the FOV from a body of the smartphone to a body of the add-on.

In some embodiments, FOV/s of illuminator/s are adjusted for dental imaging. Where, in some embodiments, one or more of illumination intensity, illuminator color, illumination extent are selected and/or adjusted for dental imaging.

In some embodiments, an add-on illuminator optical path includes a patterning element. Where, for example, an optical path for light emanating from an illuminator of the smartphone (and/or from an illuminator of the add-on) patterns light emanating from the add-on. Alternatively, or additionally, in some embodiments, an illuminator is configured to directly illuminate with patterned light e.g. where the smartphone screen is used as an illuminator.

In some embodiments, the patterned light incident on dental feature/s (e.g. when the add-on is at least partially inserted into a mouth) is suitable to assist in extraction of geometry (e.g. 3D geometry) of the dental feature/s from images of the dental features lit with the patterned light. Where, for example, in some embodiments, separation between patterning elements (e.g. lines of a grid) is 0.1-3 mm, or 0.5-3 mm, or 0.5 mm-1 mm, or lower or higher or intermediate separations or ranges, when the light is incident on a surface between 0.5-5 cm, or 0.5-2 cm, or lower or higher or intermediate distances or ranges, from a surface of the add-on from which the FOV emanates.

In some embodiments, the illuminator optical path includes one or more additional element having optical power, for example, one or more lens and/or prism and/or curved mirror. Where, for example, in some embodiments, element/s having optical power adjust the projected light FOV to be suitable for dental imaging with the add-on. For example, in some embodiments, an angle of a projection FOV is adjusted to overlap with one or more imaging FOV (alternatively or additionally, in some embodiments, an imaging FOV is adjusted to overlap with one or more illumination FOV). In some embodiments, projected light is focused by one or more lens.

In some embodiments, an imager FOV for one or imager is adjusted by the add-on, e.g. by one or more optical element optionally including optical elements having optical power e.g. mirror, prism, optical fiber, lens. Where adjusting includes, for example, one or more of; transferring, focusing, and splitting of the FOV.

In some embodiments, performance and/or operation of device optical element/s of the smartphone are adapted for intraoral scanning. For example, in some embodiments, optical parameter/s of one or more optical element are adjusted. For example, by software installed on the smartphone, the software interfacing with smartphone control of the optical elements.

In some embodiments, scanning includes collecting images of dental features using one or more imager e.g. imager of the smartphone. Where, in some embodiments, the imager acquires images through the add-on (e.g. through the optical path of the add-on). In some embodiments, one or more imager imaging parameter (e.g. of the smartphone) is controlled and/or adjusted e.g. for intraoral scanning. For example, position of emanation and/or orientation of an imaging FOV. For example, in some embodiments, one or more of imager focal distance and frame rate are selected and/or adjusted for dental scanning. For example, in some embodiments, a subset of sensing pixels (e.g. corresponding to a dental region of interest ROI) are selected for image acquisition.

In some embodiments, one or more parameter of one or more illuminator e.g. of the smartphone is adjusted and/or controlled. For example, one or more of; when one or more illuminator is turned on, which portion/s of an illuminator are illuminated (e.g. in a multi-LED illuminator which LEDs are activated), color of illumination, power of illumination.

In some embodiments, during acquisition of images, at least a portion of the add-on is inserted into the subject's mouth for example, potentially enabling collection of images of inner dental surfaces. In some embodiments, e.g. where the add-on remains outside the mouth, one or more mirror positioned within the mouth enables imaging of inner dental regions.

In some embodiments, one or more fiducial is used during scanning and/or calibration of the add-on connected to the smartphone.

Where, in some embodiments, fiducial/s are attached to the user. In some embodiments, the fiducial is positioned in a known position with respect to dental feature/s. For example, by attachment directly and/or indirectly to rigid dental structures e.g. attachment to a tooth e.g. attachment by a user biting down on a biter connected to the fiducial/s.

In some embodiments, the fiducials are used in calibration of scanned images e.g. where fiducial/s of known color and/or size and/or position (e.g. position with respect to the add-on and/or smartphone) are used to calibrate these features in one or more image and/or between images.

In some embodiments, a cheek retractor is used during scanning, for example, to reveal outer surfaces of teeth. In some embodiments, the cheek retractor includes one or more fiducial and/or mirror e.g. positioned within the oral cavity.

A broad aspect of some embodiments of the invention relates to a user performing a self-scan (e.g. dental self-scan) using an add-on and a smartphone (e.g. the user's smartphone).

In some embodiments, the user is guided during scanning. For example by one or more communication through a smartphone user interface. For example, by aural cues e.g. broadcast by smartphone speaker/s. For example, by one or more image displayed on the smartphone screen. Where, in some embodiments, while a portion of the add-on is within the user's mouth, the user views the image/s displayed on the smartphone screen.

In some embodiments, when the add-on attached to the smartphone is used for scanning, the smartphone is orientated so that the user can directly view the smartphone screen. Where, for example, the add on extends into the mouth from a lower portion of a front face of the smartphone, e.g. a central longitudinal axis of the add-on being about perpendicular, or within 20-50 degrees of perpendicular to a plane of the smartphone screen and/or front face.

In some embodiments, when the add-on attached to the smartphone is used for scanning, the smartphone screen is orientated away from the user and the user views the screen in a reflection of the screen in a mirror. For example, an external mirror e.g. opposite to the user e.g. mirror on a wall.

In some embodiments, the add-on includes one or more mirror angled with respect to the smartphone screen and user's viewpoint to reflect at least a portion of the smartphone screen towards the user.

In some embodiments, display to a user is 3D, where, in some embodiments different colored display on the smartphone screen is selected to produce a 3D image when the user is wearing a corresponding pair of glasses. For example, red/cyan 3D image production.

In some embodiments, displayed images are focused so that the image plane is not at the smartphone screen. For example, where the screen (and/or reflection of the screen) is close to the user, placing the image plane at a more comfortable viewing distance e.g. further away from the user than the smartphone screen.

In some embodiments, dental scanning using the add-on and a smartphone is performed by a subject themselves e.g. at home. Where, in some embodiments, collected measurement data is processed and/or shared for example, to provide monitoring (e.g. to a healthcare professional) and/or to provide feedback to the subject. The subject self-scanning potentially enables monitoring and/or treatment of the subject more frequently than that provided by in-office dental visits and/or imaging using a standard intraoral scanner.

In some embodiments, dental scanning using the add-on and a smartphone is performed, for example, by a user (e.g. at home and/or without the user having an in-person appointment with a healthcare professional) is performed periodically e.g. to monitor the subject. Where, in some embodiments, the scanning data is reviewed, for example, by a healthcare professional. In some embodiments, scanning and/or monitoring is of one or more of; oral cancer, gingivitis, gum inflammation, cavity/ies, dental decay, plaque, calculus, tipping of teeth, teeth grinding, erosion, orthodontic treatment (e.g. alignment with aligner/s), teeth whitening, tooth-brushing.

In some embodiments, scan data is used as an input to an AI based oral care recommendation engine. Where the engine, in some embodiments, outputs instructions and/or recommendations (e.g. which are communicated to the subject), based on the scan data e.g. one scan and/or periodic scan data over time.

Throughout this document the term "smartphone" has been used, however this term, for some embodiments, should be understood to also refer to and encompass other electronic devices, e.g. electronic communication devices, for example, handheld electronic devices, e.g. tablets, watches.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Add-On

FIG. 1 is a simplified schematic of an add-on 104 connected to a smartphone 101, according to some embodiments of the invention.

In some embodiments, add-on 104 is connected to smartphone 101 (e.g. as illustrated in FIG. 1), for example, for scanning of teeth inside a mouth using smartphone 101 and add-on 104.

In some embodiments, add-on 104 includes a proximal end 160 and a distal end 158. Where, in some embodiments, proximal end 160 is connected to smartphone 101.

In some embodiments, distal end 154 is sized and/or shaped for insertion into a human mouth and/or for intraoral scanning. In some embodiments, add-on 104 has a length 152, a width 150 and a depth 154. In some embodiments, length 152 has one or more feature as illustrated and/or described regarding length 252 FIG. 2A. In some embodiments, width 150 and/or depth 154 have one or more feature as illustrated and/or described regarding width 254.

In some embodiments, the add-on has a distal tip face 299. Where, in some embodiments, an FOV emanates from the face (e.g. refer to FOV 409A emanating from distal tip face 478 FIG. 4A). Where, in some embodiments, an FOV emanates at about 90 degrees from an orientation of the distal tip face.

Figure 27A:
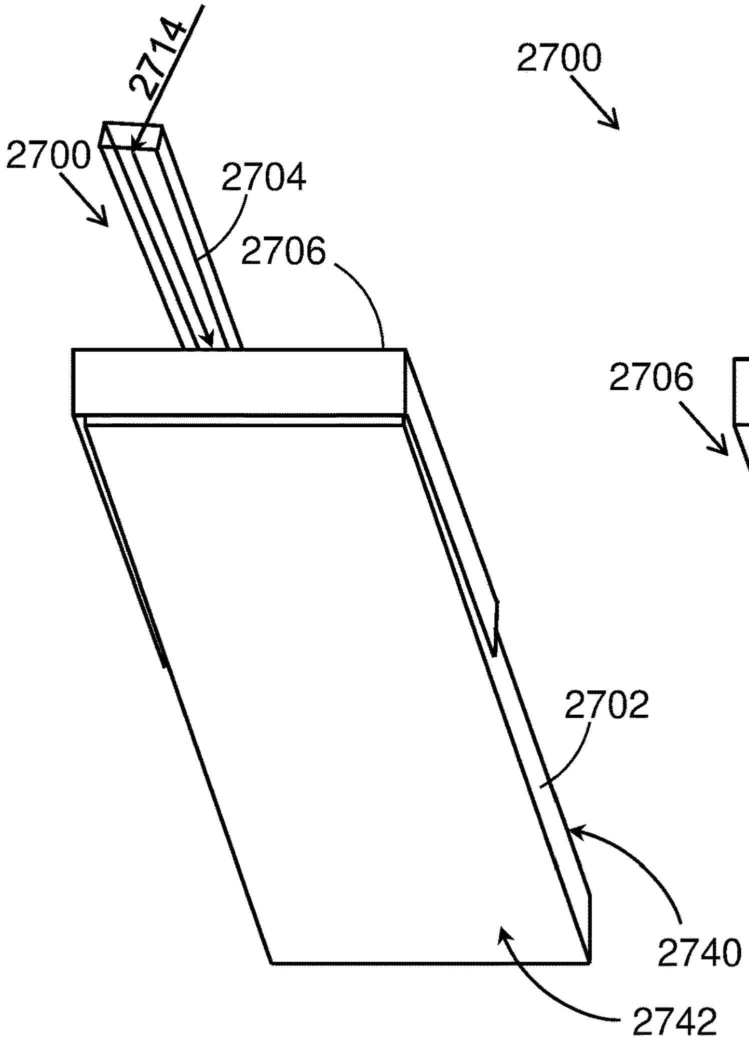
FIG. 27A is a simplified schematic of an add-on attached to a smartphone, according to some embodiments of the invention.
Figure 27B:
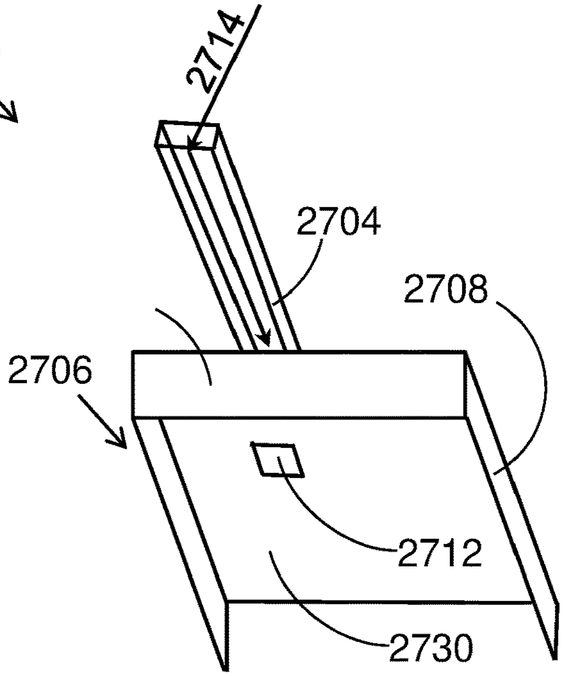
FIG. 27B is a simplified schematic of an add-on, according to some embodiments of the invention.
Figure 27C:
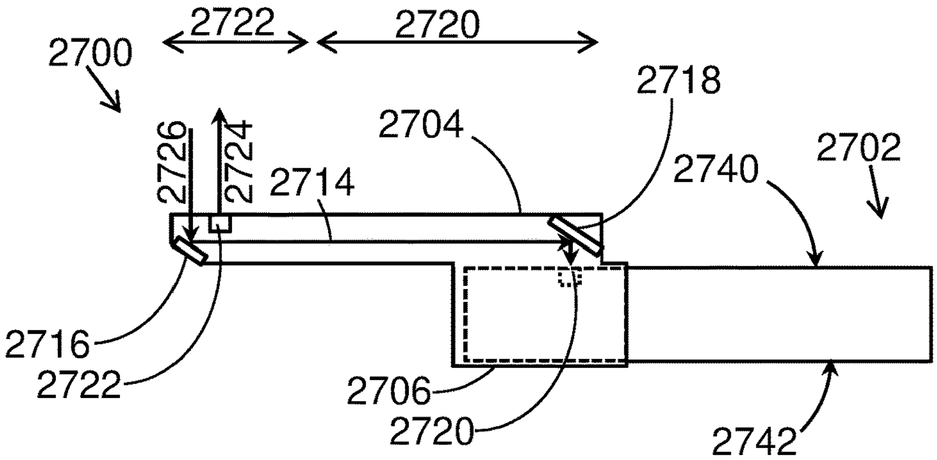
FIG. 27C is a simplified schematic side view of an add-on according to some embodiments of the invention.

In some embodiments, the distal tip face is angled, for example, including one or more feature as illustrated in and/or described regarding the distal tip face of add-on 2700 FIG. 27C.

In some embodiments, a length 166 of add-on 104 extending distally from a body of smartphone 101 is about 50 mm or about 40 mm or about 60 mm, or of 30-100 mm, or 40-80 mm, or 50-60 mm, or lower or higher or intermediate lengths.

In some embodiments, add-on 104 is elongate, for example, where length 152 and/or length 166 are 1.5-20 times width 250 and/or depth 154 of the body of the add-on, or lower or higher or intermediate multiples or ranges.

In some embodiments, smartphone 101 includes at least one imager (e.g. a camera) 102 and/or at least one illuminator 103. In some embodiments, illuminator 103 includes at least one flash LED (light emitting diode).

In some embodiments, add-on 104 adapts lighting (e.g. as provided by illuminator 103) and/or imaging (e.g. by camera 102) for intraoral scanning. In some embodiments, add-on moves a field of view (FOV) of imager 102 and/or illuminator 103. For example, away from cell phone body 101, in at least one direction e.g. by about 50 mm or about 40 mm or about 60 mm, or of 30-100 mm, or 40-80 mm, or 50-60 mm, or lower or higher or intermediate distances. In some embodiments, FOV/s are moved away from cell phone body in a single direction, for example, in a direction parallel (or within 20 degrees of) a longitudinal axis of the smartphone. For example, in some embodiments, add-on 104 includes one or more optical pathway extending, for example, from proximal end 160 (and/or a proximal region of the add-on) to distal end 158 (and/or a distal region of the add-on).

In some embodiments, smartphone 101 has a length 186 and a width 188 both of which are larger than a depth 190. In some embodiments, length 196 is larger than width 188.

Figure 2A:
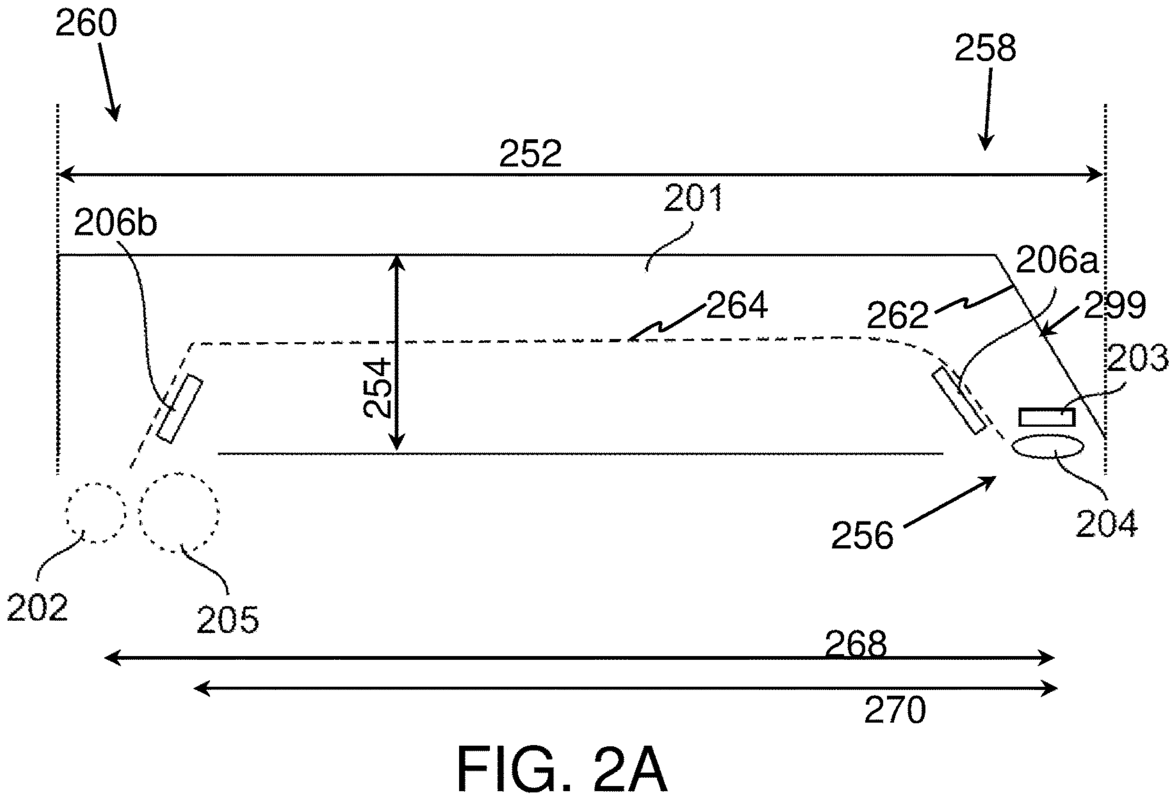
FIG. 2A is a simplified schematic cross sectional view of an add-on, according to some embodiments of the invention.

In some embodiments, camera 102 and illuminator 103 are separated from each other e.g. on a second face 142 of smartphone 101 for example, separated from each other in a transverse direction e.g. in a width-ways direction with respect to smartphone 101 body. (In some embodiments, camera 102 and illuminator 103 are separated from each other in a longitudinal direction e.g. in a length-way direction with respect to smartphone 101 body e.g. as illustrated in FIG. 2A regarding camera 205 and illuminator 202). Where, in some embodiments, a smartphone screen (not illustrated) is located on a first face 140 of smartphone 101.

FIG. 2A is a simplified schematic cross sectional view of an add-on 201, according to some embodiments of the invention.

In some embodiment, add-on 201 has a body with a proximal end 260 and a distal end 258.

In some embodiments, teeth scanning add-on 201 is configured to fit, at least partially, inside a mouth e.g. a human mouth, e.g. an adult human mouth. In some embodiments, add-on 201 is narrow (e.g. in one or two dimensions) and/or long.

Where, in some embodiments, add-on 201 has a width (e.g. a dimension into a plane of the figure) and/or depth 254 of about 10 mm or about 15 mm or about 20 mm, or of 5-30 mm, or 10-20 mm, or lower or higher or intermediate widths or ranges.

In some embodiments, add-on 201 has a length 252 of about 50 mm or about 40 mm or about 60 mm, or of 30-100 mm, or 40-80 mm, or 50-60 mm, or lower or higher or intermediate lengths.

In some embodiments, add-on 201 is elongate, for example, where length 252 is 1.5-20 times width 150 (and/or the depth) of the body of the add-on, or lower or higher or intermediate multiples or ranges.

In some embodiments, add-on 104 provides an optical path for light from illuminator 202 (which, for example, includes one or more LED) and/or imager 205 to the add-on distal edge and/or distal end 258.

In some embodiments, add-on 201 includes a pattern projector 256 which, for example, includes a pattern 203 and optionally a lens 204 through which light is projected to project a pattern on dental feature/s e.g. teeth.

Where, in this document the term "pattern", in some embodiments, relates to a patterning element which comprises a light absorbing pattern, which is optionally hosted by a transparent element. For example, in some embodiments, the light absorbing pattern is disposed on a surface of a transparent element. In some embodiments, the pattern and lens are a single element, a lens hosting the pattern.

In some embodiments, light reflected (e.g. including patterned light) from within a subject's mouth is transferred from the mouth to camera 205. In some embodiments, the optical path for the light within the subject's mouth is provided by one or more mirror, for example, reflected to camera 205 using mirrors 206*a* and 206*b*.

In some embodiments, one or more optical path through add-on 201 is separated from other optical path/s. For example, in some embodiments, add-on 201 includes a divider 264 which prevents interference between illumination light (e.g. transferred from illuminator 202 through a body of add-on 201) and light transferred through the body of add-on 201 to be sensed by imager 205. In some embodiments, divider 264 includes material which does prevents passage of light through it. For example, opaque and/or light absorbing material and/or reflective material.

In some embodiments, the body of add-on 201 includes material which prevents passage of light through it. For example, opaque and/or light absorbing material and/or reflective material.

In some embodiments, add-on 201 includes an additional lens (not illustrated) is positioned in an optical path of imager 205. Where, in some embodiments, the additional lens is a magnification lens (e.g. an afocal zoom lens). In some embodiments, the additional lens narrows imager FOV so that a larger proportion of the imager pixels acquire teeth images.

In some embodiments, the single CMOS FOV is split into two FOVs that capture different areas of the teeth or mouth. In some embodiments it is done using two mirrors that reflect each side of the FOV to a slightly different direction.

In some embodiments, one or more optical path of an add-on includes a single mirror, where, in some embodiments, a FOV transferred by the optical path is transferred, for example, at most by 90 degrees.

Figure 26:
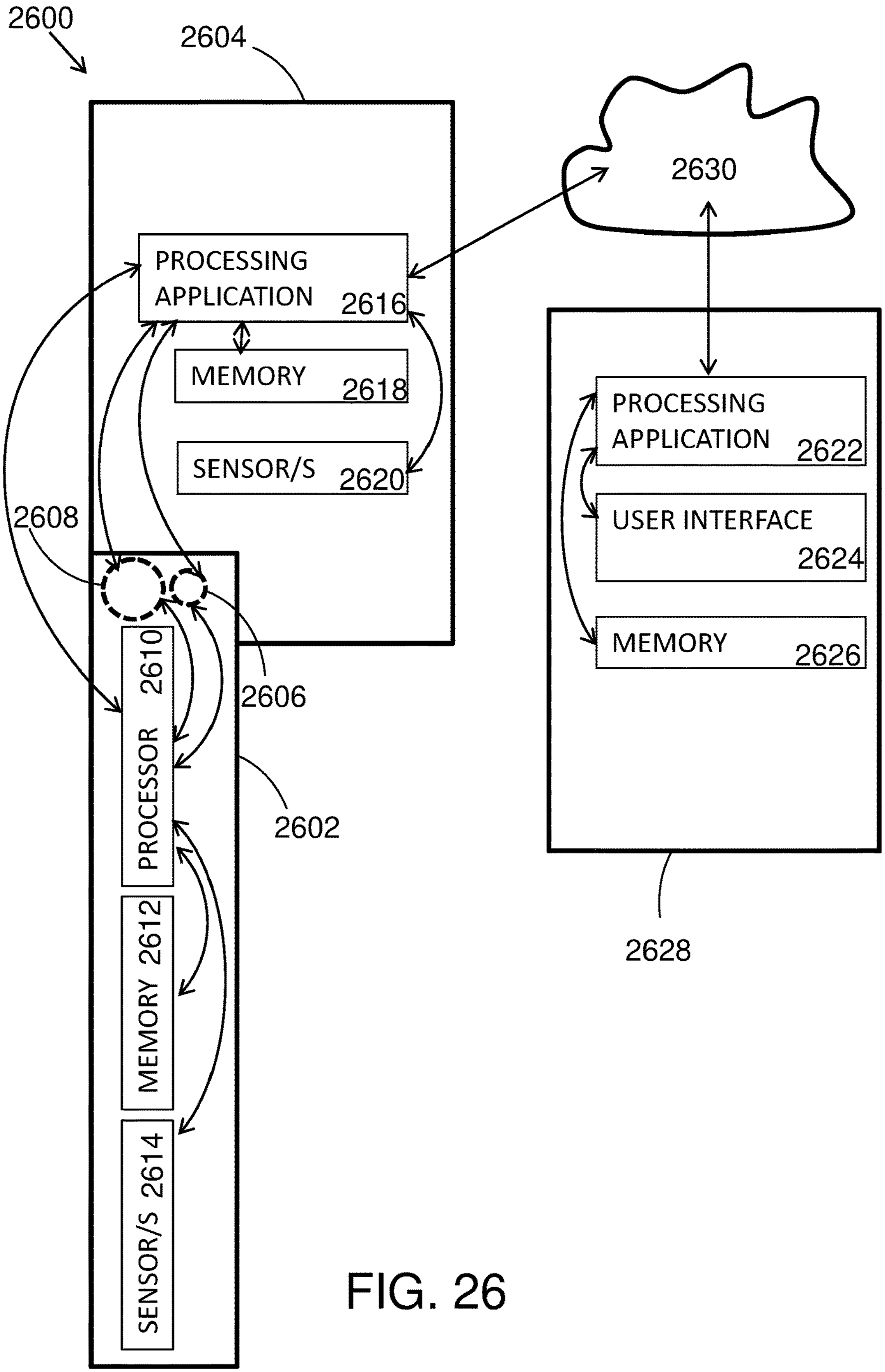
FIG. 26 is a simplified schematic of a dental measurement system, according to some embodiments of the invention.

FIG. 26 is a simplified schematic of a dental measurement system 2600, according to some embodiments of the invention.

In some embodiments, system 2600 includes a smartphone 2604 attached to an add-on 2602. Where add-on 2602 has one or more feature of add-ons as described elsewhere in this document.

In some embodiments, add-on 2602 is mechanically connected to smartphone 2604. In some embodiments, optical elements 2608, 2606 of the smartphone are aligned with optical pathways of add-on 2602.

In some embodiments, smartphone 2604 includes a processing application 2616 (e.g. hosted by a processor of the smartphone) which controls one or more optical element 2608, 2606 of the smartphone (e.g. imager and/or illuminator) and/or receives data from the element/s e.g. images collected by imager 2608.

In some embodiments, processing application 2616 stores collected images in a memory 2618 and/or uses instructions and/or in memory in processing of the data. For example, in some embodiments, previous scan data is stored in memory 2618 is used to evaluate a current scan. In some embodiments, one or more additional sensor 2620 is connected to processing application 2616 receiving control signals and/or sending sensor data to the processing application. For example, in some embodiments, IMU measurements are used in evaluating and/or processing collected images. For example, in some embodiments, illumination and/or imaging is carried out by additional optical elements of the smartphone which, for example, are not optically connected to the add-on.

Optionally, in some embodiments, the add-on includes a processor 2610 and/or a memory 2612 and/or sensor/s 2614. In some embodiments, add-on sensor/s include one or more imager. In some embodiments, processor 2610 has a data connection to the smartphone processing application 2616.

In some embodiments, the smartphone is connected to other device/s 2628 e.g. via the cloud 2630. In some embodiments, processing of data (e.g. generation of 3D model/s using collected images and optionally other data) is performed in the cloud. In some embodiments, it is performed by one or more other device 2628. For example, at a dental surgery, for example, a dental practitioner's device 2628. Where, in some embodiments, inputted instructions via a user interface 2624 are transmitted to the subject's smartphone 2604 e.g. to control and/or adjust scanning and/or interact with the subject.

Figure 24:
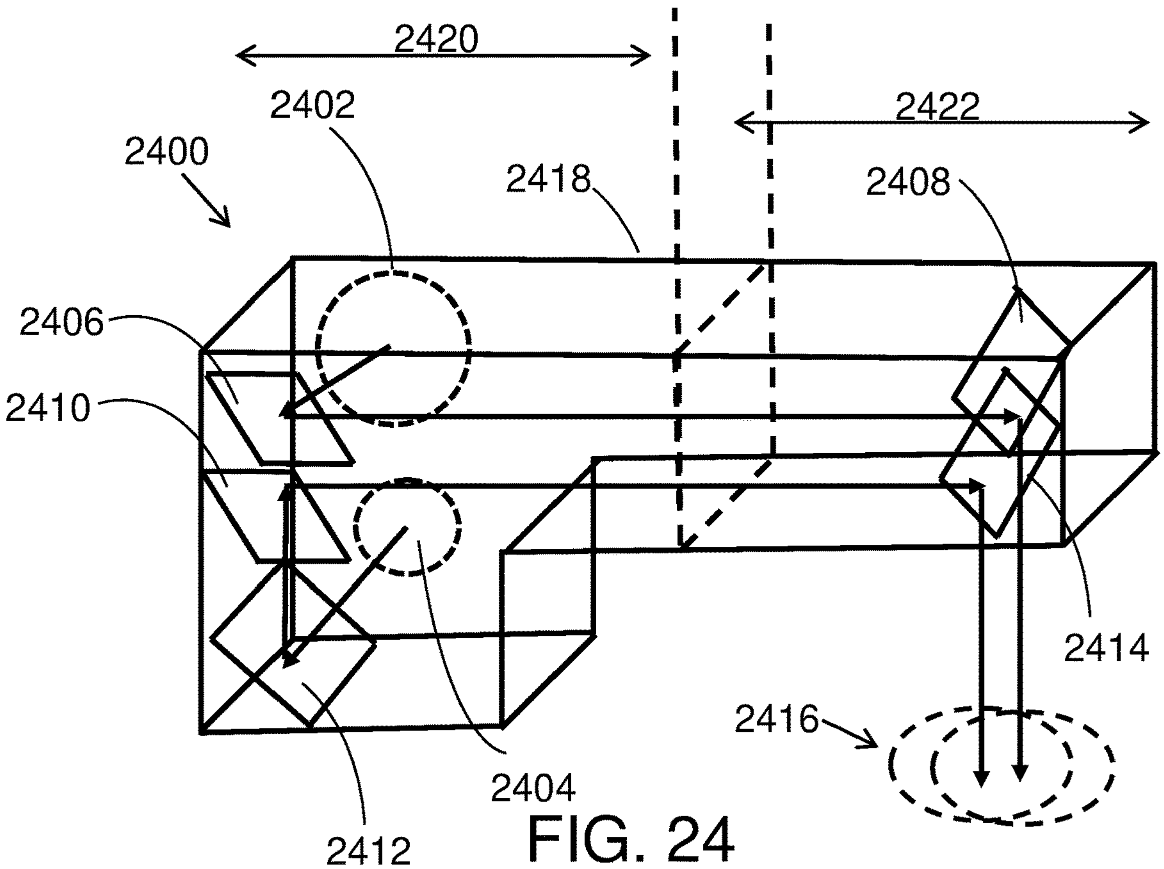
FIG. 24 is a simplified schematic of an add-on according to some embodiments of the invention.

FIG. 24 is a simplified schematic of an add-on 2400 according to some embodiments of the invention.

Figure 25:
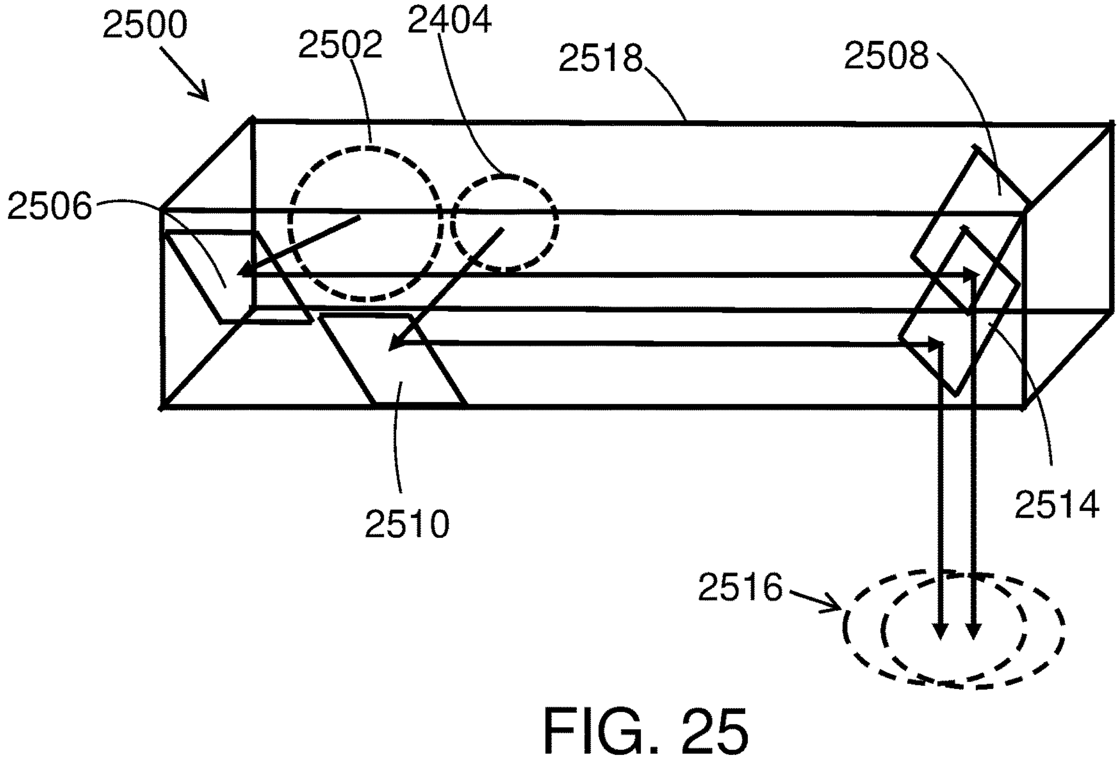
FIG. 25 is a simplified schematic of an add-on according to some embodiments of the invention.

FIG. 25 is a simplified schematic of an add-on 2500 according to some embodiments of the invention.

FIG. 24 and FIG. 25, in some embodiments illustrate transfer through a body 2418, 2518 of add-on 2400, 2500 of optical elements. For example, of an imaging FOV 2402, 2502 and an illumination FOV 2404, 2504. Where the transferred FOVs exit the add-on to at least partially overlap 2416, 2516.

Referring now to FIG. 24, in some embodiments, a FOV of an optical element 2402 is directed in more than one direction (e.g. by more than one optical element 2412, 2410) for example, before a final redirection before exiting the add-on at optical element 2114. Add-on 2400 in some embodiments, is used for optical elements disposed linearly and in an opposite direction to a desired direction of extension of an elongate 2418 body of the add-on.

Referring now to FIG. 25, in some embodiments, optical elements 2402, 2404 are arranged linearly with respect to an axis of transfer of the FOVs and/or with respect to an axis of elongation of the add-on. In some embodiments, the add-on is aligned to smartphone optical elements 2402, 2404. For example, to enable transfer of FOVs of the optical elements by add-on optical elements (e.g. mirrors) 2506, 2510, 2514, 2508 of the optical paths of the add-on.

Referring to both FIG. 24 and FIG. 25, in some embodiments, distal portions of both of the add-ons are the same. For example, potentially enabling construction of a variety of add-ons using a same distal part.

Exemplary Methods

Figure 2B:
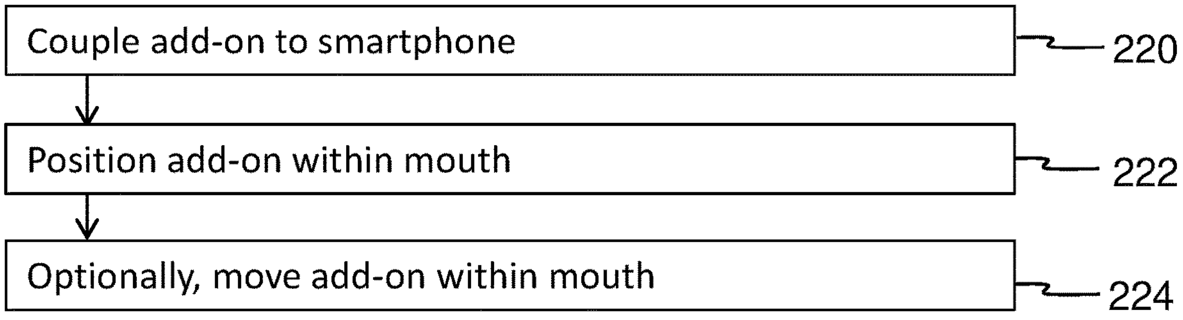
FIG. 2B is a method of intraoral scanning, according to some embodiments of the invention.

FIG. 2B is a method of intraoral scanning, according to some embodiments of the invention.

At 220, in some embodiments, an add-on is coupled to a smartphone. For example, connected mechanically (e.g. as described elsewhere in this document). For example, additionally or alternatively to a mechanical connection, data connected (e.g. as described elsewhere in this document)

In some embodiments, coupling is by placing at least a portion of the smartphone into a lumen of the add-on. Where, in some embodiments, the lumen is sized and/or shaped to fit the smartphone sufficiently closely that friction between the smartphone and the add-on holds the smartphone in position with respect to the add-on. In some embodiments, add-on lumen is flexible and/or elastic, deformation (e.g. elastic deformation) of the add-on acting to hold the add-on and smartphone together.

Additionally, or alternatively, in some embodiments, coupling includes adhering (e.g. glue, Velcro) and/or using one or more connector e.g. connector/s wrapped around the add-on and smartphone. Additionally, or alternatively, in some embodiments, coupling includes one or more interference fit (e.g. snap-together) and/or magnetic connection.

At 222, in some embodiments, at least a portion of the add-on is positioned within the subject's mouth. For example, by the subject themselves. In some embodiments, an edge and/or end of the add-on is put into the mouth. In some embodiments, only the add-on enters the oral cavity and the smartphone remains outside. Alternatively, in some embodiments, a portion of the smartphone enters the oral cavity e.g. an edge and/or corner of the smartphone e.g. which is attached to the add-on.

At 224, in some embodiments, the add-on is moved within the subject's mouth. For example, by the subject e.g. where, in some embodiments, the subject moves the add-on according to previously received instructions and/or instructions and/or prompts communicated to the subject e.g. via one or more user interface of the smartphone.

Figure 21:
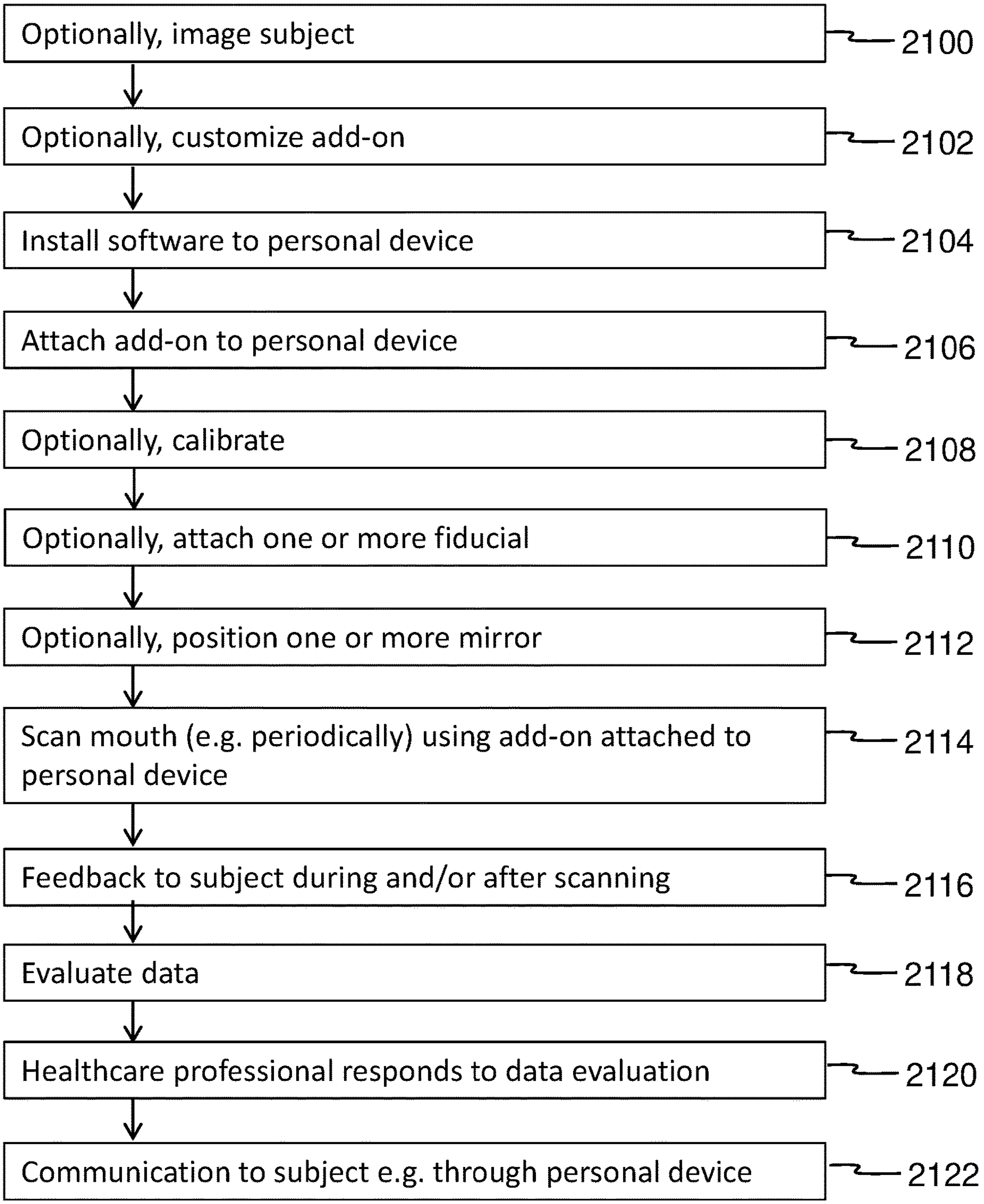
FIG. 21 is a flowchart of a method, according to some embodiments of the invention.

FIG. 21 is a flowchart of a method, according to some embodiments of the invention.

At 2100, optionally, in some embodiments, the subject is imaged. For example, using one or more type of imaging e.g. x-ray, MRI, ultra-sound. In some embodiments, the subject is imaged using an intraoral scanner e.g. a commercial dental intraoral scanner e.g. where scanning is by a healthcare professional. In some embodiments, the subject is imaged by a healthcare professional using an add-on and a smartphone e.g. the subject's smartphone. For example, to collect initial scan data. For example, as part of training the subject in self-scanning using the add-on.

In some embodiments, imaging data (e.g. from one or more data source) is used to generate a model (e.g. 3D model) of oral feature/s inside the mouth for the subject.

At 2102, optionally, in some embodiments, the add-on is customized.

In some embodiments, an add-on is customized and/or designed and/or adjusted to fit smartphone mechanical dimensions and/or optics (e.g. imager/s and/or illuminator/s (e.g. LED/s)) positions.

In some embodiments, customizing includes selecting relative position of optical pathways of the add-on and/or connection and/or connectors of the add-on. Where, in some embodiments, selecting is based on position and/or size of smartphone feature/s e.g. of the smartphone to be used in performing the scanning. Where feature/s include, for example, one or more of smartphone camera size and/or position on the smartphone, smartphone illuminator size and/or position on the smartphone, smartphone external (e.g. of the smartphone body) dimension/s, smartphone display size and/or position. In some embodiments, selecting is additionally or alternatively based on smartphone camera and/or illuminator and/or screen features e.g. camera resolution; number of pixels, pixel size, sensitivity, focal distance, illuminator; power, field of view, color of illuminating light.

In some embodiments, customizing includes adjusting one or more portion of the add-on e.g. based on a model of the subject's smartphone. Where, in some embodiments, the adjustment is performed when the subject receives the add-on (e.g. by a health practitioner), and/or the subject themselves adjusts the add-on.

In some embodiments, adjustment includes aligning optical pathway/s of the add-on to one or more camera and or one or more illuminator of the smartphone. In some embodiments, aligning includes moving relative position of a proximal end of the add-on, and/or moving position of one or more portion of a proximal end of the add-on, for example, with respect to other portion/s of the add-on.

In some embodiments, customization includes selecting a suitable add-on. Where, for example, a kit includes a plurality of different add-ons suitable for use with different smart phones.

In some embodiments, customizing includes combining add-on portions. For example, in some embodiments, an add-on is customized by selecting a plurality of parts and connecting them together to provide an add-on. Where, in some embodiments, customization is of the parts and/or of how the parts are connected.

For example, in some embodiments, an add-on proximal portion is selected from a plurality of proximal portions for example, for connecting to a distal portion to provide an add-on for a subject. Where, in some embodiments, a single type distal portion is used e.g. refer to distal portions of add-ons illustrated in FIG. 22 and FIG. 23.

In some embodiments, customizing includes manufacture of the add-on e.g. for different smartphones. For example, an individually customized add-on e.g. for a specific user.

In some embodiments, portion/s of an add-on and/or a body of an add on are printed using a 3D printer e.g. in printed plastic.

In some embodiments, an add-on includes two or more parts. For example, in some embodiments, a part (e.g. portion 2422 FIG. 24, e.g. portion 2722 FIG. 27C) is manufactured using mass production methods (e.g. plastic injection molding) and a second part (e.g. portion 2420 FIG. 24, e.g. portion 2720 FIG. 27C) is customized for the user e.g. the user's smartphone. Where the second part, in some embodiments, is manufactured 3D printing.

For example, in an exemplary embodiment, a first portion of the add-on an elongate and/or distal portion of an add-on, including at least one mirror and, in some embodiments, at least one pattern projector. In some embodiments, a second portion of the add-on, includes optical element/s to align an imager of the smartphone to the optical path. Where, in some embodiments, the first portion is mass produced to be attached to the second portion which, in some embodiments, is customized for a user and/or smartphone model e.g. using 3D printing.

In some embodiments, an add-on is customized using subject data which is for example, received via a smartphone application. Where, in some embodiments, subject data includes one or more of; smartphone data and medical and/or personal records. For example, based on one or more of; a smartphone model, subject sex and/or age, the type of scanning to be performed. In some embodiments, the add-on is customized according to user personalization e.g. a user selects one or more personalization e.g. via a smartphone application. In some embodiments, optical elements e.g. mirror/s and/or lenses are the same for personalized add-ons e.g. potentially reducing a number of bill of materials (BOM) parts and/or simplifying manufacture and/or an assembly line for manufacture of personalized add-ons. Where assembly of a personalized add-on, in some embodiments, is by constructing (e.g. by 3D printing) an add-on body based on the user requirements and adding a same projector and/or mirror parts.

At 2104, in some embodiments, software is installed on a personal device (e.g. smartphone) to be used in dental scanning. For example, an application is downloaded onto the users smartphone.

In some embodiments, the software sends the smartphone model and/or feature/s including imager feature/s and/or illuminator feature/s (e.g. relative position, optical characteristic/s) of the smartphone and/or additional details (e.g. including one or more detail inputted by a user) are sent by the software to a customization center. Where, in some embodiments, an adaptor is customized according to the received details. For example, by 3D printing. In some embodiments, customized/s portions of an add-on are combined with standard portions to produce an add-on. Where, in some embodiments, the combining is performed at production or by the user who receives the parts separately and attaches them. Once customized the add-on and/or add-on is provided to the user.

In some embodiments, the application receives user inputs and/or outputs instructions to the user e.g. reminders to scan, instructions before and/or during scanning.

In some embodiments, the application interfaces with smartphone hardware to control imaging using one or more imager of the smartphone and/or illumination with one or more illuminator of the smartphone. Illuminators, in some embodiments, including the smartphone screen.

For example, in some embodiments, light transferred through the add-on optical path (e.g. through reflection at one or more mirrors) is incident on less than all of the pixels of a digital (e.g. CMOS) imager (e.g. of the smartphone). Or useful data is incident on less that all of the pixels. In some embodiments, imaging is confined to a ROI (Region of interest) where only the ROI is captured, and/or saved. Potentially enabling a higher frame rate (e.g. frames per second FPS) of imaging and/or a shorter scanning time.

At 2106, in some embodiments, the add-on is attached to the personal device (e.g. smartphone).

In some embodiments, add-on is mechanically attached to smartphone using a case which surrounds the smartphone, at least partially. Where, in some embodiments, the add-on includes a case e.g. has a hollow into which the smartphone is placed to attach the smartphone to the add-on. Where exemplary embodiments are illustrated, for example, in FIG. 10A, FIG. 10B, FIG. 10C, FIG. 11B, FIG. 11C.

In some embodiments, add-on is attached mechanically to a face of the smartphone (E.g. to back face opposite a face including the smartphone scree). In some embodiments, the add-on surrounds one or more optical element of the smartphone.

In some embodiments, attachment is sufficiently rigid and/or static to hold smartphone optical element/s and optical pathways of the add-on in alignment.

In some embodiments, a user is provided with feedback as to the quality of attachment of the add-on to the cell phone. Where, in some embodiments, the user is instructed to reposition the add-on.

In some embodiments, for example, where the add-on only transfers imager FOVs e.g. as single imager FOV, aligning includes aligning and attaching the add on to this optical element e.g. only.

At 2018, in some embodiments, add-on is calibrated e.g. once it is attached to a smartphone. For example, in some embodiments, the add-on attached to the smartphone is calibrated by using a calibration jig, for example, by placing onto and/or into calibration cradle 1802 FIG. 18A. For example, after attachment of the add-on to the smartphone and for example, prior to imaging and/or during imaging.

Figure 18A:
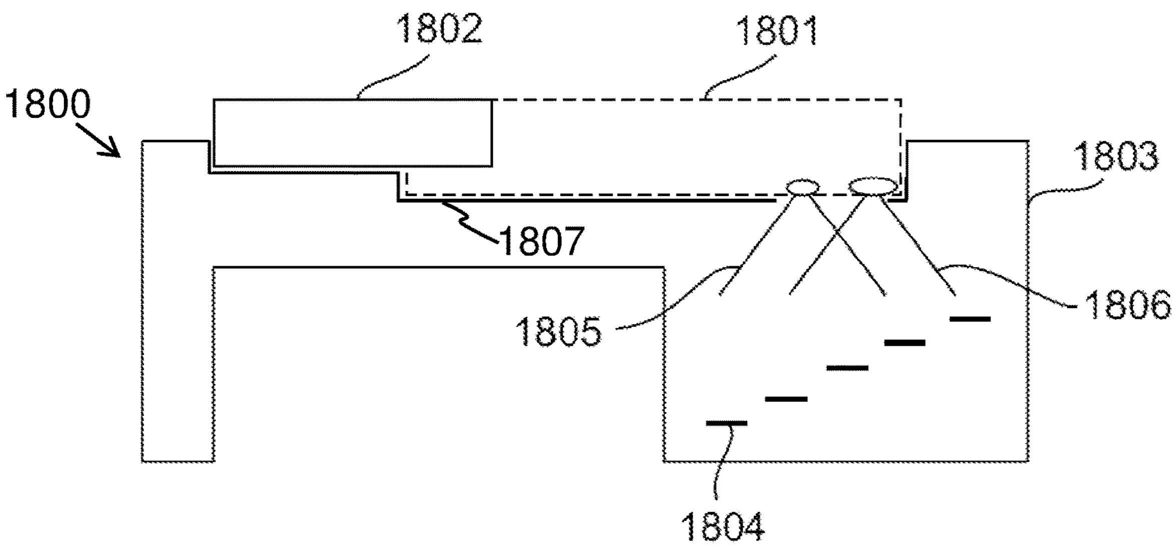
FIG. 18A is a simplified schematic of a calibration cradle 1800 holding an add-on 1801 connected to a smartphone 1802, according to some embodiments of the invention.
Figure 18B:
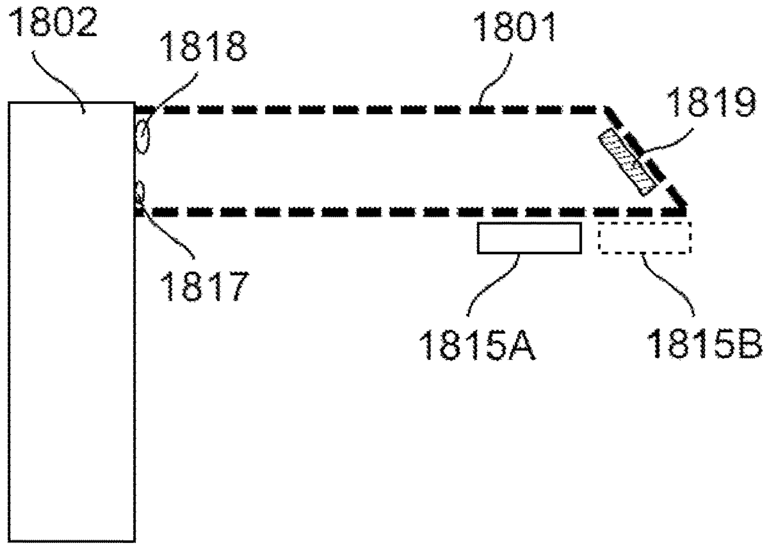
FIG. 18B is a simplified schematic of an add-on 1801 attached to a smartphone 1802, according to some embodiments of the invention.

In some embodiments, a calibration element 1815B FIG. 18B is used.

In some embodiments, internal feature/s of the add-on are used to calibrate the add-on.

For example, in some embodiments, smartphone camera focus adjusted for by adjusting software parameter/s of the smartphone by fixing the camera focus using an high contrast target (e.g. a face e.g. a simplified face icon) inside the add-on positioned so that target is imaged by the camera without blocking dental images. Where, in some embodiments, the target allows adjustment of camera focus periodically and/or continuously and/or during scanning.

In some embodiments, calibration includes acquiring one or more image, including a known feature, for example, of a known size and/or shape and/or distance away, and/or color. In some embodiments, a known feature includes internal feature/s of the add-on e.g. as appearing in acquired images through the add-on.

In some embodiments, a known size object when captured in an imager (e.g. by CMOS in pixels) enables an imaged object to pixel. In some embodiments, a known shape enables calibration of tiling (e.g. of the add-on with respect to smartphone optics), for example, by identifying and/or quantifying distortion of a collected image of a known shape.

At 2110, optionally, in some embodiments, one or more fiducial is attached to the subject.

Figure 22:
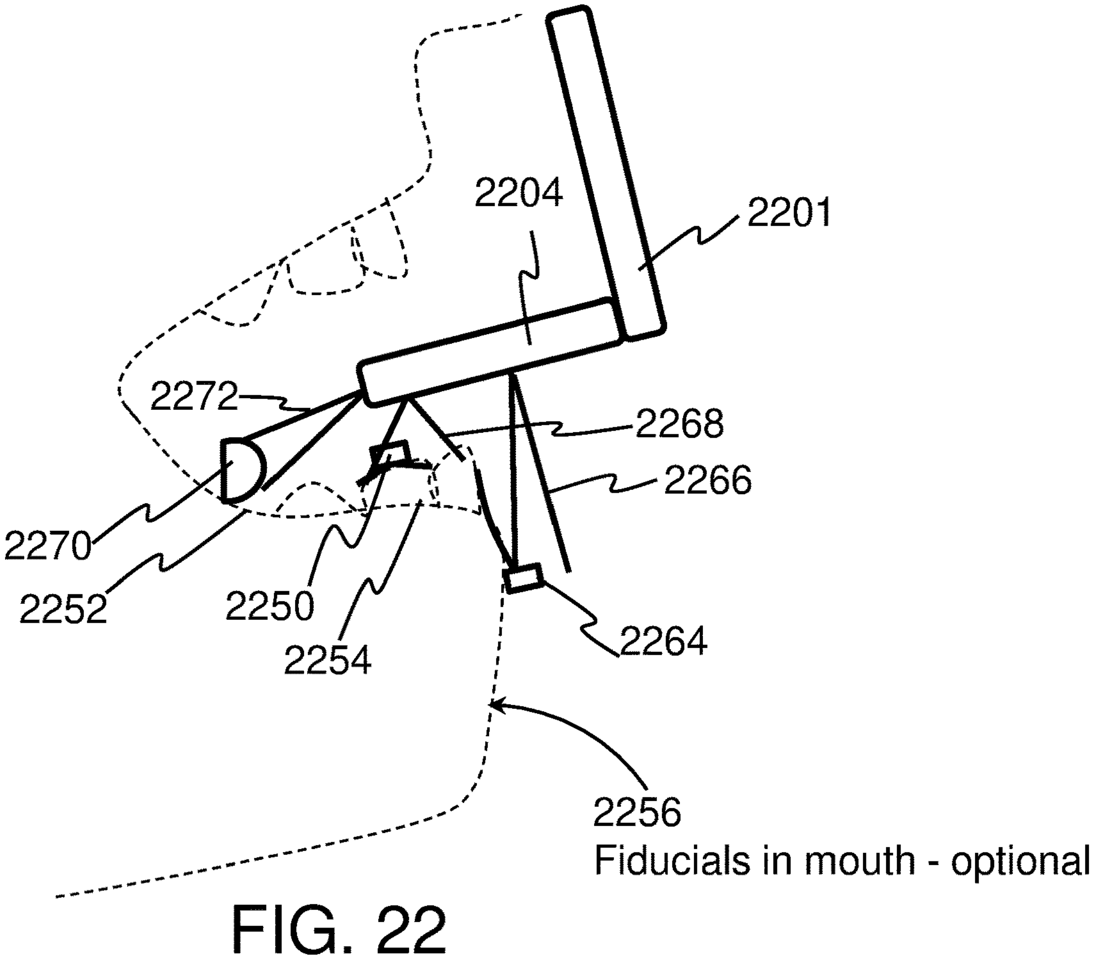
FIG. 22 is a simplified schematic illustrating scanning of a subject using an add-on attached to a smartphone, according to some embodiments of the invention.
Figure 23:
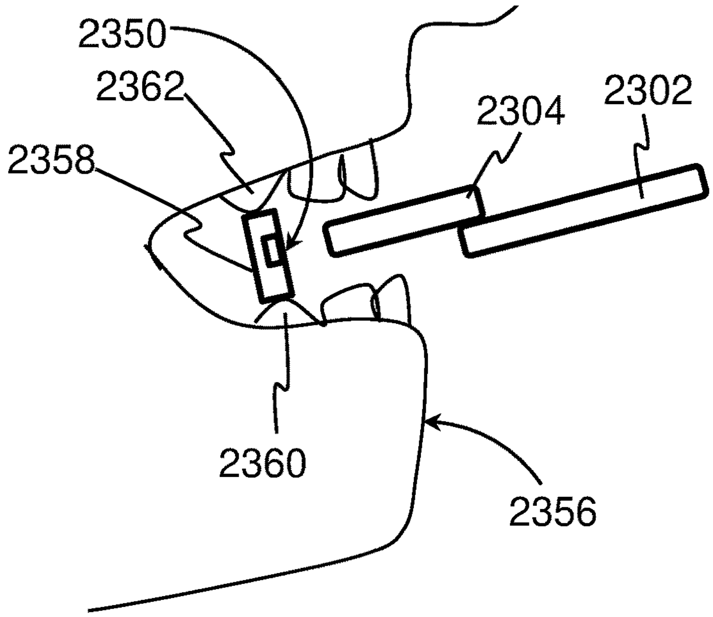
FIG. 23 is a simplified schematic illustrating scanning of a subject using an add-on attached to a smartphone, according to some embodiments of the invention.

At 2112, optionally, one or more mirror is attached to the subject.

Where attachment at step 2110 and/or step 2112 includes, in some embodiments, one or more feature as illustrated in and/or described regarding FIG. 22 and/or FIG. 23.

In some embodiments, attachment of fiducial/s and/or mirror/s is by positioning a cheek retractor (e.g. by the user), for example, as described in one or more of FIGS. 19A-H. In some embodiments, a cheek retractor which does not include fiducial/s and/or mirrors is attached e.g. by the user.

In some embodiments, the subject bites down one or more biter of the cheek retractor. For example, to hold the cheek retractor in a known position with respect to dental feature/s. In some embodiments, one or more back side cheek retractor is positioned. In some embodiments, a cheek retractor and back side cheek retractor are a single connected element.

At 2114, in some embodiments, the mouth is scanned using the add-on attached to the smartphone.

In some embodiments, the add-on is inserted into the mouth and moved around within the mouth while collecting images. For example, in some embodiments, a user moves the add-on within the mouth using movement along dental arch/es that are generally used during tooth brushing.

In some embodiments, the user does not view the screen of the smartphone during scanning. Optionally, the user receives aural feedback broadcast by the smartphone during scanning. In some embodiments, the user views the smartphone screen after scanning to receive feedback about the quality of the scan, for example, direction to scan particular areas which were e.g. insufficiently scanned or not scanned.

In some embodiments, the add-on is not inserted into the mouth and images outside surfaces of teeth directly and, in some embodiments, images internal surfaces e.g. lingual surface/s of teeth via reflections onto mirror/s.

In some embodiments, internal mirror/s have fixed position with respect to dental feature/s and/or fiducials. For example, as described regarding FIGS. 19A-F and/or FIG. 22 and/or FIG. 23.

In some embodiments, scanning includes collected images of dental features illuminated, for example, with patterned optical light.

In some embodiments, illumination is without patterned light (e.g. using ambient illumination and/or non-patterned artificial illumination).

In some embodiments, scanning includes fluorescence measurement/s are collected, by illuminating dental feature/s (e.g. teeth) with UV light and acquiring visible and/or IR light reflected by the features. For example, in some embodiments, incident UV light incident on dental features causes green fluorescence for enamel regions and red fluorescence indicating presence of bacteria. Where, in some embodiments, the add-on includes one or more UV illuminator for projection of UV light onto dental feature/s.

In some embodiments, scanning includes tomography, for example, illuminating dental feature/s (e.g. teeth) with near infrared light (NIR). With a wavelength of, for example, 700-900 nm, or about 780 nm, or about 850 nm, or lower or higher or intermediate wavelengths or ranges. Where, in some embodiments, the add-on includes one or more NIR LED or LD (laser diode). In some embodiments, reflected NIR light images are used to detect caries inside the tooth, for example inside the enamel in the interproximal areas between two teeth.

In some embodiments, the smartphone imager focal distance is adjusted for acquisition of patterned light incident onto dental feature/s. In some embodiments, resolution and/or compression of images acquired is selected to maximize data within images including patterned light.

In some embodiments, during scanning the smartphone imager focus is scanned over a plurality of focus distances, for example, over 2-10, or 2-5, or three different focus distances. For example, where focal distances range from 50-500 nm, where, in some embodiments, three exemplar focal distances are 100 mm, 110 mm, 120 mm. In some embodiments, focal distances are selected based on a distance between the add-on and dental features to be scanned.

Where, in some embodiments, software installed on the smartphone controls the smartphone imager during scanning to provide different focal distances.

In some embodiments, a first imager is used to image outside the mouth e.g. outer surface/s of teeth during scanning inside the mouth e.g. by a second imager or imagers. Where, in some embodiments, the first imager is a smartphone imager directly acquiring images and the second imager FOV is transferred by the add-on. In some embodiments, the first imager is a wide angel imager, and the second imager is a narrow angle imager. In some embodiments, images collected by the first image are used to increase the accuracy of a 3D model of a plurality of teeth in a jaw (e.g. a full jaw). For example, in some embodiments, images collected using the first imager capture larger regions e.g. of external dental features and these images are used to correct accumulated error/s in scanning along a jaw. Where the accumulated errors, in some embodiments, are associated with the narrow FOV of the second imager and/or movement during imaging.

In some embodiments, software downloaded on the smartphone (e.g. at step 2104) controls illuminators of the smartphone during scanning. For example, switching illuminators (e.g. LED illuminator/s e.g. via LED chips). Where, in some embodiments, switching is between patterned illumination and un-patterned illumination. Images including patterned light incident on dental features, for example, being used to generate model/s (e.g. 3D model/s) of the dental features and un-patterned light providing color and/or texture measurement of the dental features.

In some embodiments, scanning includes collection of images with a single imager and/or a single FOV. In some embodiments, multiple imagers and/or multiple FOVs are used. Where, in some embodiments, a FOV of a single imager is split into more than one FOV. In some embodiments, imaging is via one or more FOV emanating from an add-on and optionally, in some embodiments, directly via a smartphone imager. Where, FOVs emanating from the add-on include, in some embodiments, smartphone imager FOV transferred through the add-on and/or FOV of imager/s of the add-on.

In some embodiments, multiple images are collected simultaneously e.g. by different imagers. In some embodiments, images from different directions (e.g. FIG. 4B, FIGS. 5A-C) with respect to the add-on and/or smartphone are collected e.g. simultaneously.

At 2116, in some embodiments, a user is guided in scanning, for example before during and/or after scanning, e.g. by user interface/s of the smartphone. Where, in some embodiments, guiding includes aural clues. Where, in some embodiments, the user views images displayed on the smartphone directly or via reflection in one or more mirror. Where, in some embodiments, the reflection is in a mirror of the add on (e.g. mirror 1102A, 1102B FIG. 11A). Where, in some embodiments, the reflection is in an external mirror e.g. mirror 1142 FIG. 11D.

In some embodiments, for example, when the smartphone has a screen on his back side, or when, during scanning the smartphone screen is facing the user (e.g. imaging is via an imager on a front face of the smartphone) a user directly views the smartphone screen (or a portion of the screen) during scanning.

At 2118, in some embodiments, scanning data is evaluated.

In some embodiments, evaluation of data includes generating model/s of dental features using collected images. For example, 3D models.

In some embodiments, imaged deformation of structured light incident on 3D structures is used to re-construction 3D feature/s of the structures. For example, based on calibration of deformation the structured light.

In some embodiments, for example, where patterned light is not used SFM (structure from motion) technique/s and/or deep learning networks are used to generate 3D model/s from acquired 2D images and optionally the IMU sensor data.

In some embodiments, scan data is evaluated to provide measurement or and/or indicate change/s in one or more of degree of misalignment of the teeth, the shade or color of each tooth surface, how clean is the area between metal orthodontic braces, what is the degree of plaque and/or tartar (dental calculus) is on one or more tooth surface, detecting caries (dental decay, cavities) on and/or inside the teeth and/or their location on a 3D model, detecting tumors and/or malignancies and/or their location on the 3D model.

At 2120, in some embodiments, a healthcare professional receives the data evaluation and, in some embodiments, responds to the data evaluation. For example, indicating that the subject should perform an action, for example, book an in-person appointment. For example, changing a treatment plan.

At 2122, in some embodiments, communication to the user is performed e.g. via the smartphone. For example, instructions from the healthcare professional. For example, to perform one or more of; aligning the teeth (e.g. use aligners), whiten the teeth, brush between orthodontic braces, brush a specific tooth (e.g. with a lot of plaque), set appointment for tartar (dental calculus) removal, set a dentist, X-ray, or physical test appointment.

Additional Exemplary Add-On Embodiments

Figure 2C:
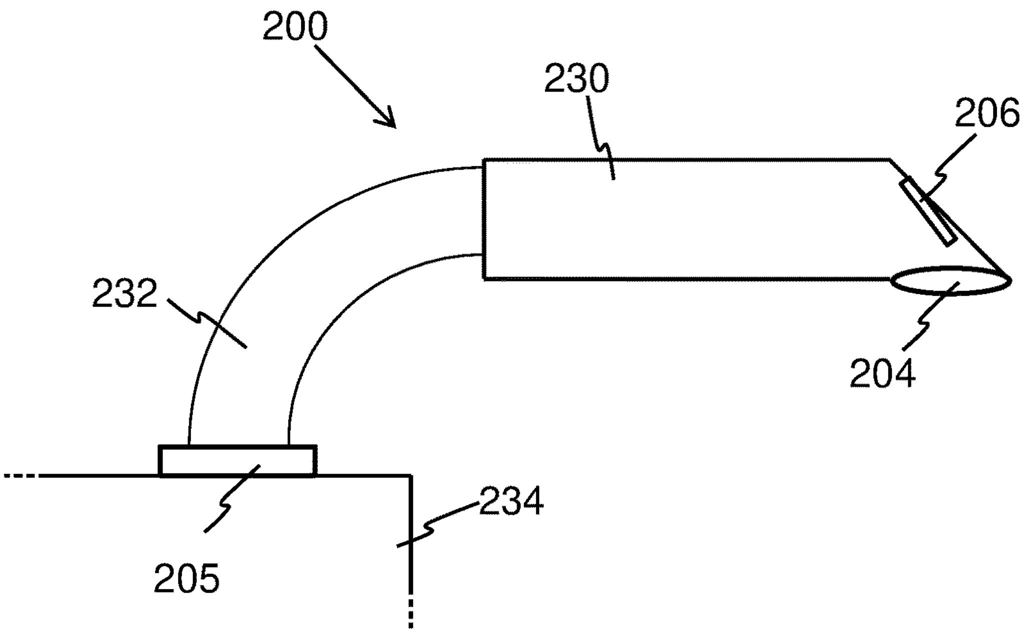
FIG. 2C is a simplified schematic of an add-on connected to a smartphone, according to some embodiments of the invention.

FIG. 2C is a simplified schematic of an add-on 200 connected to a smartphone 234, according to some embodiments of the invention. In some embodiments, add-on 201 includes a body 230. In some embodiments, add-on 200 includes one or more feature of add-on 104 FIG. 1 and/or add-on 201 FIG. 2A.

In some embodiments, add-on 200 provides an optical path to and/or from smartphone 234. For example, for a camera and/or illuminator 205. In some embodiments, at least a portion of the optical path is provided by optical fibers 232.

For example, a portion of the optical path as illustrated in FIG. 2C where light is also transferred by a mirror 206.

In some embodiments, optical fibers 232 extend through add-on body 230, add-on in some embodiments, not including a mirror. In some embodiments, optical fibers 232, (for example, an optical fiber bundle where each pixel of camera 202 receives light via an optical fiber e.g. a coherent optical fibers bundle are used to transfer the FOV of the imager) are used to transfer light captured at a distal end of the add on (e.g. by a lens 204 located at a distal end of the add-on) to camera 205. Optionally, in some embodiments, add-on includes one or more additional lenses e.g. to change a focal distance of FOV, for example, to adjust the focal distance to be suitable for dental imaging.

In some embodiments, optical fiber/s 232 transfer light from a LED 205 to a pattern projector (not illustrated in FIG. 2C) which e.g. includes a projection lens.

In some embodiments, connection 232 and/or add-on 200 is partially and/or fully made of flexible and/or non-rigid materials. Potentially, flexibility of connection 232 and/or add-on body 230 enables movement of the add-on in the mouth relative to smartphone 234 which, in some embodiments, is static (e.g. on a surface e.g. laying on a table) during scanning. In some embodiments, position between add-on optics e.g. one or more lens 204 and/or mirror 206 is kept rigid.

Figure 3:
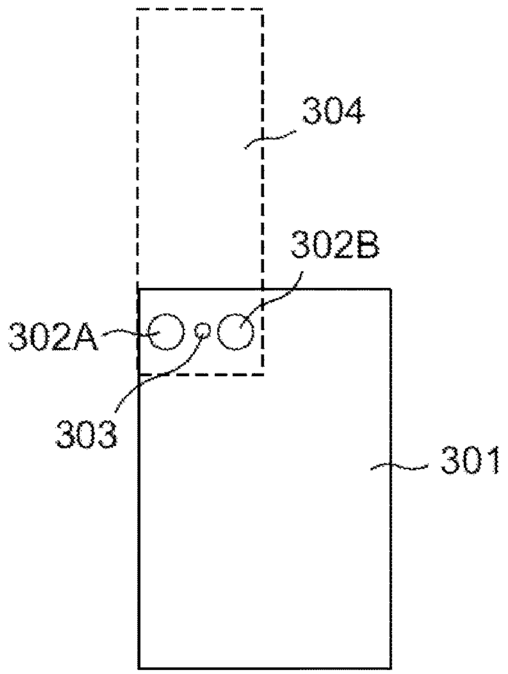
FIG. 3 is a simplified schematic of an add-on 304 connected to a smartphone including multiple cameras, according to some embodiments of the invention.

FIG. 3 is a simplified schematic of an add-on 304 connected to a smartphone 301 including multiple cameras 302A, 302B, according to some embodiments of the invention.

In some embodiments, add-on 304 includes one or more feature of one or more of add-on 104 FIG. 1, add-on 201 FIG. 2A, and add-on 200 FIG. 2C.

In some embodiments, smartphone 301 includes an illuminator 303, which in some embodiments, includes a flash LED. In some embodiments, add-on 304 transfers illuminator light e.g. through a body of add-on 304.

In some embodiments, add-on 304 transfers FOVs of both cameras 302A, 302B e.g. through a body of the add-on. In some embodiments, FOVs of cameras 302A, 302B, at least after transfer through add-on, have different characteristics e.g. different direction and/or resolutions.

Figure 4A:
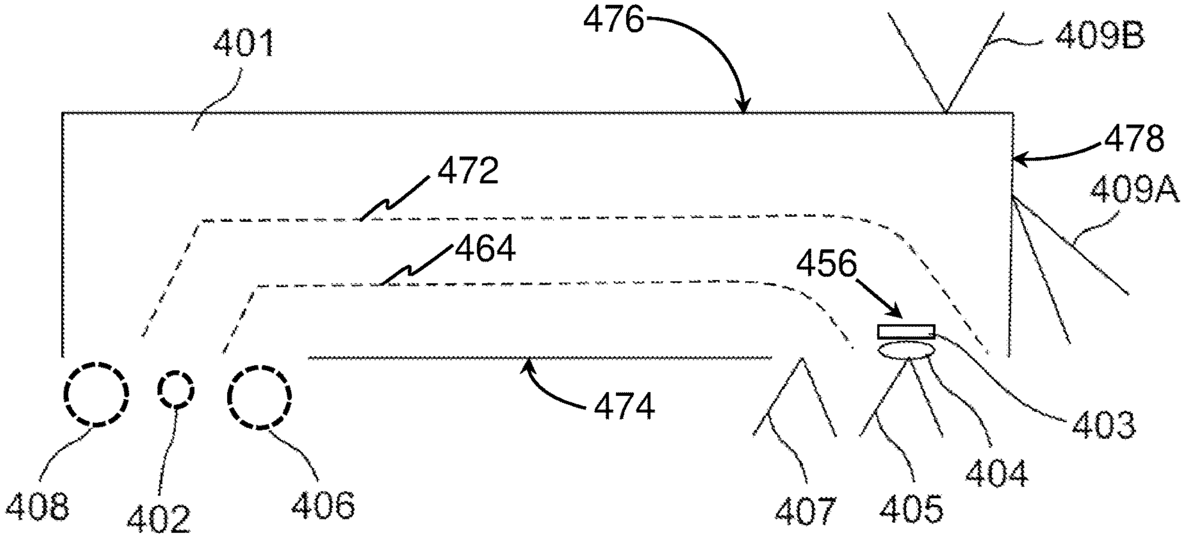
FIG. 4A is a simplified schematic cross section of an add-on for a multiple camera smartphone, according to some embodiments of the invention.

FIG. 4A is a simplified schematic cross section of an add-on 401 for a multiple camera 406, 408 smartphone, according to some embodiments of the invention.

In some embodiments, add-on 401 includes one or more feature of one or more of add-on 104 FIG. 1, add-on 201 FIG. 2A, add-on 200 FIG. 2C, and add-on 304 FIG. 3.

In some embodiments, a FOV 407 of a first camera 406 is transferred by add-on 401 and a FOV of a second camera 408 is transferred by add-on to FOV 409B and/or FOV 409A. In some embodiments, a FOV of an illuminator is transferred by add-on to FOV 405.

FIG. 4A illustrates both transfer of first camera 406 FOV and illuminator 402 FOV to directions opposite (or about opposite) direction of emanation of the FOVs from the smartphone. FIG. 4A also illustrates transfer of second camera 408 FOV to the a direction of less than 90 degrees of FOVs 407 and 405 and/or a direction opposite 409B e.g. about 180 degrees to FOVs 407, 405. However, it should be understood that the embodiment illustrated in FIG. 4A is an exemplary embodiment, and in some embodiments, multi-camera smartphones have FOVs of the camera/s and/or illuminators transferred to any of the directions illustrated regarding and/or described in FIG. 4B.

In some embodiments the transfer of one or more FOV through add-on 401 is by folding the FOV e.g. with one or more mirror (e.g. including one or more feature as described regarding transfer and/or mirrors 206*a*, 206*b* FIG. 2A).

In some embodiments, light illuminated from illuminator 402 is patterned and/or focused, for example, by passing through a projector 456 which includes, in some embodiments, a pattern 403 and/or lens 404 (e.g. including one or more feature as illustrated and/or described regarding projector 256 in FIG. 2A).

In some embodiments, projected light FOV 405 and camera 406 FOV 407 to capture illuminated dental feature/s (e.g. one or more tooth) while, in some embodiments, one or more FOV 409A and/or FOV 409B captures at least one of: an adjacent tooth on the same arc, a tooth on the antagonist (and/or opposite) jaw, a tooth on the far end (e.g. distal portion) of the jaw, and a tooth on the other side of the same arch.

Figure 5A:
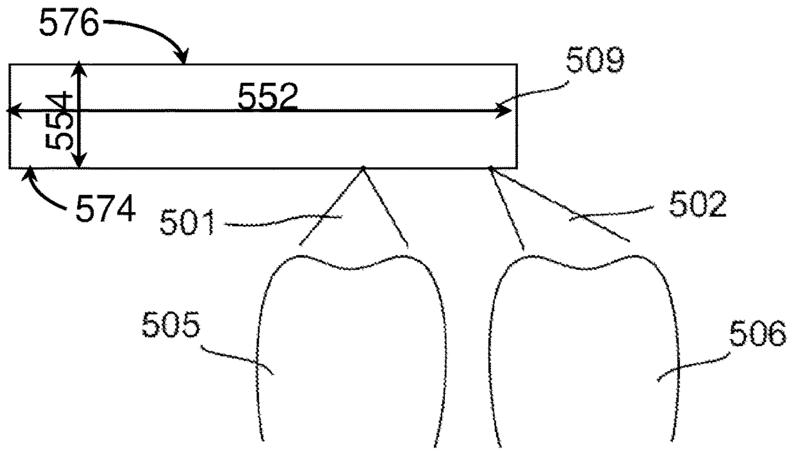
FIG. 5A is a simplified schematic side view of an add-on and scanning objects, according to some embodiments of the invention.

In some embodiments, where second camera 408 collects image/s of an adjacent tooth (e.g. to that imaged by first camera and FOV 407). For example, as illustrated in FIG. 5A. For example, in some embodiments, the FOV of second camera 408 is projected forward and downwards e.g. as illustrated by FOV 409A.

Figure 5B:
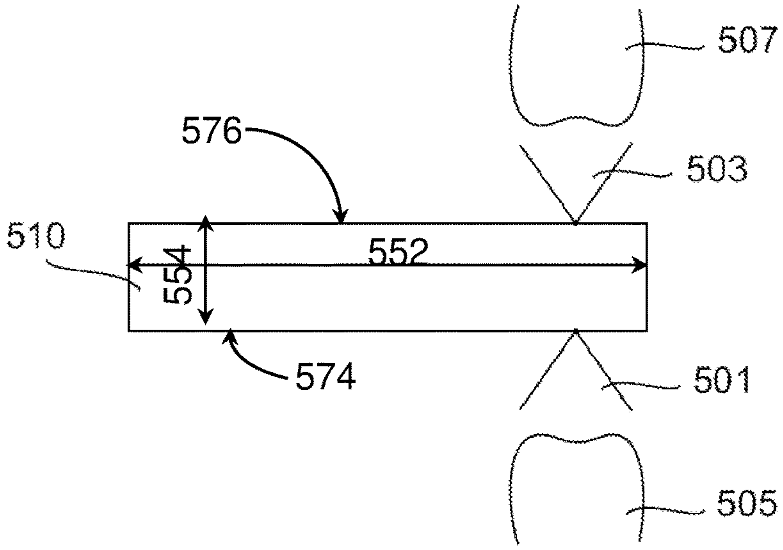
FIG. 5B is a simplified schematic of an add-on with respect to dental features, according to some embodiments of the invention.

In some embodiments, second camera 408 collects image/s of an antagonist jaw and/or dental feature/s of the antagonist jaw (e.g. one or more tooth) the second camera FOV is projected upwards e.g. as illustrated by FOV 409B. For example, as illustrated in FIG. 5B.

Figure 5C:
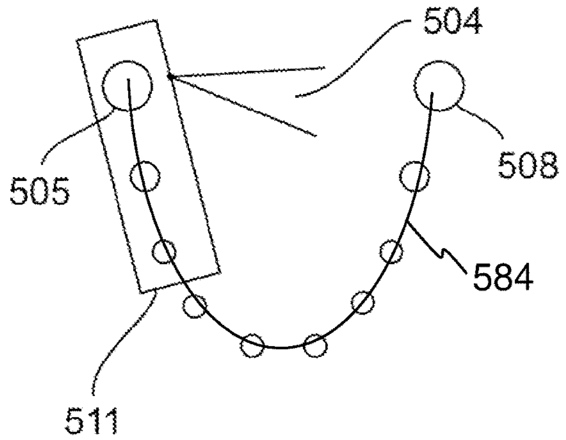
FIG. 5C is a simplified schematic of an add-on with respect to dental features, according to some embodiments of the invention.

In some embodiments, second camera 408 collects image/s of a far end of the jaw imaged by FOV 407, second camera FOV is projected in directions perpendicular to a plane of the illustration of FIG. 4A. For example, as illustrated in FIG. 5C.

Figure 4B:
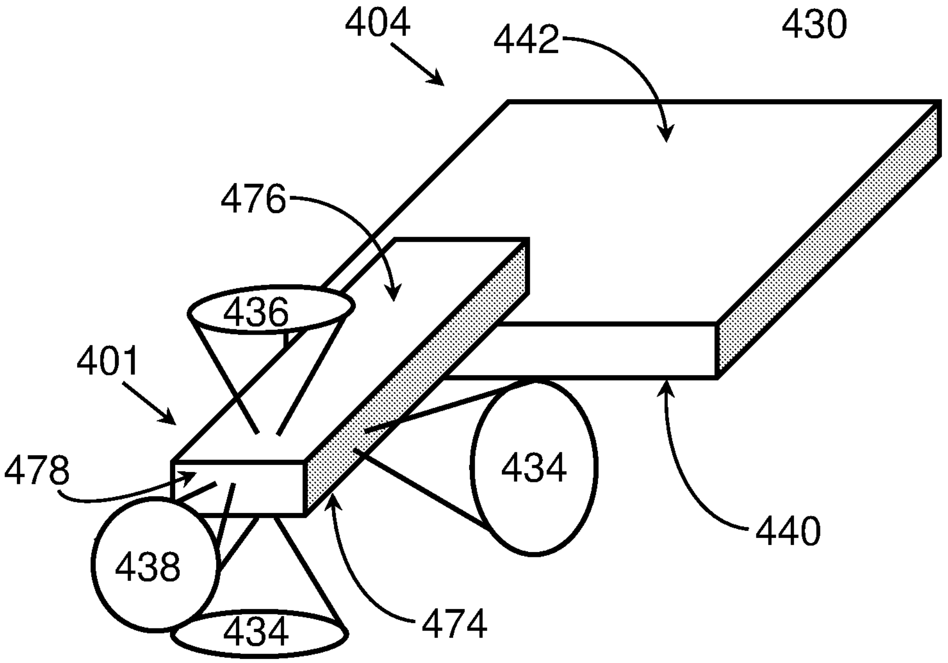
FIG. 4B is a simplified schematic of an add-on connected to a smartphone, according to some embodiments of the invention.

FIG. 4B is a simplified schematic of an add-on 401 connected to a smartphone 404, according to some embodiments of the invention.

In some embodiments, smartphone 404 has a first face 440 and a second face 442. Where, in some embodiments, first face 440 hosts the smartphone screen and optionally one or more camera and second face 442, in some embodiments hosts at least one camera an optionally one or more illuminator.

In some embodiments, add-on moves one or more FOV of one or more optical component of smartphone 404 e.g. of one or more camera and/or one or more illuminator.

In some embodiments, FOV/s of optical component/s are transferred from extending from a portion of second face 442 to one or more of FOVs 434, 436, 438, 444. Where, in some embodiments, a FOV is transferred laterally (e.g. only transferred laterally e.g. FOV 436) and/or rotated in one or more direction, for example, by about 180 degrees e.g. FOV 434 and/or rotated by about 90 degrees e.g. FOV 434, 438.

In some embodiments, one or more transferred FOV extends from a first face 474 of add-on e.g. FOV 434. In some embodiments, one or more transferred FOV extends from a second face 476 of add-on e.g. FOV 436. In some embodiments, one or more transferred FOV extends from one or more side of add-on 401 e.g. FOVs 438, 434. For example, a side of add-on which is about perpendicular to one or more face of add-on and/or smartphone. For example, a distal side 478 of add-on.

FIG. 5A is a simplified schematic side view of an add-on 509 and scanning objects 505, 506, according to some embodiments of the invention.

FIG. 5A, in some embodiments, illustrates scanning of adjacent objects, dental features, e.g. teeth 505, 506. Where, in some embodiments, one or both of objects 505, 506 are dental feature/s e.g. teeth.

In some embodiments, add-on transfers more than one imaging FOV 501, 502, where more than one FOV 501, 502 are in a same direction e.g. with respect to a body of add-on 509. Where, in some embodiments, FOVs 501, 502 enable concurrent image collection of adjacent regions e.g. adjacent teeth. For example, in some embodiments, an add-on transfers a first imaging FOV 501 and a second imaging FOV 502 where both FOVs 501, 502 extend from a lower face 574 of add-on. In some embodiments, FOVs 501, 502 are each a transferred FOV of a different smartphone camera. In some embodiments, FOVs 501, 502 are split FOVs of a single smartphone camera.

FIG. 5B is a simplified schematic of an add-on 510 with respect to dental features, according to some embodiments of the invention.

show a side view of the case of upper FOV 503 that allows an add-on 510 to scan the antagonist tooth 507 on the opposite jaw while scanning a tooth 505 with the first FOV 501.

FIG. 5C is a simplified schematic of an add-on 511 with respect to dental features, according to some embodiments of the invention.

In some embodiments, add-on 511 transfers a FOV (or portion of a FOV) of an imager of a smartphone (not illustrated) laterally, for example, with respect to a long axis of the add-on e.g. to image an opposite half of a jaw 584 than that imaged by one or more other FOV of the smartphone. In some embodiments, dental feature (e.g. tooth) 505 is imaged concurrently to dental features 508 on an opposite side of jaw 584 (e.g. imaged by FOV 504).

In some embodiments, alternative or additionally scanning directions and/or FOV/s are envisioned and/or encompassed. For example, in some embodiments, where a first FOV is scanning a first tooth, a FOV is adjusted to scan two teeth along from the first tooth within the same jaw, and/or a FOV is adjusted to scan an antagonist tooth that is not immediately opposite the first tooth.

In some embodiments, imaging and/or illumination is with more than two FOV, for example 3, 4, 5, 6 or higher. Where each FOV, in some embodiments, corresponds to a smartphone imager FOV or a portion of a smartphone imager FOV.

Figure 6A:
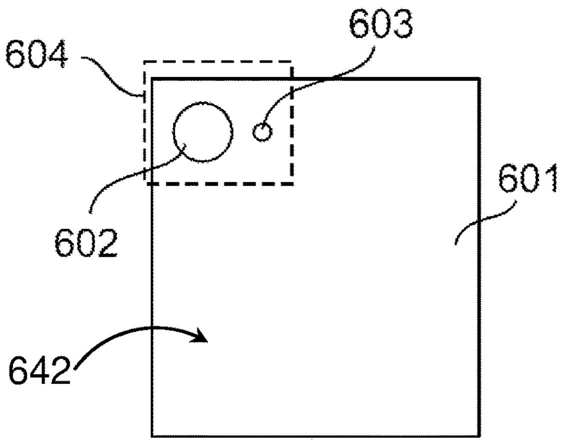
FIG. 6A is a simplified schematic of an add-on connected to a smartphone, according to some embodiments of the invention.

FIG. 6A is a simplified schematic of an add-on 604 connected to a smartphone 601, according to some embodiments of the invention.

In some embodiments, add-on 604 is mounted on top of smartphone 601. In some embodiments, smartphone includes at least one camera 602 and at least one illuminator 603 (e.g. including a flash LED).

In some embodiments, add-on does not extend more than 0.5-1 cm from smartphone 601 in one or more direction. For example, at least directions parallel to a plane second face 642 of the smartphone (where, second face 642, in some embodiments, has one or more feature as illustrated and/or described regarding second face 442 FIG. 4B).

Figure 6B:
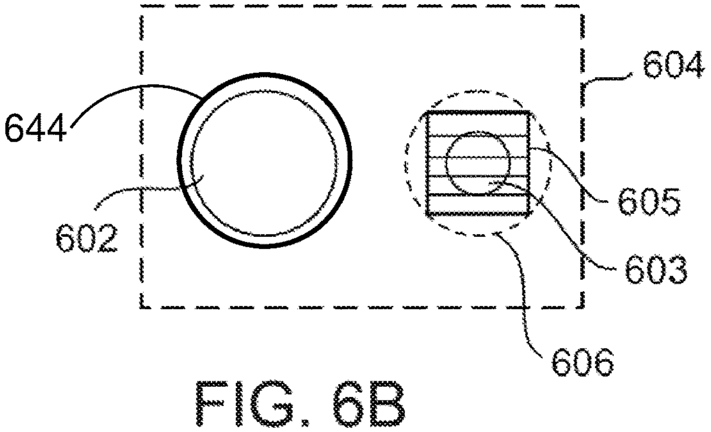
FIG. 6B is a simplified schematic of an add-on, according to some embodiments of the invention.

FIG. 6B is a simplified schematic of an add-on 604, according to some embodiments of the invention.

In some embodiments, add-on 604 includes an optical pattern 605 and, optionally, a projection lens 606. Where, in some embodiments, optical pattern and/or lens 606 are mounted in front of an illuminator 603 (e.g. flash LED) of a smartphone.

In some embodiments, add-on 604 includes one or more lens 644 to adjust a FOV of smartphone camera 602, where, in some embodiments, lens 644 is positioned in front of the smartphone camera 602. In some embodiments, lens 644 adjusts depth of focus and/or focal distance and/or FOV of the smartphone camera for dental scanning e.g. of the teeth. In some embodiments, the smartphone camera FOV is reduced in size and/or a portion of the FOV is used, for example, to capture small regions e.g. within the mouth.

Figure 6C:
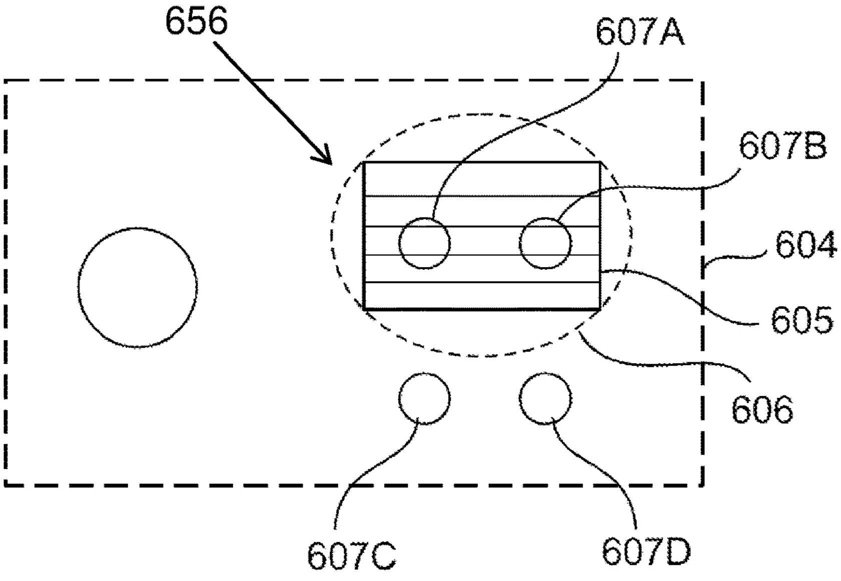
FIG. 6C is a simplified schematic of an add-on attached to a smartphone, according to some embodiments of the invention.

FIG. 6C is a simplified schematic of an add-on 604 attached to a smartphone, according to some embodiments of the invention.

In some embodiments, the smartphone includes a plurality of illuminators 607A, 607B, 607C, 607D. Where, in some embodiments, one or more of the illuminators (e.g. each illuminator) includes a LED chip.

In some embodiments, add-on 604 includes a projector 656, where less than all of the smartphone illuminators are optically coupled to projector 656. Where, in some embodiments, projector 656 includes one or more pattern 605 and/or one or more lens 606.

For example, in some embodiments projector 656 it is optically coupled to (e.g. mounted above, when add-on is attached to the smartphone) two LED chips 607A and 607B e.g. out of a total of four LED chips 607A, 607B, 607C, 607D.

For example, in some embodiments projector 656 is optically coupled to one out of two LED chips, where the smartphone (e.g. smartphone chip) includes two LED chips.

Figure 7A:
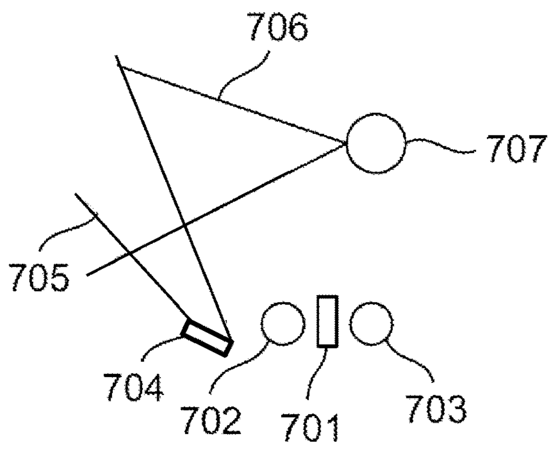
FIG. 7A is a simplified schematic of optical path components with respect to an imager and an illuminator, according to some embodiments of the invention.

FIG. 7A is a simplified schematic of optical path components 704, 702, 701, with respect to an imager 707 and an illuminator 703, according to some embodiments of the invention.

In some embodiments, a FOV 707 of an imager (e.g. smartphone imager) is aligned to overlap with a FOV 705 of an illuminator (e.g. smartphone illuminator). Where, in some embodiments, a direction of illuminator FOV 705 is aligned using one or more mirror 704. In some embodiments, light emitted by illuminator 703, is patterned by one or more pattern 701 and/or adjusted (e.g. focused) by one or more lens 702 for example, prior to being deflected by mirror 704. In some embodiments, one or more of mirror 704, pattern 701 and lens 702 are hosted by an add-on. The add-on, for example, including one or more features as described and/or illustrated elsewhere in this document.

In some embodiments, an angle of mirror 704 e.g. with respect to FOV 706 is selected so that imaging FOV 706 and illumination FOV 705 overlap at dental imaging distance/s. For example, so that collected images of dental features will have the features illuminated by the illumination FOV.

Where, in some embodiments, dental imaging distance/s, as measured from the imager 707 and/or illuminator 704 and/or from a body of an add-on from which the FOVs emanate, is 20-80 mm, or 40-60 mm, or about 40 mm, or about 50 mm, or about 60 mm or longer or shorter or intermediate ranges or distances. In some embodiments, for example, in addition or alternatively to mirror 704, a prism is used to align projection FOV 704 towards camera FOV 706.

Figure 7B:
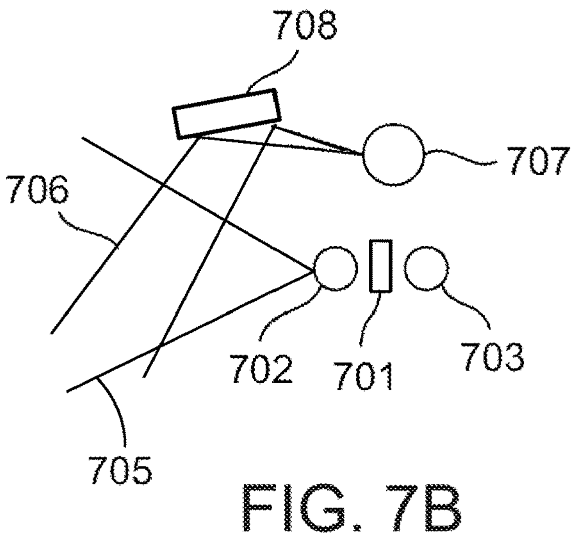
FIG. 7B is a simplified schematic of optical path components, with respect to an imager and an illuminator, according to some embodiments of the invention.

FIG. 7B is a simplified schematic of optical path components 701, 702, 708, with respect to an imager 707 and an illuminator 703, according to some embodiments of the invention.

In some embodiments, a FOV 706 of an imager (e.g. smartphone imager) is aligned to overlap with a FOV 705 of an illuminator (e.g. smartphone illuminator). Where, in some embodiments, a direction of imager FOV 706 is aligned using one or more mirror 708. In some embodiments, light emitted by illuminator 703, is patterned by one or more pattern 701 and/or adjusted (e.g. focused) by one or more lens 702. In some embodiments, one or more of mirror 704, pattern 701 and lens 702 are hosted by an add-on. The add-on, for example, including one or more features as described and/or illustrated elsewhere in this document.

In some embodiments, an angle of mirror 708 e.g. with respect to FOV 705 is selected so that imaging FOV 706 and illumination FOV 705 overlap at dental imaging distance/s. For example, so that collected images of dental features will have the features illuminated by the illumination FOV.

Where, in some embodiments, the distance is 20-80 mm, or 40-60 mm, or about 40 mm, or about 50 mm, or about 60 mm or longer or shorter or intermediate ranges or distances. In some embodiments, for example, in addition or alternatively to mirror 708, a prism is used to align projection FOV 705 towards camera FOV 706.

In some embodiments, the add-on includes a mirror (and/or prism) in front of both the camera and the pattern projection lens. Where, in some embodiments, the mirrors adjust both the FOV of the camera and that of the projector.

Figure 7C:
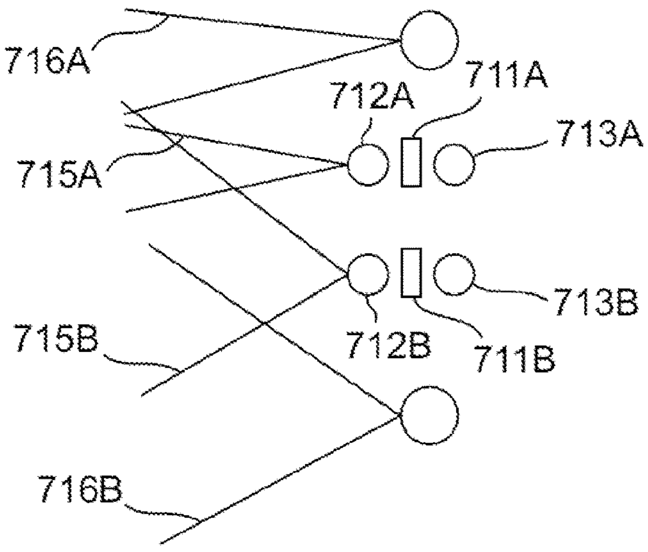
FIG. 7C is a is a simplified schematic of optical path components with respect to multiple imagers and/or illuminators, according to some embodiments of the invention.

FIG. 7C is a simplified schematic of optical path components with respect to multiple imagers and/or illuminators 713A, 713B, according to some embodiments of the invention.

In some embodiments, a first imager has a first FOV 716A, a second imager has a second FOV 716B. In some embodiments, a smartphone hosts the imagers and/or illuminators 713A, 712B. For example, smartphone 301 FIG. 3 has multiple optical components 302A, 302B, 303.

In some embodiments, FOV of one or more component, e.g. one or more component of a smartphone is adjusted, for example, according to (e.g. to match) the FOV of the component to another FOV. For example, a FOV of a corresponding component. For example, in some embodiments, a FOV is adjusted to give an illuminator FOV a similar extent and/or direction and/or to overlap with a FOV of an imager collecting images of object/s illuminated by the illuminator.

For example, in some embodiments, imager FOV 716A and illuminator FOV 713A both have narrow FOVs. For example, in some embodiments, lens 712A adjusts (e.g. narrows) a FOV of illuminator 713A based on FOV 716A of camera 711A. For example, in some embodiments, imager FOV 716B and illuminator FOV 713B both have wide FOVs. For example, in some embodiments, lens 712B adjusts (e.g. widens) a FOV of illuminator 713B based on FOV 716B of camera 711B.

In some embodiments, illuminator light is patterned by patterns 711A, 711B e.g. prior to focusing by lenses 712A, 712B.

In some embodiments, projector FOVs 715A, 715B overlap. In some embodiments, illuminator/s 713A, 714A are switched, for example, so that only a single pattern is projected into a FOV of a camera collecting an image.

For example, where, in some embodiments, switching of the projector illuminators is synchronized with image acquisition. For example, illuminating using first projector FOV 712A during a first integration time of a camera (or both cameras) and then illuminating using second projector FOV 712B during a second integration time (e.g. while turning off first illuminator For example, alternating acquisition of the cameras and synchronizing projection with the acquisition e.g. synchronizing integration time of a single frame (e.g. single image) of a camera with a corresponding projector. For example, programming integration time of the cameras to be asynchronous.

In some embodiments, alternatively or additionally to lenses, mirrors are used to align illuminator (and/or projector) FOV/s to corresponding camera FOV/s.

Figure 8A:
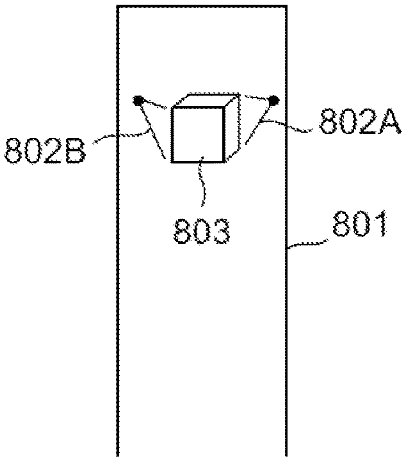
FIG. 8A is a simplified schematic of an add-on with two imaging FOVs, according to some embodiments of the invention.

FIG. 8A is a simplified schematic of an add-on 801 with two imaging FOVs 802A, 802B, according to some embodiments of the invention.

Figure 9A:
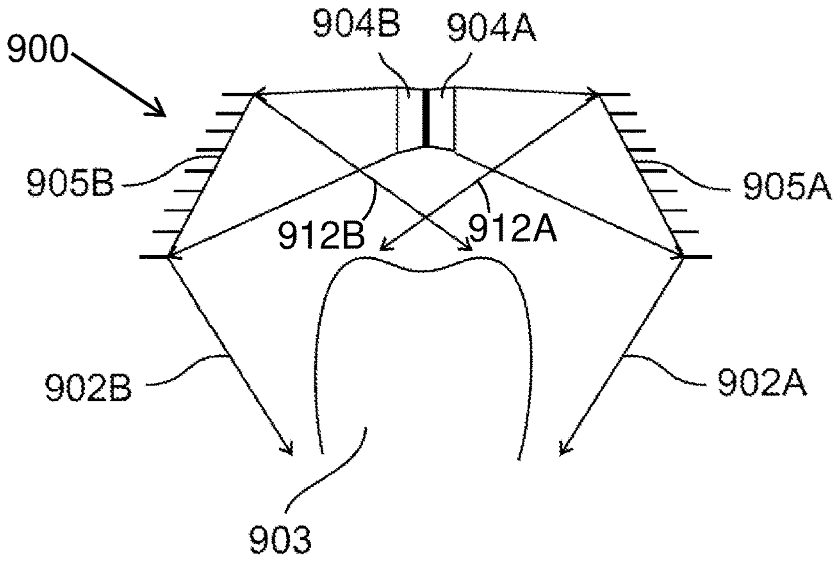
FIG. 9A is a simplified schematic cross section of an add-on, according to some embodiments of the invention.
Figure 9B:
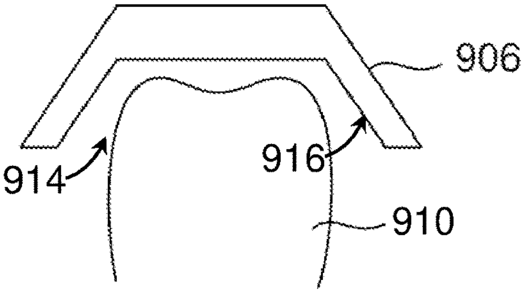
FIG. 9B is a simplified schematic of a slider, according to some embodiments of the invention.
Figure 9C:
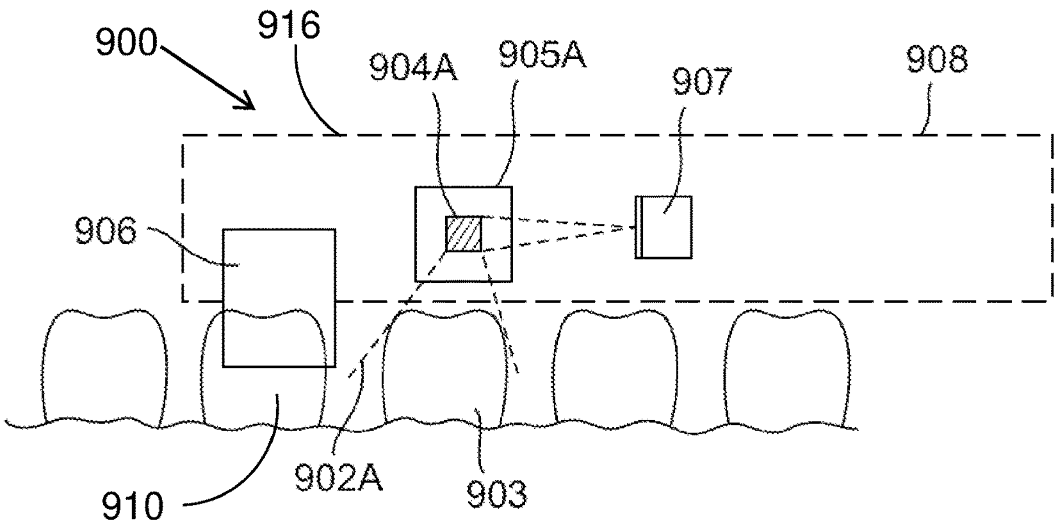
FIG. 9C is a simplified schematic of an add-on, according to some embodiments of the invention

In some embodiments, add-on 801 includes one or more feature as illustrated in and/or described regarding add-on 900 FIG. 9A and/or FIG. 9B, and/or FIG. 9C.

In some embodiments, add-on 801 has a first FOV 802A and a second FOV 802B. Where, in some embodiments, both FOVs 802A, 802B are directed towards a dental feature 803, for example, to collect images of more than one side of dental feature 803. In some embodiments, FOVs are directed at 90-270 degrees from each other, or 120-230 degrees from each other, or lower or higher or intermediate angles or ranges. In some embodiments, FOVs 802A, 802B are directed towards a center (e.g. longitudinal central axis) of a body of add on 801. In some embodiments, FOVs 802A, 802B are directed at an angle of 30-120 degrees to a longitudinal central axis of the body of add-on 801. In some embodiments, FOVs 802A, 802B emanate from and/or are positioned at a region of a distal portion of add-on 801.

Figure 8C:
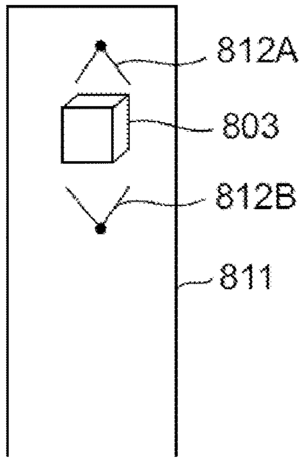
FIG. 8C is a simplified schematic of an add-on with two imaging FOVs, according to some embodiments of the invention.
Figure 8B:
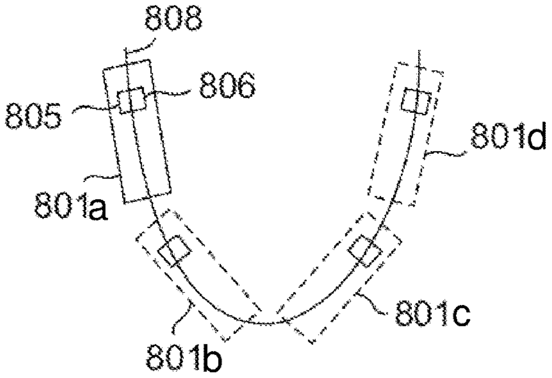
FIG. 8B is a simplified schematic illustrating scanning within a mouth using an add-on, according to some embodiments of the invention.

FIG. 8B is a simplified schematic illustrating scanning within a mouth using an add-on, according to some embodiments of the invention.

In some embodiments, FIG. 8B illustrates scanning of a tooth arc 808 using the add-on as illustrated and/or described regarding FIG. 8A. In some embodiments, while add-on is moved through different positions 801*a-d* illustrated on arc 808 images are captured of a lingual side 805 of teeth and a buccal side 806 of teeth.

In some embodiments, overlapping portions of images are used to connect (e.g. stitch together) images collected (e.g. images of buccal and lingual portion/s of a tooth or teeth) using the FOVs. For example, images including overlapping occlusional portion/s of teeth.

FIG. 8C is a simplified schematic of an add-on 811 with two imaging FOVs 812A, 812B, according to some embodiments of the invention.

In some embodiments, add-on 811 has a first FOV 812A and a second FOV 812B. Where, in some embodiments, both FOVs 812A, 812B are directed towards a dental feature 803, for example, to collect images of more than one side of dental feature 803. In some embodiments, FOVs are directed at 90-270 degrees from each other, or 120-230 degrees from each other, or lower or higher or intermediate angles or ranges. In some embodiments, FOVs 801A, 801B are directed along a longitudinal central axis of a body of add on 811. In some embodiments, FOVs 802A, 802B are directed at an angle of 0-30 degrees to a longitudinal central axis of the body of add-on 811. In some embodiments, FOVs 812A, 812B emanate from and/or are positioned at a region of a distal portion of add-on 811.

Figure 8D:
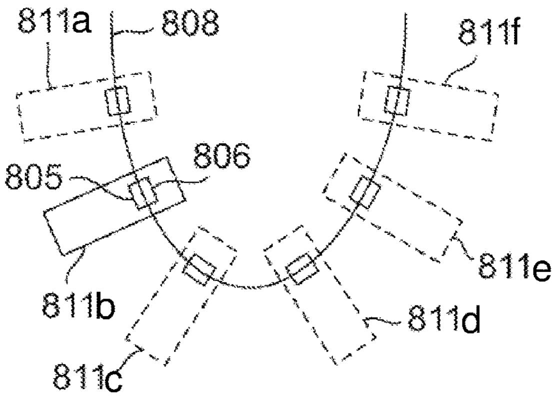
FIG. 8D is a simplified schematic illustrating scanning within a mouth using an add-on, according to some embodiments of the invention.

FIG. 8D is a simplified schematic illustrating scanning within a mouth using an add-on, according to some embodiments of the invention.

In some embodiments, FIG. 8D illustrates scanning (e.g. a jaw 808) using add-on 811 of FIG. 8C. In some embodiments, add-on 811 is moved along a teeth arc 808, through positions 811*a-f*, where, a body of add-on 811 is maintained with a central longitudinal axis about perpendicular (e.g. 45-105 degrees to) arc 808. In some embodiments, during movement through positions 811*a-f* images are collected both a lingual side 805 and buccal side 806 of teeth. Optionally, together with images of an occlusal part of the teeth.

FIG. 9A is a simplified schematic cross section of an add-on 900, according to some embodiments of the invention.

FIG. 9B is a simplified schematic of a slider 906, according to some embodiments of the invention.

FIG. 9C is a simplified schematic of an add-on 900, according to some embodiments of the invention.

FIGS. 9A-C, in some embodiments, illustrate the same add-on (or portion/s of the same add-on). In some embodiments, add-on 900 includes one or more feature as described regarding and/or illustrated for add-on 801 FIG. 8A and/or FIG. 8B.

Referring now to FIG. 9A, in some embodiments, two FOVs emanate from add-on 900 where, in some embodiments, arrows 902A, 912A indicate extremities of a first FOV and arrows 902B, 912B indicate extremities of a second FOV. In some embodiments, the FOVs illustrate imaging FOVs, or projector FOVs, or both e.g. each FOV corresponding to both an imager and a projector FOV. In some embodiments, the first and second FOV are imaging FOVs which, in some embodiments, correspond to a first and a second imager e.g. of a smartphone. In some embodiments, first and second FOV are each a portion of an imager FOV which is, in some embodiments, split within add-on 900. In some embodiments, transfer of both FOVs is through a central region of add-on 900. Where, in some embodiments, first mirrors 904A, 904B directs the FOVs away from the central region and second mirrors 905A, 905B direct the FOVs. In some embodiments, for example, as described regarding one or more of FIGS. 8A-D, FOVs enable collection of images from two sides of tooth 903 where optionally, one or both of the FOVs collects images of occasional (e.g. top surface) of tooth 903. In some embodiments, FOVs overlap. Where, in some embodiments, overlapping projector FOVs are used e.g. according to one or more feature as described regarding FIG. 7C.

In some embodiments, one or more surface from which the FOVs emanate is sized and/or shaped for scanning of teeth from above. For example, a side of a body of add-on 900 having an indentation sized and/or shaped to at least partially house a tooth.

Referring now to FIG. 9B. In some embodiments, FIG. 9B illustrates a cross section of a portion 906 of an add-on. In some embodiments, a side of add-on has an indentation e.g. including sloped portion/s 916. In some embodiments, sloping portions 916 are positioned to coincide with edges of a tooth 910. In some embodiments, a central region of one or more side of the add-on cross section is non-sloping for example, with an orientation perpendicular (or about perpendicular) to a central longitudinal axis of the add-on which is e.g. into a plane of the figure of FIG. 9B. Where, in some embodiments, the indentation is sized and/or shaped to at least partially house a tooth.

Potentially, shaping of add-on portion/s to fit a tooth enables rapid scanning as teeth are more likely to remain aligned with FOVs of the add-on during movement of the add-on.

Referring now to FIG. 9C. In some embodiments, a distal portion of add-on 900 includes a rider 906 which is sized and/or shaped to house teeth. For example, where rider 906 includes one or more feature as illustrated and/or described regarding add-on portion 906 FIG. 9B.

In some embodiments, rider 906 holds a portion of add-on 900 (e.g. a distal portion) in position e.g. by contacting a tooth 910 while a different tooth 903 is imaged by FOV 902A (where, in some embodiments, tooth 903 is imaged using two FOVs e.g. as described regarding FIG. 9A). Alternatively, in some embodiments, rider 906 is positioned at a portion of the add-on from which imaging and/or projection FOV/s emanate.

In some embodiments, an add-on includes a plurality of riders and/or a plurality of surfaces shaped to hold teeth. For example, where, an upper surface 916 of add-on 900 includes a rider and/or has a cross sectional shape configured to hold a tooth e.g. including an indentation sized and/or shaped to receive a portion of a tooth.

In some embodiments, a rider 906 includes elastic material (e.g. silicone, rubber). Elasticity of rider 906, for example, enabling secure holding of a tooth by the rider e.g. as the rider is elastically deformed to allow entrance to the tooth. Alternatively or additionally, in some embodiments, elasticity of rider 906 enables smooth movement over non planar tooth topography (e.g. bump/s and/or sharp edges), the elasticity allowing the rider to deform locally.

In some embodiments, rider 906 is detachable for example, a kit including a plurality of different sized and/or shaped riders 906 for use e.g. with different portion/s of a jaw and/or different jaw sizes (e.g. as affected and/or defined by age and/or sex). In some embodiments, a length of rider 906 in a direction of longitudinal axis of add-on 900 is sized to be larger in extent than a length of a tooth along a dental arc, for example, enabling rider 906 to continue to support and/or guide position of add-on 906 when a tooth in the dental arc is not present.

In some embodiments, optical unit 907 includes optical attachment to smartphone optics. Alternatively or additionally, in some embodiments, optical unit 907 includes add-on optic element/s.

Figure 10A:
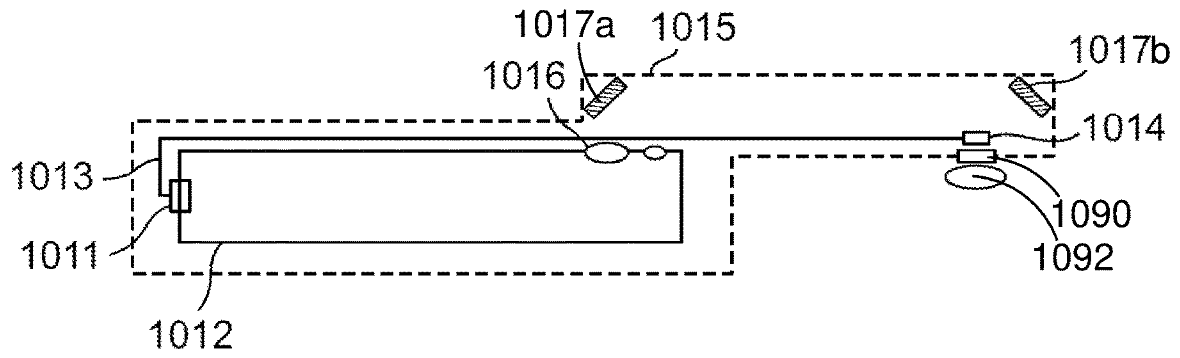
FIG. 10A is a simplified schematic of an add-on connected to a smartphone, according to some embodiments of the invention.

FIG. 10A is a simplified schematic of an add-on 1015 connected to a smartphone 1012, according to some embodiments of the invention.

In some embodiments, add-on 1015 includes an illuminator (e.g. LED) 1014. Where, in some embodiments, illuminator 1014 is part of a projector including, for example, a pattern 1090 and/or lens 1092. For example, as described elsewhere in this document, in some embodiments, images are acquired by smartphone camera 1016 where, in some embodiments, add-on includes an optical path through add-on 1015. Where, in some embodiments, optical path includes one or more mirror 1017*a*, 1017*b*.

In some embodiments, power is supplied to illuminator 1014 by smartphone 1012. For example, in some embodiments, add-on 1015 includes an electrical connection to a socket (e.g. connector) 1011 of smartphone 1012 that transfers power through wires 1013 to illuminator 1014. Optionally, in some embodiments, smartphone 1012 is data-connected to add-on 1015 e.g. where, in some embodiments, a smartphone processor controls illuminator 1014.

In some embodiments, smartphone 1012 is connected to add-on 1015 by being placed within a hollow of add-on 1015. Where, in some embodiments, the hollow is sized and/or shaped to house smartphone 1012. In some embodiments, add-on 1015 does not cover a screen of the smartphone and/or has a transparent portion covering the screen.

Figure 10B:
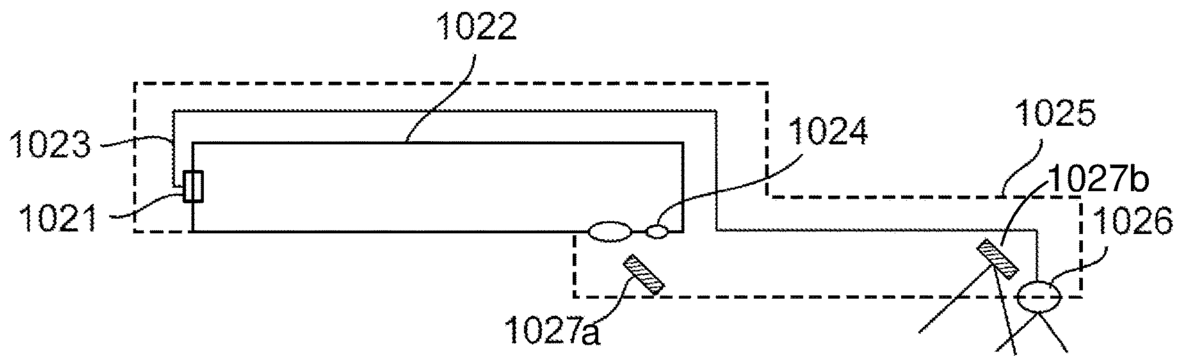
FIG. 10B is a simplified schematic of an add-on connected to a smartphone, according to some embodiments of the invention.

FIG. 10B is a simplified schematic of an add-on 1025 connected to a smartphone 1022, according to some embodiments of the invention.

In some embodiments, add-on 1025 includes an imager 1026. Where, in some embodiments, imager 1026 has electrical power connection and/or data connection to smartphone 1022 e.g. through connection of data and/or power wires 1023 at smartphone port 1021. In some embodiments, a FOV of an illuminator of smartphone 1024 is transferred through add-on 1025 e.g. by one or more mirror 1027*a*, 1027*b*. For example so that a FOV of illuminator 1024 overlaps with that of add-on imager 1026. Where, in some embodiments, an optical path from illuminator 1024 to light emanating from add-on includes one or more pattern and/or lens e.g. making a pattern projector.

Figure 10C:
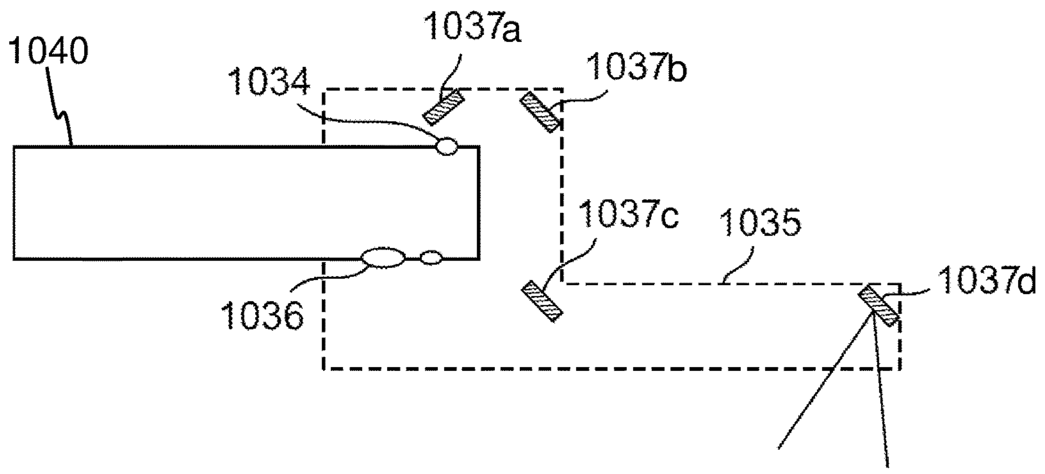
FIG. 10C is a simplified schematic of an add-on connected to a smartphone, according to some embodiments of the invention.

FIG. 10C is a simplified schematic of an add-on 1035 connected to a smartphone 1040, according to some embodiments of the invention.

In some embodiments, FIG. 10C illustrates an embodiment where optical paths are transferred by add-on 1035 of FOVs of an optical element/s 1034 on a first face of smartphone 1040 and optical element/s 1036 on a second face of the smartphone.

In some embodiments, illuminator is a NIR (Near Infra-Red) LED 1034, for example a proximity sensor, for example, a NIR projector, e.g. dots projector. Where an optical path through add-on 1035, in some embodiments, is provided by mirrors 1037*a-d*.

In some embodiments, NIR LED light projected on a tooth and is captured using a FOV of smartphone imager 1036 (the imaging FOV also transferred through add-on, in some embodiments). Where, in some embodiments, imager 1036 does not have an NIR cut filter. In some embodiments, reflected NIR light is used to detect plaque on the scanned teeth. In some embodiments, the NIR light is transferred through add-on 1035 using optical fiber e.g. alternatively or additionally to mirror transfer. In some embodiments, an add-on includes a NIR LED e.g. as part of the add-on where powering of the NIR LED is via the smartphone, and/or via an add-on power source.

FIG. 27A is a simplified schematic of an add-on 2700 attached to a smartphone 2702, according to some embodiments of the invention.

FIG. 27B is a simplified schematic of an add-on 2700, according to some embodiments of the invention.

FIG. 27C is a simplified schematic side view of an add-on 2700, according to some embodiments of the invention.

In some embodiments, a body 2704 of add-on 2700 extends from a connecting portion 2706 (also herein termed "connector") of the add-on.

In some embodiments, add-on 2700 includes one or more feature of add-ons as described elsewhere in this document.

In some embodiments, body 2704 extends in a direction which is generally parallel to an orientation of front face 2742 and/or back face 2740 of smartphone 2702. Where, in some embodiments, smartphone front face 2742 hosts a screen of the smartphone and back face 2740 hosts one or more optical element e.g. imager 2720 and/or illuminator.

Where, in some embodiments, the connecting portion 2706 is sized and/or shaped to hold a portion of smartphone 2702. In some embodiments, connecting portion 2704 includes walls 2708 which surround at least partially and/or are adjacent to one or more side 2710 of smartphone 2702. In some embodiments, walls 2708 at least partially surround edges of an end of the smartphone. In some embodiments, walls are connected via a base 2730 of the connector.

In some embodiments, connector 2706 includes an inlet 2712 to an optical path 2714 of add-on 2700. Where, in some embodiments, optical path 2714 transfers light entering the inlet (e.g. from a smartphone optical element e.g. imager 2724) through add-on body 2704.

In some embodiments, optical path 2714 includes one or more mirror 2716, 2718.

In some embodiments, a distal tip of body 2704 includes an angled and/or curved outer surface e.g. surface adjacent to mirror 2716. Where, in some embodiments, an angle of the surface is 10-60 degrees to an angle of outer surfaces of body 2704. The angled surface potentially facilitating positioning of the distal tip into cramped dental position/s e.g. a distal end of a dental arch.

In some embodiments, add-on 2700 includes an illuminator 2722 where, in some embodiments, the illuminator FOV 2724 overlaps that of the smartphone imager 2726. In some embodiments, illuminator 2722 is powered by an add-on power source (not illustrated). Where, in some embodiments, the power source is hosted in the body and/or connector. In some embodiments, illuminator 2722 is powered by the smartphone. In some embodiments, the add-on attached to the smartphone includes an additional illuminator (e.g. of the smartphone e.g. transferred by the add-on and/or of the add-on). In some embodiments, the illuminator illuminates with patterned light and the additional illuminator illuminates with non-patterned light.

Exemplary Add-on UI/UX Embodiments

Figure 11A:
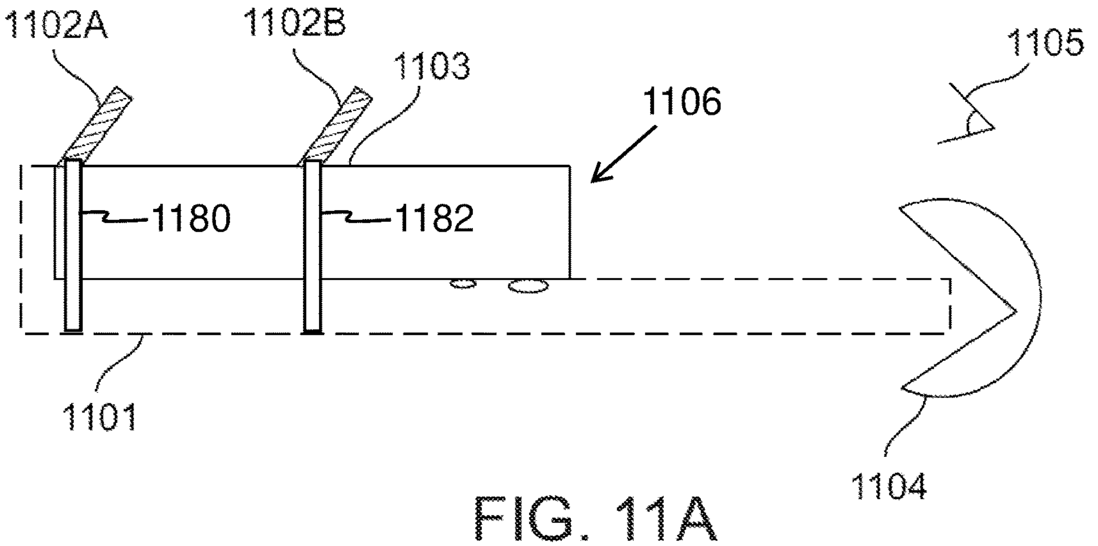
FIG. 11A is a simplified schematic of an add-on connected to a smartphone, according to some embodiments of the invention.
Figure 11B:
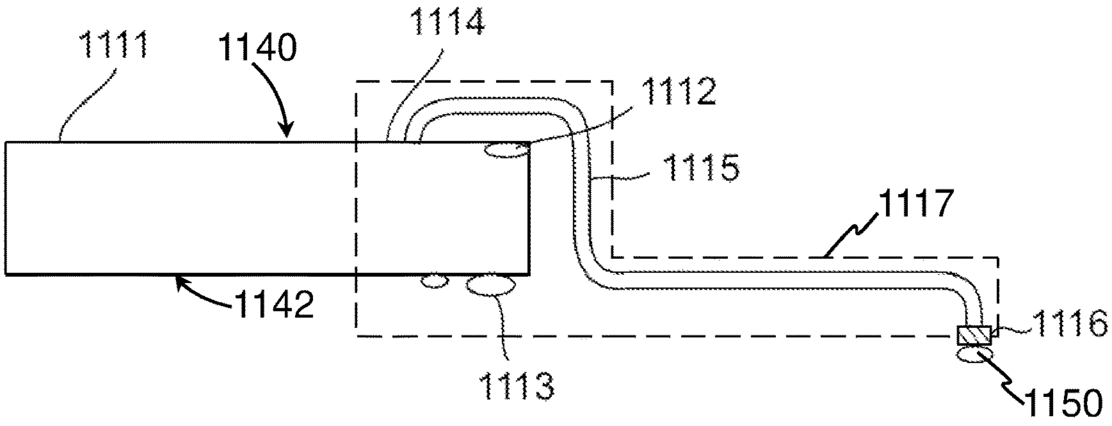
FIG. 11B is a simplified schematic of an add-on connected to a smartphone, according to some embodiments of the invention.

FIG. 11A is a simplified schematic of an add-on 1101 connected to a smartphone 1106, according to some embodiments of the invention.

In some embodiments, add-on 1101 includes one or more viewing mirror 1102A. Where, in some embodiments, viewing mirror 1102A enables a user to view a screen 1103 of smartphone 1106 e.g. while scanning dental features using add-on 1101. In some embodiments, mirror 1102A is connected to add-on by a connector 1180. Alternatively or additionally to a connector, in some embodiments, mirror 1102A is connected to add-on by connection of the mirror to a body of add-on e.g. directly e.g. where add-on forms a case covering at least portion/s of the smartphone.

In some embodiments, mirror 1102A is positioned e.g. at a base of smartphone 1103 to reflect and display to user 1105 a lower portion of the smartphone screen.

In some embodiments, a mirror 1102B (e.g. connected by a connector 1182 and/or a body of add-on 1101) for reflection of smartphone screen to user 1105 is positioned e.g. at a central region of the smartphone and/or in a position above an upper part of the smartphone screen reflecting, to the user only an upper portion of the screen.

In some embodiments, add-on includes two mirrors 1102A, 1102B, where, in some embodiments, mirror 1102A extends further from screen 1103 than mirror 1102B allowing user view 1105 (e.g. while the user is scanning with the smartphone and add-on) of portion/s of both mirrors. Where, each mirror reflects different part/s of the screen.

Potentially allowing user 1104 to view relevant information while holding smartphone 1103 in such a way that a lower portion of the screen is obscured.

In some embodiments, relevant information for a user is displayed, on portion/s of the smartphone screen which are reflected to user eye/s 1105.

1G. 11B is a simplified schematic of an add-on 1117 connected to a smartphone 1111, according to some embodiments of the invention.

In some embodiments, FOVs of cameras 1112, 1113 located on different faces (e.g. opposite faces) of smartphone 1111 are transferred by add-on 1117. Where, for example, in some embodiments, camera 1112 is a "selfie" camera located on a side of smartphone 1111 hosting a smartphone screen 1114. Where, in some embodiments, camera 1113 is a main camera disposed on a second face 1142 of smartphone 1111.

In some embodiments, the selfie camera 1112 is a pop-up camera which is in an open configuration when collecting images, where the add-on is configured to transfer the a FOV of selfie camera e.g. via optical element/s when the camera is open.

In some embodiments, a portion of smartphone screen 1114 is used as an illuminator e.g. to provide an illumination FOV e.g. for imaging FOV of selfie camera 1112 and/or illumination for another camera e.g. camera 1113. Where, in some embodiments, optical path 1115 of transfer of smartphone screen illumination is illustrated. In some embodiments, optical path 1115 is provided by optical fibers and/or mirror/s and/or prism/s. In some embodiments, a pattern 1116 and/or lens 1150 are located on optical path 1115 e.g. transforming smartphone screen illumination into a pattern projector. In some embodiments, smartphone 1111 is programmed to illuminate the portion of screen 1114 used as an illuminator with high power white light.

Figure 11C:
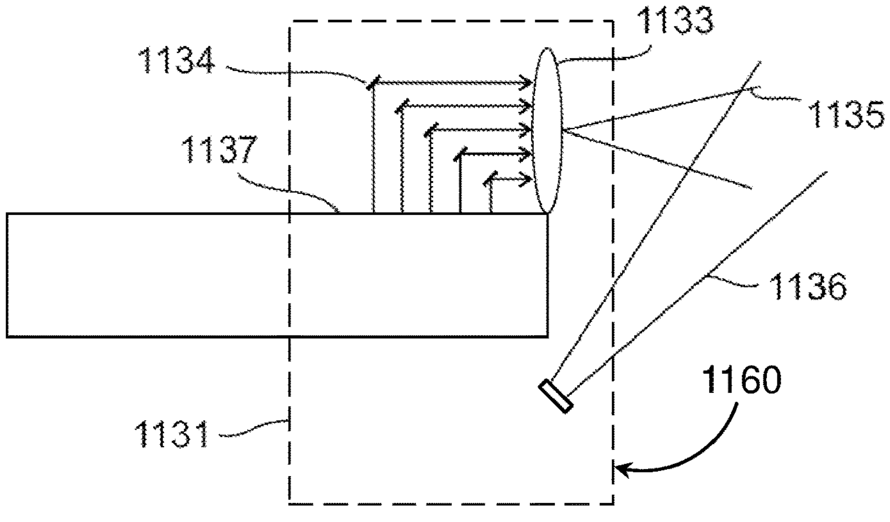
FIG. 11C is a simplified schematic of an add-on connected to a smartphone, according to some embodiments of the invention.

FIG. 11C is a simplified schematic of an add-on 1131 connected to a smartphone 1137, according to some embodiments of the invention.

In some embodiments, smartphone screen 1132 is directly used to provide patterned illumination. Where, in some embodiments, add-on 1133 transfers patterned light emitted from smartphone screen 1137 to illuminate (e.g. overlap with) an imaging FOV 1136. In some embodiments, add-on 1131 includes one or more projection lens 1133 e.g. to adjust focus of patterned light.

In some embodiments, patterned light emitted by the screen is transferred through add-on 1131 by one or more mirrors 1134 and/or other optical element/s e.g. prisms e.g. prior to being incident on projection lens 1133.

In FIG. 11C projection FOV 1135 and imager FOV 1136 overlap at a distance from add-on body 1131 configured for imaging of dental features e.g. at 50-150 mm, or 80-120 mm, or about 100 mm or about 80 mm or about 120 mm or lower or higher or intermediate ranges or distances from a face 1160 of add-on 1131.

Figure 11D:
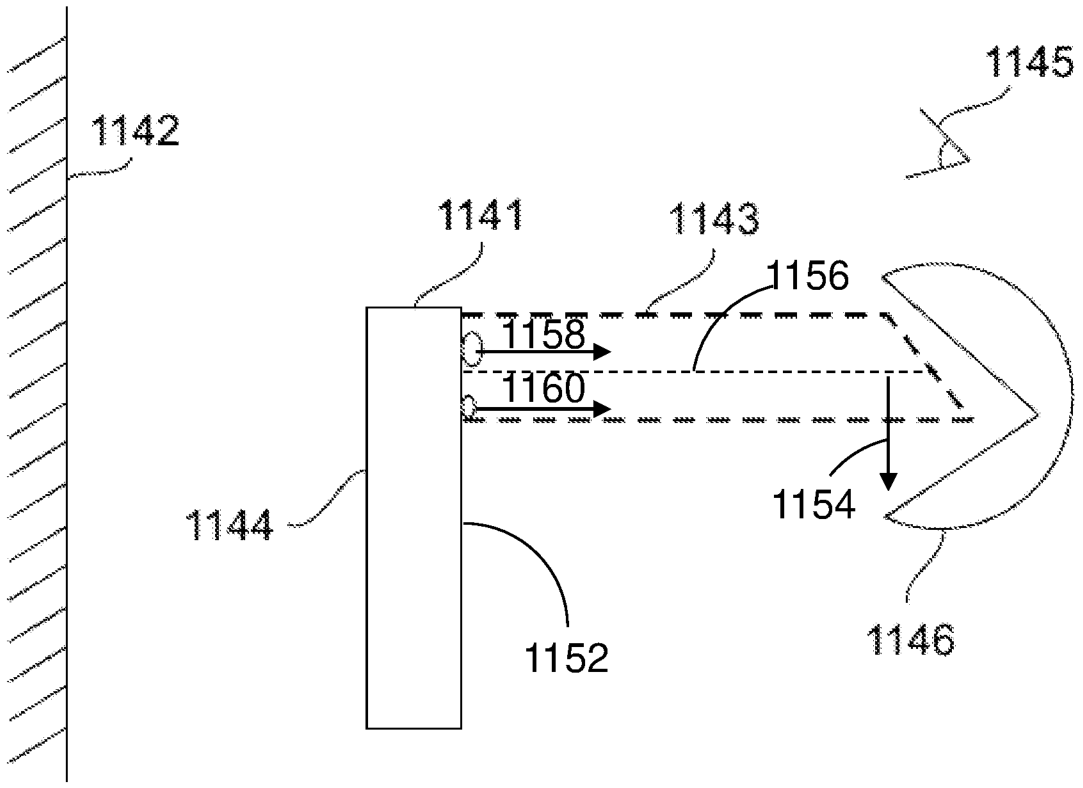
FIG. 11D is a simplified schematic of an add-on attached to a smartphone, according to some embodiments of the invention.

FIG. 11D is a simplified schematic of an add-on 1143 attached to a smartphone 1141, according to some embodiments of the invention.

In some embodiments, add-on 1143 extends from a back face 1152 of smartphone 1143. Where a longitudinal central axis 1156 and/or an axis of elongation 1156 of add-on 1143 is in a direction generally (e.g. about) perpendicular to back face 1152 and/or a front face hosting screen 1144. In some embodiments, one or more FOV 1154 emanating from a distal end of add-on is at an angle which is generally (e.g. about) parallel to one or both the smartphone faces and/or which is generally (e.g. about) perpendicular to a direction of emanation of the FOV/s 1158, 1160 from the smartphone and/or to a longitudinal central axis 1156 and/or an axis of elongation 1156 of the add-on. Where, in some embodiments, add-on transfers an FOV of a smartphone imager and optionally includes an illuminator. In some embodiments, alternatively or additionally to an add-on illuminator, the add-on transfers an FOV of a smartphone illuminator.

In some embodiments, a user 1145, 1146 scans their mouth using add-on 1143 attached to a smartphone 1141 whilst in view 1145 of a mirror 1142, for example, opposite mirror e.g. a bathroom mirror. In some embodiments, reflected images guide the user during scanning inside his mouth 1146.

In some embodiments, during scanning, a smartphone screen 1144 displays relevant information to the user, where the user views 1145 the information in a reflection in mirror 1142. In some embodiments information displayed on smartphone screen is displayed in mirror-image.

In some embodiments, the information on the smartphone is flipped, for example in response to one or more input indicating that the user is scanning his upper jaw and/or that the smartphone is being held upside down. In some embodiments, the input includes a position of smartphone 1144 detected by an internal IMU (Inertial measurement unit) of the smartphone.

Figure 12:
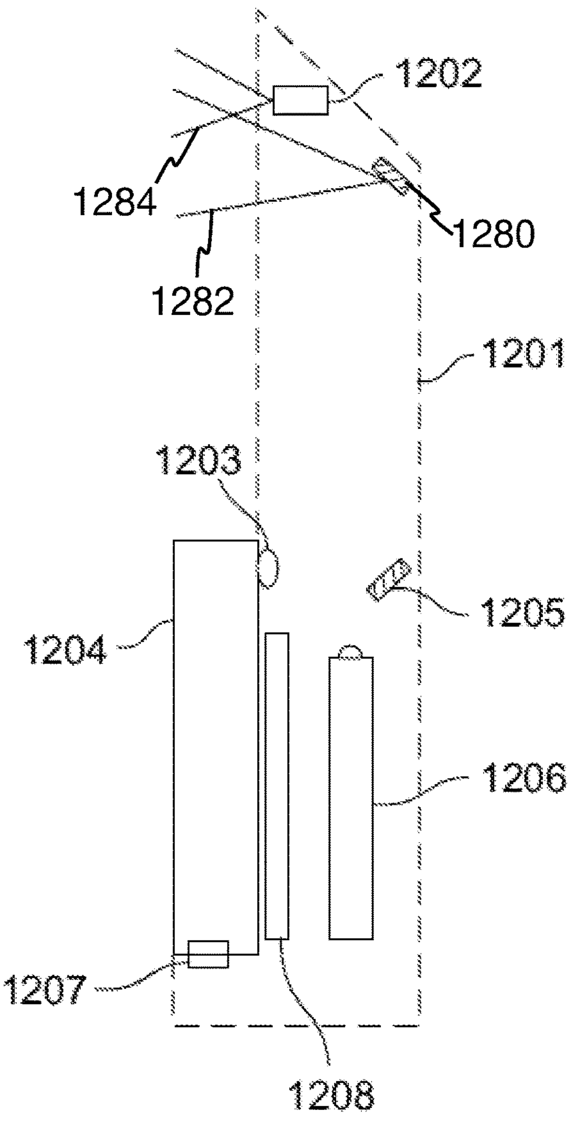
FIG. 12 is a simplified schematic view of a scanning add-on, connected to a smartphone, according to some embodiments of the invention.

FIG. 12 is a simplified schematic view of a scanning add-on 1201, connected to a smartphone 1204, according to some embodiments of the invention.

In some embodiments, add-on 1201 includes a pattern projector 1202. In some embodiments, add-on 1201 does not include an imager. In some embodiments, add-on optically transfers a FOV 1284 of imager 1203 (e.g. smartphone imager 1203) for example, by one or more mirror 1205, 1280.

In some embodiments, add-on 1201 is mechanically attached to device 1204. Optionally, in some embodiments one or more mirror 1205 and/or lens (not illustrated) change the device camera's FOV position and/or direction as described elsewhere in this document. In some embodiments, add-on 1201 includes a pattern projector 1202 e.g. including a LED, and/one or more pattern and/or lens. In some embodiments the pattern projector is powered by a LED driver. In some embodiments the projector is powered directly from the device power source, for example the smartphone connector 1207.

In some embodiments, add-on 1201 includes a battery 1206 (e.g. a rechargeable battery 1206). In some embodiments, battery 1206 is recharged through a connector (not illustrated) e.g. a USB3 connector. Alternatively, or additionally, in some embodiments rechargeable battery 1206 is recharged through a smartphone connector 1207.

Alternatively or additionally, in some embodiments, add-on 1201 includes a wireless charging circuit 1208 which enables wireless re-charging of batter 1206 by smartphone 1202 e.g. using reverse wireless charging.

In some embodiments, component 1206 is a power source which alternatively or additionally to including a battery includes a super capacitor.

Exemplary Fluorescence Measurement

Figure 13:
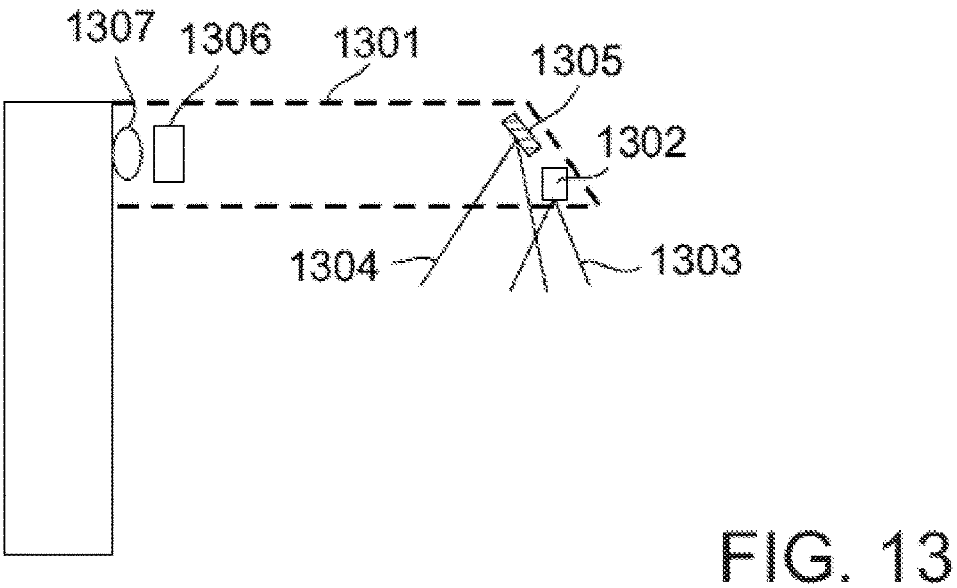
FIG. 13 is a simplified schematic of an add-on, according to some embodiments of the invention

FIG. 13 is a simplified schematic of an add-on 1301, according to some embodiments of the invention.

In some embodiments, add-on 1301 include an illuminator 1302 for fluorescence measurement of the teeth and/or the oral cavity. In some embodiments, illuminator 1302 is configured to illuminate dental feature/s for dental florescence measurements. In some embodiments, the illuminator includes a UV or near UV LED 1302, for example emitting light with wavelength of 300-440 nm or 340-410 nm, or about 340 nm, about 365 nm, about 385 nm, about 400 nm, about 405 nm or lower, or higher or intermediate ranges or wavelength. In some embodiments, the UV light is projected on the teeth using FOV 1303 and the fluorescence light emanating in result from a tooth and/or other materials in the oral cavity, for example plaque or tartar, is captured by one of the smartphone imagers e.g. at FOV 1304 (e.g. transferred to the smartphone imager via mirror 1305).

In some embodiments add-on 1301 includes one or more filter 1306. Where, in some embodiments, filter 1306 is positioned in an optical path of add-on 1301 to smartphone camera 1307. In some embodiments, filter 1306 removes light of wavelength/s projected by illuminator 1302.

In some embodiments, filter 1306 includes a notch filter (band-stop filter). Where, in some embodiments, notch filter characteristics are centered around a frequency and/or frequency range of light emitted by illuminator 1302. For example, in an exemplary embodiment, illuminator 1302 emits 405 nm wavelength light (e.g. where illuminator 1302 includes a 405 nm LED) and filter 1306 includes a notch filter with a 405 nm center and 30 nm width between two −3 dB frequencies.

In some embodiments filter 1306 includes a high pass filter. Where, in some embodiments, high pass filter characteristics are selected to pass frequencies higher than a frequency and/or frequency range of light emitted by illuminator 1302. In an exemplary embodiment, illuminator 1302 emits 405 nm wavelength light (e.g. where illuminator 1302 includes a 405 nm LED) and a high pass filter with −3 bB at 450 nm is used.

In some embodiments, filter 1306 includes a bandpass filter. Where, in some embodiments, a center frequency of the band pass filter corresponds to expected and/or normal tooth autofluorescence wavelength/s resulting from illumination of dental object/s by a frequency and/or frequency range of light emitted by illuminator 1302. Where, in some embodiments, a central frequency of a bandpass filter is 520 nm, or about 520 nm, where, in some embodiments, bandpass passes a frequency width of 20 nm, or 50 nm, or 100 nm, or 10-150 nm, or 20-100 nm, or lower of higher or intermediate widths or ranges.

In some embodiments, filter 1306 includes a filter corresponding to expected plaque and/or tartar fluorescence frequencies (which, in some embodiments, have higher frequency/ies than the projected light). Where, for example, in some embodiments, a bandpass filter has a center frequency of 650 nm (or a center between 400-800 nm), with a width of 20 nm or 50 nm or 100 nm or lower or higher or intermediate widths.

Exemplary Dental Tomography

Figure 14A:
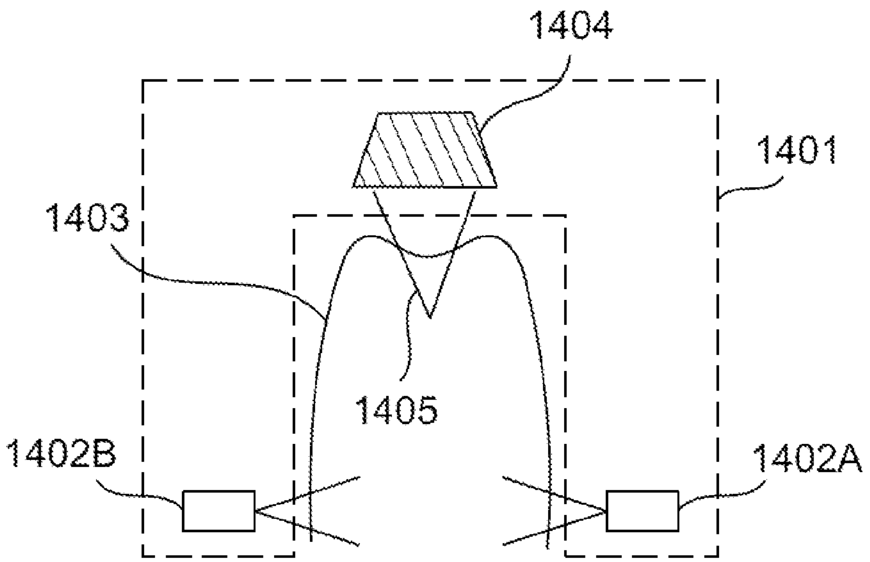
FIG. 14A is a simplified schematic cross section of an add-on, according to some embodiments of the invention.

FIG. 14A is a simplified schematic cross section of an add-on 1401, according to some embodiments of the invention.

Figure 14B:
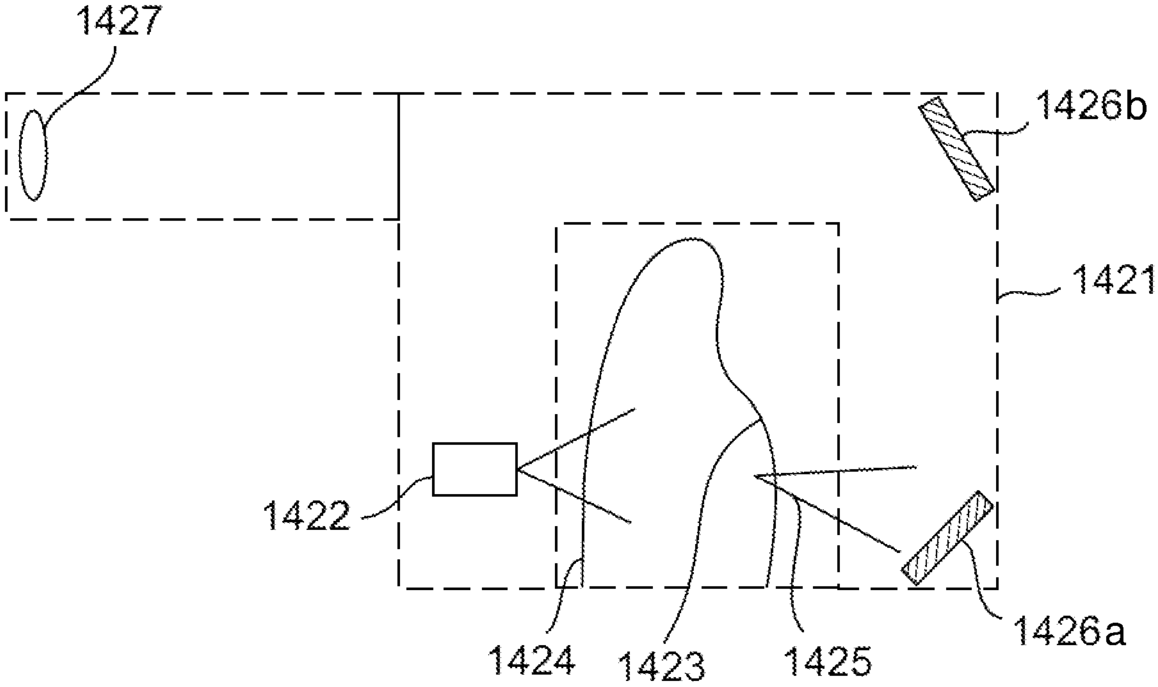
FIG. 14B is a simplified schematic cross section of an add-on, according to some embodiments of the invention.

FIG. 14B is a simplified schematic cross section of an add-on 1421, according to some embodiments of the invention.

In some embodiments, FIGS. 14A-B illustrate add-ons which include at least one illuminator 1402A, 1402B, 1422. In some embodiments, illuminators 1402A, 1402B, 1422 are configured to supply light for dental tomography measurements.

In some embodiments, an add-on 1401, 1421, including one or more illuminator, for example, a tomography measurement add-on, has a shape configured to surround a dental feature 1403 FIG. 14A, 1423 FIG. 14. For example, a shape including one or more feature as illustrated in and/or described regarding add-on 900 FIG. 9A and/or slider 906 FIG. 9B and/or FIG. 9C.

In some embodiments, one or more of illuminators 1402A, 1402B FIG. 14A, illuminator 1422 FIG. 14B, include one or more LED and/or a laser diode (LD) and/or a SLD (super luminescent diode).

Referring now to FIG. 14A, light, in some embodiments, is projected onto dental feature 1403. Where, for example, in some embodiments, dental feature 1403 is a tooth. In some embodiments, light is projected onto one or more sides of feature 1403 e.g. projected by sources 1402A and 1402B. In some embodiments, one or both of sources 1402A, 1402B, include a 780 nm LD, or illuminate at 850 nm, or between 780-850 nm, or between 700-1000 nm, or lower or higher or intermediate ranges or wavelengths.

In some embodiments, projection of light is at a lower portion of the tooth 1403 e.g. adjacent to gums. In some embodiments, light is projected at an about perpendicular angle to the dental feature (e.g. tooth) 1405. In some embodiments, light escaping tooth 1405 is reflected away from the tooth e.g. towards a smartphone camera by at least one mirror 1404.

Referring now to FIG. 14B, in some embodiments, a light source 1422, for example a 780 nm LED, a 850 nm LED, a 940 nm LED or a light source of 500-1000 nm wavelength light is projected onto a side 1424 of the tooth, for example a lingual side 1424 of a tooth 1423 (e.g. an incisal tooth which, in some embodiments is suitable for tomography (and/or trans-illuminance) as it has low thickness). In some embodiments, light passing through the tooth (e.g. emanating from a buccal area 1425 of the tooth) is directed towards a smartphone imager 1427 e.g. by one or more mirror 1426*a*, 1426*b*.

Additionally, or alternatively, to light transmitted through the tooth, in some embodiments, projected light which is reflected from tooth surface 1424 is measured. For example, where, in some embodiments, one or more mirror e.g. located adjacent to light source 1422 (e.g. located on a same side of tooth to the light source) transfers the light to an imager e.g. smartphone camera 1427. In some embodiments, reflected light from the tooth surface is measured using one or more additional camera, for example, an add-on camera e.g. positioned between imager 1427 and mirror 1426*b*.

Figure 15A:
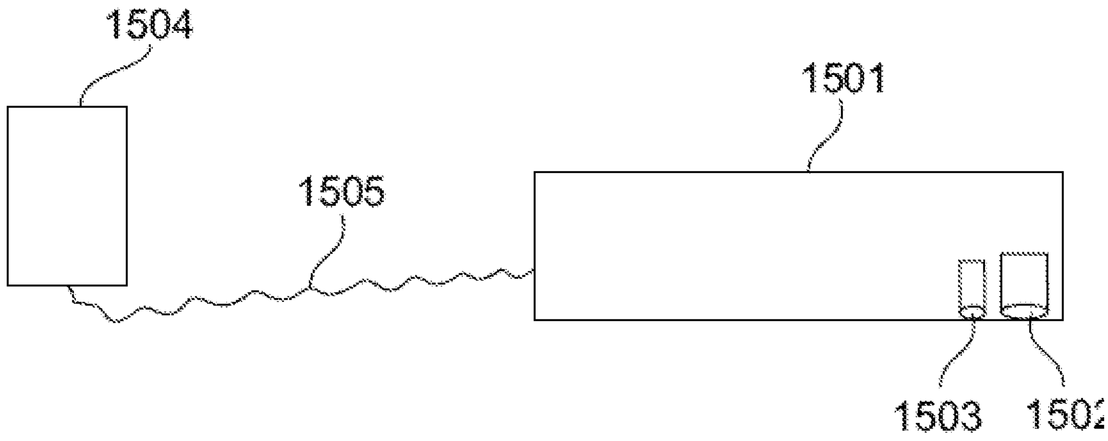
FIG. 15A is a simplified schematic of an add-on, according to some embodiments of the invention.

FIG. 15A is a simplified schematic of an add-on 1501, according to some embodiments of the invention.

In some embodiments, add-on 1501 includes one or more camera 1502. In some embodiments, add-on 1501 includes one or more illuminator (and/or projector) 1503. In some embodiments, a processor is connected e.g. by wire and/or cable connection 1505 to a device 1504. Where, in some embodiments, device 1504 includes a processor. In some embodiments, 1504 is a device e.g. smartphone and connector 1505 provides power and/or data connection of smartphone power supply and/or data connection of a smartphone processor to illuminator 1503 and/or imager 1502.

Where, connection, in some embodiments, is by USB (e.g. type C USB) and/or by a lightening connector. In some embodiments, the processor of device 1504 receives image/s acquired by imager 1502 and/or controls imaging and/or illumination e.g. by imager 1502 and/or illuminator 1503.

It should be understood that embodiments of add-ons as described in this document, in some embodiments, are not mechanically connected to a smartphone and/or do not use smartphone optical component/s.

Figure 15B:
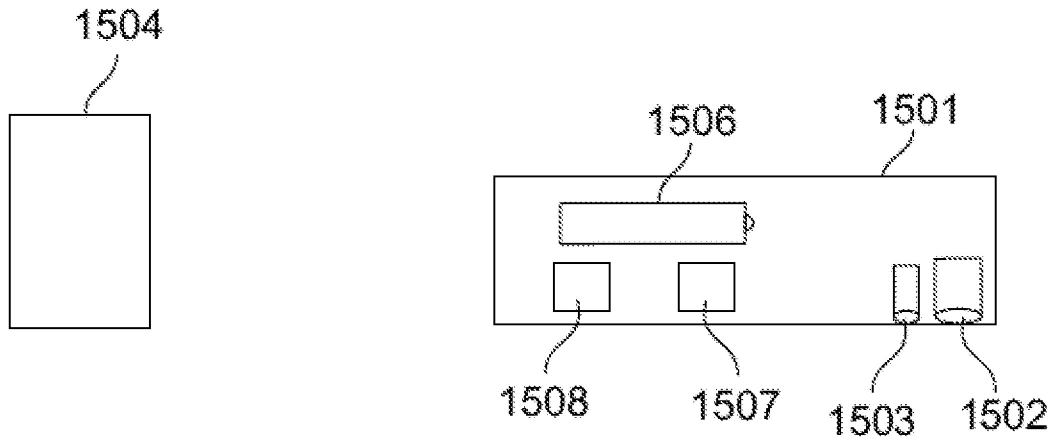
FIG. 15B is a simplified schematic of an add-on, according to some embodiments of the invention.

FIG. 15B is a simplified schematic of an add-on 1501, according to some embodiments of the invention.

In some embodiments, add-on 1501 is wirelessly connected to a smartphone 1504, for example using WiFi and/or Bluetooth.

In some embodiments, add-on includes one or more of; a power source (e.g. battery) 1506, a processing unit 1507, a wireless transmitter and/or transceiver 1508.

Figure 16A:
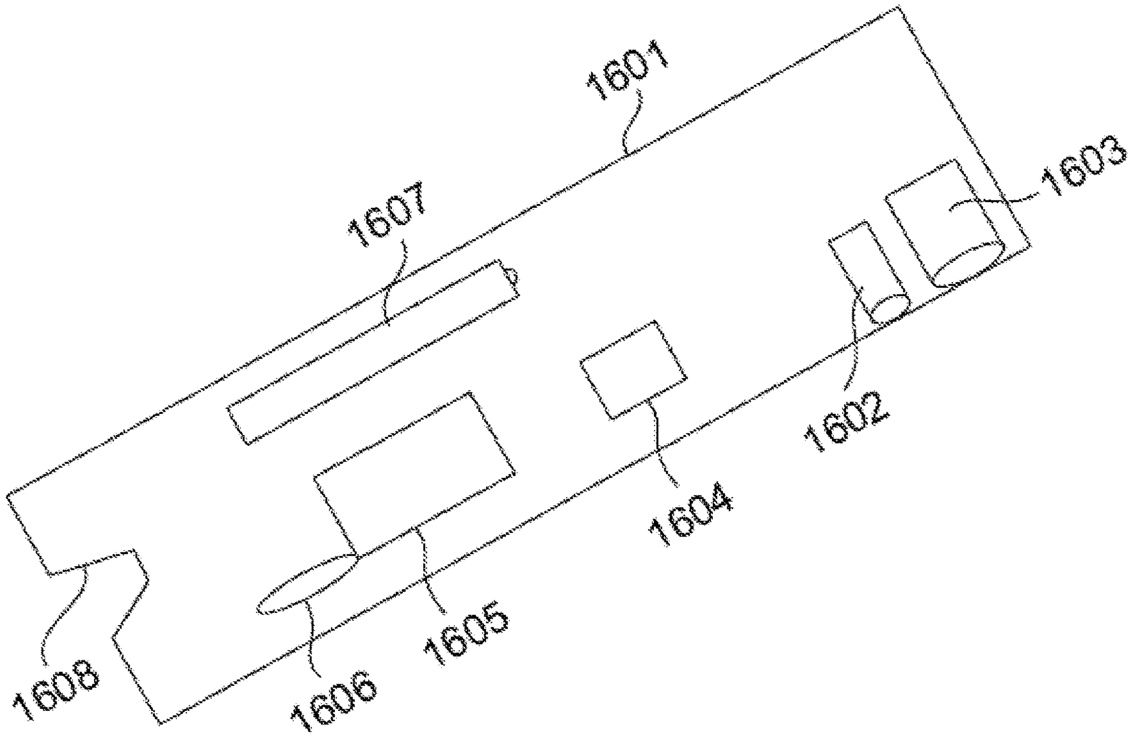
FIG. 16A is a simplified schematic of an add-on, according to some embodiments of the invention.

FIG. 16A is a simplified schematic of an add-on 1601, according to some embodiments of the invention.

In some embodiments, add-on 1601 includes an adapter 1608 configured to connect add-on 1601 to one or more other device e.g. handheld consumer product. In some embodiments, adapter 1608 provides mechanical connection between add-on and a product.

In some embodiments, add-on 1601 includes a camera 1603 and, in some embodiments, one or more projector 1602. Where, in some embodiments, projector 1602 and/or camera 1603 enable collection of images e.g. images containing depth information.

In some embodiments, add-on 1601 includes one or more inertial measurement unit (IMU) 1604 which, in some embodiments, senses orientation of the add-on. In some embodiments, add-on 1601 includes a processing unit and/or and a wireless transceiver 1605 which optionally includes an antenna 1606. Where, in some embodiments, processing unit and/or transceiver 1605 enable connection between a host, e.g. a smartphone and add-on. In some embodiments, add-on 1601 includes a power source (e.g. battery) 1607. In some embodiments, add-on 1601 includes one or more circuit for wired and/or wireless charging.

Figure 16B:
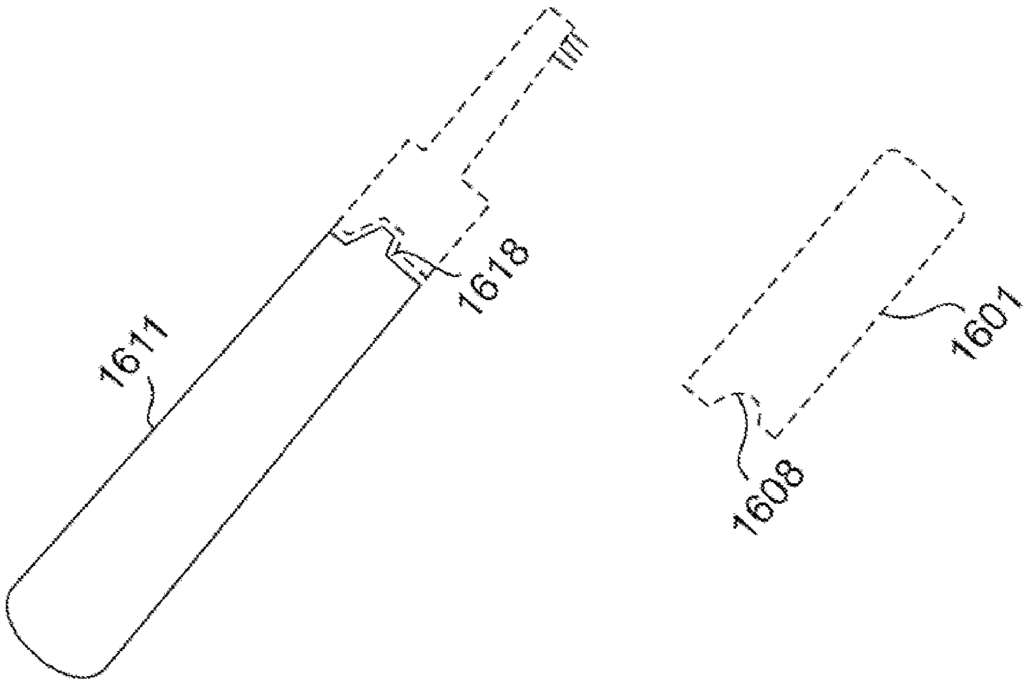
FIG. 16B is a simplified schematic of a consumer device and an add-on, according to some embodiments of the invention.

FIG. 16B is a simplified schematic of a consumer device 1611 and an add-on 1601, according to some embodiments of the invention.

In some embodiments, add-on 1601 includes one or more feature of add-on 1601 FIG. 16A. In some embodiments, consumer device 1611 is an electrical toothbrush 1611. In some embodiments, consumer device 1611 includes a mechanical adapter 1618 e.g. between the brush body and brushing head/s. In some embodiments, add-on 1601 adapter 1608 is configured to be connected to mechanical adapter 1618 instead of the toothbrush 1611.

In some embodiments, mechanical vibrations and/or movements of the toothbrush 1611 are used to power the add-on, for example using one or more dynamo to generate electricity energy from mechanical movement/s of the toothbrush.

Additional Exemplary Methods

Figure 17A:
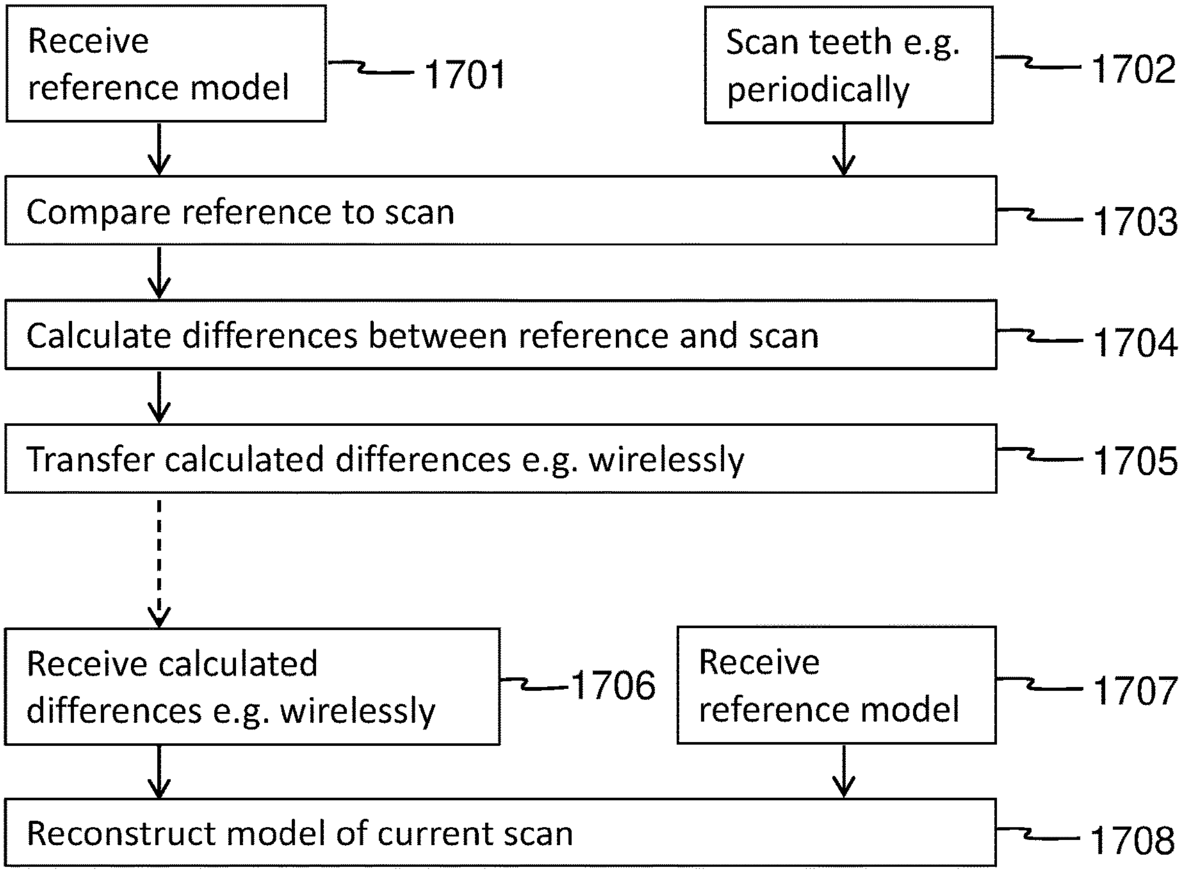
FIG. 17A is a flow chart of a method, according to some embodiments of the invention.

FIG. 17A is a flow chart of a method, according to some embodiments of the invention.

In some embodiments, steps 1701-1705 are performed by a processor of an add-on.

At 1701, in some embodiments, a reference model is received e.g. uploaded to the add-on. Where, in some embodiments, the reference model is a model (e.g. 3D model) of patient jaws and/or dental feature/s. In some embodiments, the reference model is constructed using measurements collected during scanning (scanning, e.g. as described regarding step 2114 FIG. 21). In some embodiments, the reference model is a model generated with previous scan data (e.g. collected with the add-on).

At 1702, in some embodiments, one or more scan (e.g. periodical scans) is performed with the add-on.

At 1703, in some embodiments, the reference model received at step 1701 is compared to periodical scan/s acquired at step 1702.

At 1704, in some embodiments, differences between the reference model and a scanned model are calculated 1704 e.g. for each periodic scan acquired at step 1703.

In some embodiments, differences between the reference model and a scanned model are data lighter than the scanned model.

At 1705, in some embodiments, the calculated difference/s are transmitted e.g. over a low bandwidth connection e.g. wirelessly. For example, from add-on to a processor e.g. of the smartphone.

At 1706, in some embodiments, calculated difference/s are received by a second processor. For example, a processor of the smartphone, a processor hosted by the cloud, a processor a dental clinic.

At 1707, in some embodiments, the second processor of step 1706 receives the reference model. For example, in some embodiments, a dental clinic IOS generates the reference model and then receives at step 1706 the calculated differences.

At 1708, in some embodiments, the scanned model is reconstructed using the reference model and the calculated differences.

Figure 17B:
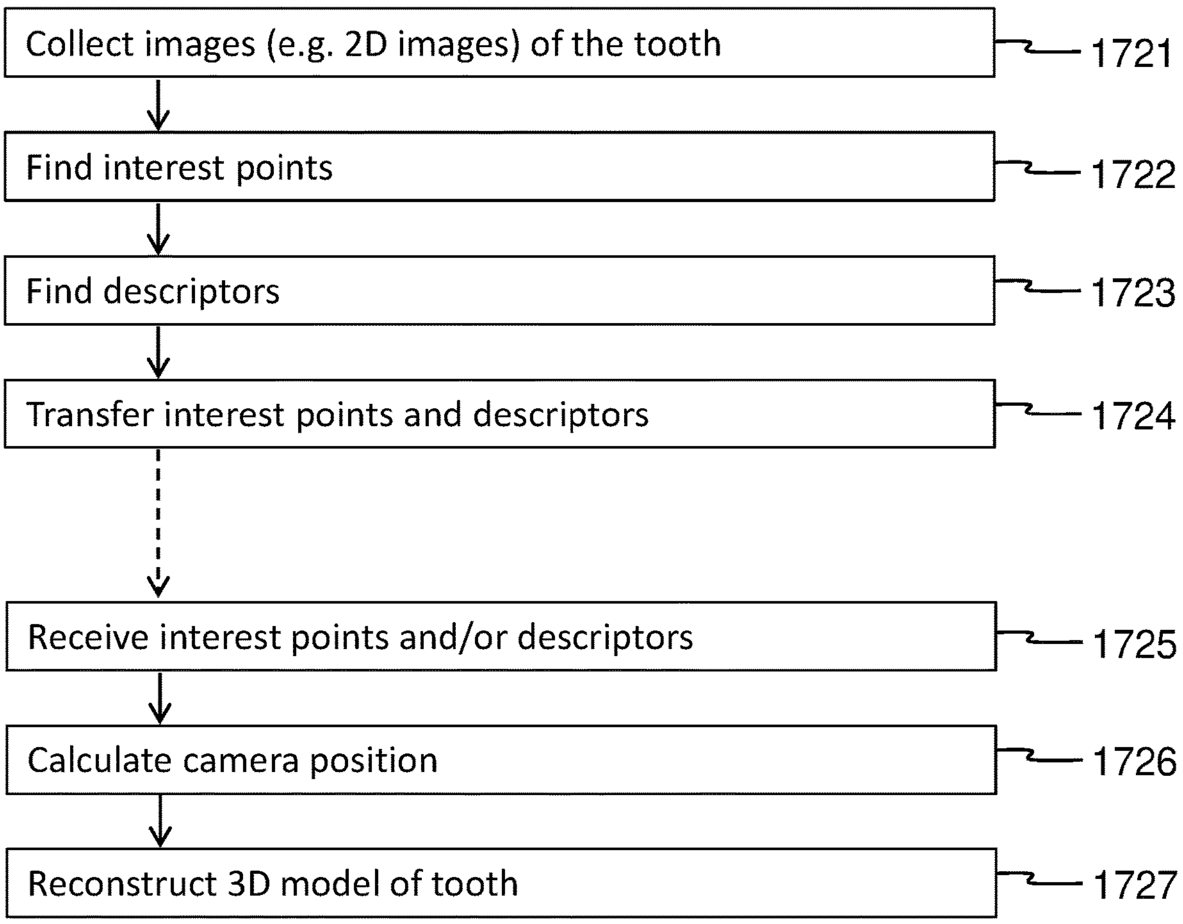
FIG. 17B is a flow chart of a method, according to some embodiments of the invention.

FIG. 17B is a flow chart of a method, according to some embodiments of the invention.

At 1721, in some embodiments, images are collected of one or more dental feature e.g. one or more tooth. For example, using an add-on and/or smartphone e.g. as described elsewhere in this document.

At 1722, in some embodiments, one or more interest point in one or more of the images are identified. Where, in some embodiments, interest points are identifiable features which are identified on two images, and, potentially enable matching of the images. Where an exemplary interest points include high contrasts e.g. a black mark on a white tooth e.g. a 3D peak of an upper portion of a tooth.

At 1723, in some embodiments, one or more descriptor (e.g. for one or more interest point) in one or more of the images are identified. Where, in some embodiments, a descriptor is a compressed representation of a corresponding interest point. Where one or more descriptor technique known in the field of computer vision are suitable for use in this method.

At 1724, in some embodiments, identified interest point/s and descriptor/s are transmitted.

In some embodiments, steps 1722-1724 are performed by a processor within the add-on.

In some embodiments, transfer of step 1724 is performed by a low bandwidth link.

Where, in some embodiments, transfer is between an add-on processor and a smartphone processor.

At 1725, in some embodiments, interest points and/or descriptors are received, for example, by a smartphone processor.

At 1726, in some embodiments, camera positon is determined, based on interest point/s and/or descriptors. For example, where, based on a position in an image of an interest point and/or descriptor, the imager position is determined.

At 1727, in some embodiments, for example, using additional data (e.g. previously generated model, e.g. one or more acquired image) a model of one or more tooth, for example, a 3D model of one or more tooth is constructed using interest point/s and/or descriptors and/or determined camera position/s.

Exemplary Calibration

FIG. 18A is a simplified schematic of a calibration cradle 1800 holding an add-on 1801 connected to a smartphone 1802, according to some embodiments of the invention.

In some embodiments, calibration cradle 1800 is sized and/or shaped to connect and/or hold one or both of smartphone 1802 and add-on 1801. For example, in some embodiments, a body 1803 of calibration cradle 1800 includes an indentation 1807 in body 1803 sized and/or shaped to hold smartphone 1802 and/or add-on 1801.

In some embodiments, calibration cradle includes one or more calibration target 1804. In some embodiments, calibration targets 1804 are positioned in known positions relative to the cradle body 1803. For example, where, in some embodiments, cradle body 1803 includes rigid portions and/or where targets 1804 are rigidly attached to cradle 1803. In some embodiments, position of targets 1804 is known with respect to one or more part mechanically connected to the cradle. For example, with respect to one or more portion of smartphone 1802 and/or or add-on 1801 e.g. with respect to imaging FOV 1806. Where, in some embodiments, (e.g. according to one or more feature of one or more embodiment as described elsewhere in this document) illumination FOV 1805 and/or imaging FOV 1806 is transferred through add-on 1801 from an illuminator and/or imager of smartphone 1802.

In some embodiments, during calibration (which, for example, includes one or more feature as illustrated in and/or described regarding step 2108 FIG. 21) calibration target/s 1804 are imaged using imaging FOV 1806 to calibrate one or more feature e.g. one or more of size and/or distance and/or position and/or color of feature/s of images collected using the add-on and/or a position of the add-on with respect to the smartphone. Where, in some embodiments, imaged targets are scanned and one or more feature determined from the images is compared to known feature/s of the calibration cradle. In some embodiments, determined differences between the features is used to determine measurement/s e.g. of dental features e.g. imaged using smartphone 1802 and add-on 1801.

FIG. 18B is a simplified schematic of an add-on 1801 attached to a smartphone 1802, according to some embodiments of the invention.

Additionally or alternatively to using a calibration cradle, in some embodiments, add-on 1801 includes one or more integral calibration element 1815A-B.

In some embodiments, add-on 1801 includes a calibration cover 1815A, 1815B. In some embodiments, the cover is a moveable cover where, in some embodiments, the cover is configured to be moved from a covering position 1815B to a retracted position 1815A. In some embodiments, in covering position 1815B, the cover intercepts one or more FOV emanating from add-on 1801. In some embodiments, the cover has one or more calibration target which are imaged using the FOVs, images used to calibrate images acquired using the add-on and/or smartphone. Where, in some embodiments, smartphone 1802 includes one or more imager 1818 and/or one or more illuminator 1817 where FOVs of the imager and/or illuminator are transferred through add-on 1801 and exit the add-on at a region of the add-on which is intercepted (e.g. at least partially covered) by the cover when it is in position 1815B.

In some embodiments, the cover is attached to add-on 1801 and then removed e.g. after calibration using the cover for example, instead of sliding the cover into position 1815. Where, for example, connector/s of the cover and/or add-on are used to attach the cover.

In some embodiments, the cover slides e.g. on one or more rail of a body of add-on 1801. In some embodiments, when scanning is performed, the cover is retracted.

Alternatively or additionally to a moveable cover, in some embodiments, a calibration element obscures a portion of the FOV/s emanating from add-on 1801 e.g. even during scanning.

In some embodiments, for example, in addition or alternatively to other calibration techniques described in this document, one or more optical element of add-on 1801 is used in calibration. For example, in some embodiments, a mirror 1819 is used in calibration. In some embodiments, mirror edges are extracted from collected images, to determine alignment of add-on 1801 with respect to smartphone 1802 and/or smartphone imager 1818.

In some embodiments, for example, in addition or alternatively to other calibration techniques described in this document, an inner portion of the add-on body (also termed "sleeve") is used in calibration. For example, is marked with one or more calibration target and/or fiducial. Where image/s including the feature/s of the inner portion and/or target/s and/or fiducial/s of the inner portion acquired by smartphone camera 1818 are, in some embodiments, used for calibration.

In some embodiments, a calibration element which remains in a FOV (e.g. a cover continuing to partially interrupt a FOV e.g. calibration using internal feature/s of the add-on) potentially enables repeated and/or continuous and/or during scanning calibration of images. For example, calibration to remove error/s and/or influence of add-on movement with respect to the smartphone e.g. during scanning.

Exemplary Scanning Aids

FIG. 22 is a simplified schematic illustrating scanning of a subject 2256 using an add-on 2204 attached to a smartphone 2206, according to some embodiments of the invention.

In some embodiments, for example, prior to scanning, one or more mirror 2270 is positioned. In some embodiments, mirror/s are positioned by positioning a cheek retractor to which the mirror/s are coupled and/or attached. For example, within a subject's mouth. In some embodiments, mirror reflects view/s of dental feature/s for example, enabling imaging of the feature/s using add-on 2204. For example, as illustrated in FIG. 22 where mirror 2270 provides an image of distal side/s of a tooth/teeth on the lower jaw which, in some embodiments, are imaged using FOV 2272. Where, in some embodiments, FOV 2272 emanates from add-on 2204 (and/or directly from smartphone 2201).

In some embodiments, additionally or alternatively to allowing imaging of dental surface/s, in some embodiments, one or more mirror is used to deliver projected light to one or more dental surface.

Figure 19A:
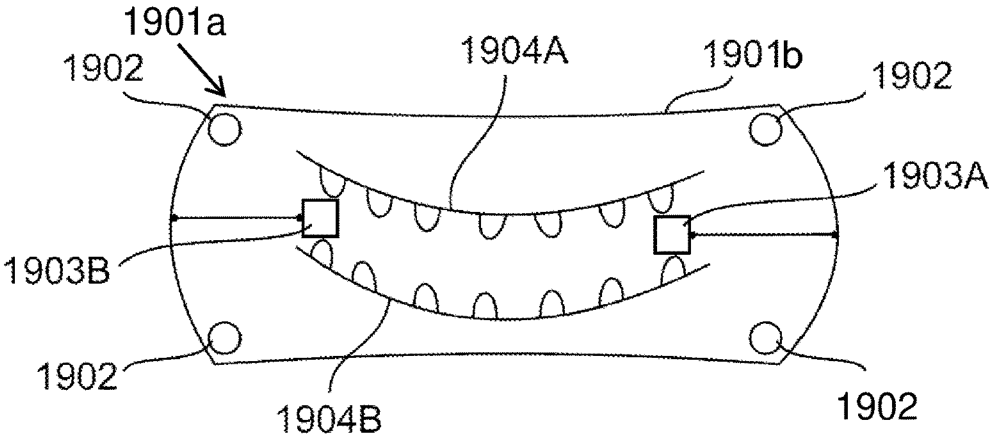
FIG. 19A is a simplified schematic of a cheek retractor, according to some embodiments of the invention.
Figure 19B:
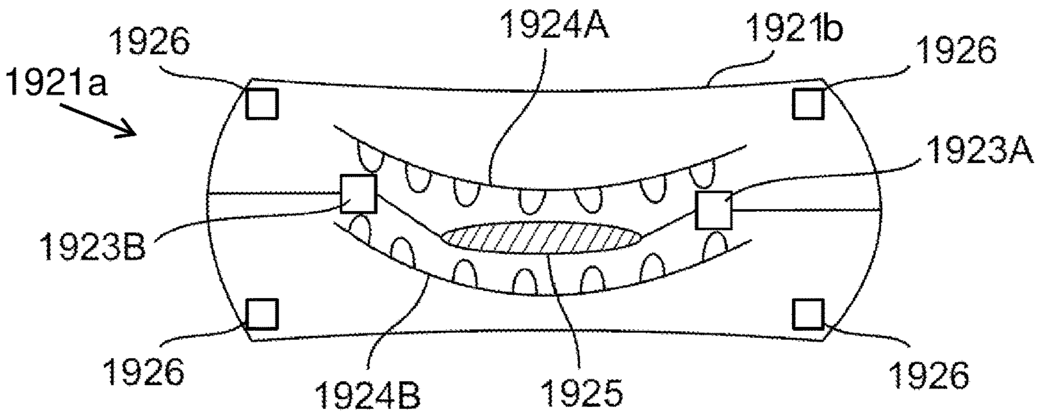
FIG. 19B is a simplified schematic of a cheek retractor, according to some embodiments of the invention.
Figure 19C:
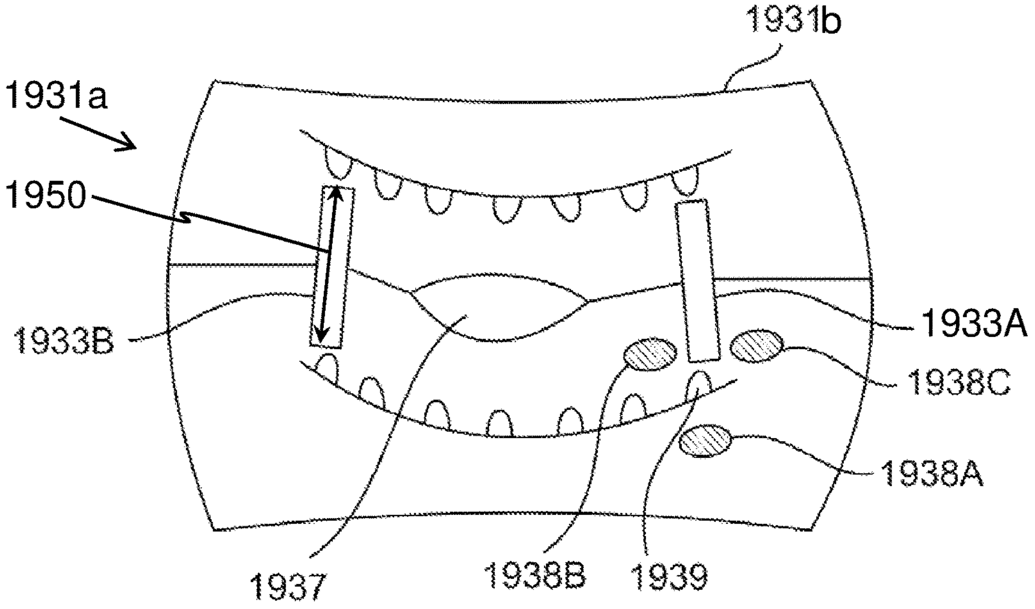
FIG. 19C is a simplified schematic of a cheek retractor, according to some embodiments of the invention.

In some embodiments, exemplary mirror positions include one or more of feature as illustrated and/or described regarding mirrors 1938A, 1938B, 1938C FIG. 19C.

In some embodiments, for example, prior to scanning, one or more fiducial 2250, 2264 is attached to one or more portion of a subject 2256. For example, to a subject tooth 2254 e.g. fiducial 2250. For example, outside subject's 2256 mouth e.g. fiducial 2264.

In some embodiments, fiducial/s provide known spatial reference/s e.g. with respect to other teeth and/or the jaw and/or for combining of multiple images (e.g. collected at the same time or during different scans), and/or known size in one or more dimension and/or known color (e.g. for calibration of tooth color).

In some embodiments, fiducial 2250 remains in situ e.g. is glued onto tooth 2254. In some embodiments, fiducial 2250 is hosted by a holder which is removable e.g. to be positioned before scanning and removed afterwards. In some embodiments, the holder is sized and/or shaped to fit a particular dental structure (e.g. tooth) potentially enabling a user to position the fiducial 2250 in a same place for scanning at different times. In some embodiments, a fiducial 2264 disposed outside a subject's mouth is attached to the subject by attachment and/or coupling to inside the subject's mouth (e.g. by a cheek retractor).

A potential advantage of attachment to a tooth 2250 (or other rigid dental structure e.g. prosthetic) is a fixed spatial relationship between the fiducial and dental structure/s e.g. teeth of the same jaw as the fiducial. In some embodiments, one or more image collected using add-on 2204 and smartphone 2201 includes at least a portion of fiducial 2250. Where, in some embodiments, the fiducial is used in calibration of the image/s and/or in stitching of multiple images e.g. to construct a model.

In some embodiments, fiducial/s 2250 are captured using a same FOV 2268 as captures dental feature/s. Alternatively, or additionally, fiducial/s 2264 are captured by additional FOV/s 2266. In some embodiments, fiducial/s 2264 are captured directly by smartphone imager/s, additionally or alternatively to capture by FOV/s emanating from add-on 2204.

FIG. 23 is a simplified schematic illustrating scanning of a subject 2356 using an add-on 2304 attached to a smartphone 2306, according to some embodiments of the invention.

In some embodiments, a fiducial 2350 is used e.g. including one or more feature as described regarding fiducial 2250 FIG. 22. In some embodiments, fiducial 2350 is attached by a user biting down on a holder 2358. I Where, in some embodiments, holder 2358 hosts one or more fiducial 2350. In some embodiments, holder 2358 is sized and/or shaped to fit one or more teeth, for example, one or both of opposing teeth 2362, 2360. In some embodiments, holder 2358 is designed to be relocatable to a same position within a mouth. For example, where shaping and/or sizing of the holder assists a user in positioning the holder (and fiducial 2350) in a same position relative to dental feature/s to be scanned.

Exemplary Cheek Retractor

FIG. 19A is a simplified schematic of a cheek retractor 1901*a*, according to some embodiments of the invention.

In some embodiments, for example, as described in step 2110 and/or step 2112 FIG. 21, cheek retractor 1901*a* is used while scanning the teeth inside the mouth using an add-ons where the add-on, in some embodiments, is connected to a smartphone (add-on e.g. as described elsewhere in this document).

A potential advantage of using a cheek retractor during scanning is revealing of outer surfaces of teeth for imaging.

In some embodiments, cheek retractor 1901*a* is held in position with respect to dental feature/s e.g. jaws 1904A, 1904B and/or teeth. In some embodiments, cheek retractor 1901*a* is held in position by a user biting down on one or more biting elements 1903A and 1903B. For example, a first 1903A and a second 1903B biting element. Where, in some embodiments, one or more biting element is located at a distal end of a jaw e.g. held in position by closure of molars around the biting element.

In an exemplary embodiment, biting elements 1903A, 1903B move with movement of cheek retractor 1901*a*, for example, are rigidly attached to a body 1901*b* of cheek retractor 1901*a*.

In some embodiments, cheek retractor 1901 includes one or more fiducial 1902. Where, for example, in some embodiments, the subject bites down on biting elements 1903A, 1903B e.g. to hold fiducials 1902 in known position/s relative to dental feature/s. Where, in some embodiments, one or both of biting elements 1903A, 1903B include one or more feature as illustrated in and/or described regarding holder 2358 FIG. 23. In some embodiments, capture of image/s including fiducial/s 1902 includes one or more feature as described regarding capture of fiducial 2264 FIG. 22.

FIG. 19B is a simplified schematic of a cheek retractor 1921*a*, according to some embodiments of the invention.

In some embodiments, cheek retractor 1921*a* includes one or more mirror 1925. In some embodiments, mirror 1925 is attached to a body 1921*b* of cheek retractor 1921*a*.

In some embodiments, mirror 1925 is a curved mirror. In some embodiments, mirror 1925 is held in a fixed position with respect to dental feature/s e.g. with respect to jaws 1924A and 1924B, for example, by biting elements 1923A and 1923B. Where, in some embodiments, biting elements 1923A, 1923B are attached to body 1921*b* (e.g. rigidly). In some embodiments, cheek retractor 1921*a* includes one or more fiducial and/or color reference 1926.

In some embodiments, mirror 1925 reflects view/s of lingual parts of the teeth. Potentially enabling collection of images including both external tooth surfaces and/or lingual and/or buccal (e.g. reflected) sides of teeth at the same time and/or for a same position of the add-on and/or smartphone and/or using the same FOV.

FIG. 19C is a simplified schematic of a cheek retractor 1931, according to some embodiments of the invention.

Optionally, in some embodiments, cheek retractor 1931 (and/or any of cheek retractors 1901*a* FIG. 19A, 1921*a* FIG. 19B, 1990 FIG. 19D) includes a tongue retractor 1937.

In some embodiments, cheek retractor 1931 (and/or any of cheek retractors 1901*a* FIG. 19A, 1921*a* FIG. 19B, 1990 FIG. 19D) includes one or more mirror which, when the cheek retractor is in position, a mirror 1938B is positioned on a lingual side of teeth (e.g. of a jaw) and/or a mirror 1938A which is positioned on a buccal side of teeth (e.g. of a jaw) and/or a mirror 1938C which is positioned distal of a final tooth 1939 of a jaw.

In some embodiments, one or more mirror enables scanning and/or light projection onto one or more dental feature surface e.g. one or more lingual and/or buccal and/or distal dental surface (e.g. surface of a tooth and/or dental prosthetic).

In some embodiments, biting elements 1933A, 1933B are sized to hold the jaws apart. For example, to allow insertion into the mouth of an add-on and/or smartphone e.g. while maintaining the cheek retractor in position. In some embodiments, a height 1950 of one or more biting element 1933A, 1933B is 5-50 mm, or 20-30 mm, or about 10 mm or about 20 mm or about 30 mm or lower or higher or intermediate heights or ranges. Potentially such height biting elements hold the jaws open e.g. to a known distance, where, in some embodiments, the known distance is used in image processing e.g. generating of model/s.

Figure 19D:
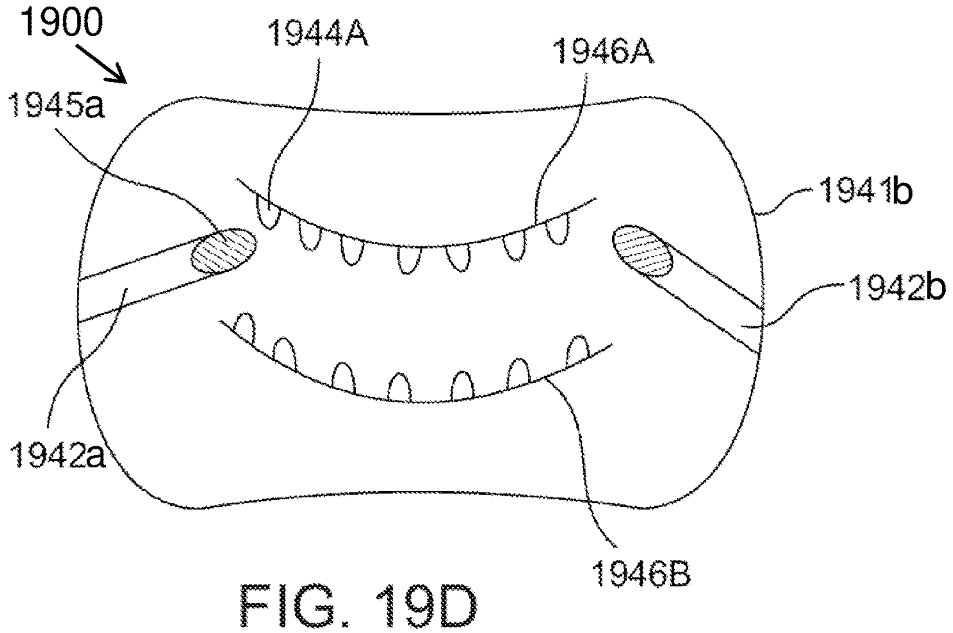
FIG. 19D is a simplified schematic front view of a cheek retractor, according to some embodiments of the invention.

FIG. 19D is a simplified schematic front view of a cheek retractor, according to some embodiments of the invention.

showing the back-side parts of the cheek retractor with attached mirrors.

Figure 19E:
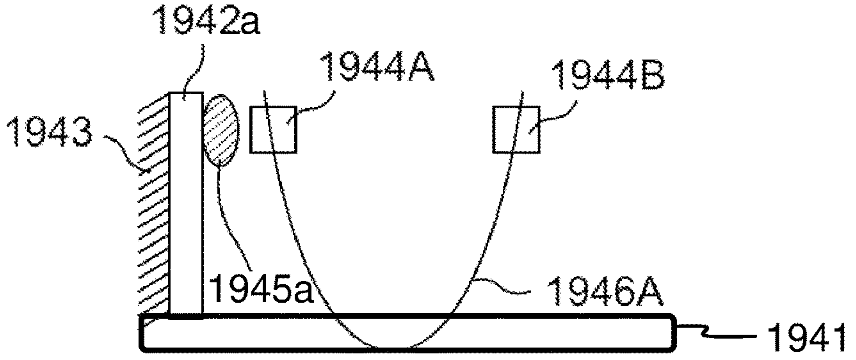
FIG. 19E is a simplified schematic top view of a single back side cheek retractor within a mouth, according to some embodiments of the invention.

FIG. 19E is a simplified schematic top view of a single back side cheek retractor 1942*a* within a mouth, according to some embodiments of the invention.

moving the cheek 1943 away from the distal teeth 1944A and allowing the smartphone to capture an image of the buccal part of the teeth.

Figure 19F:
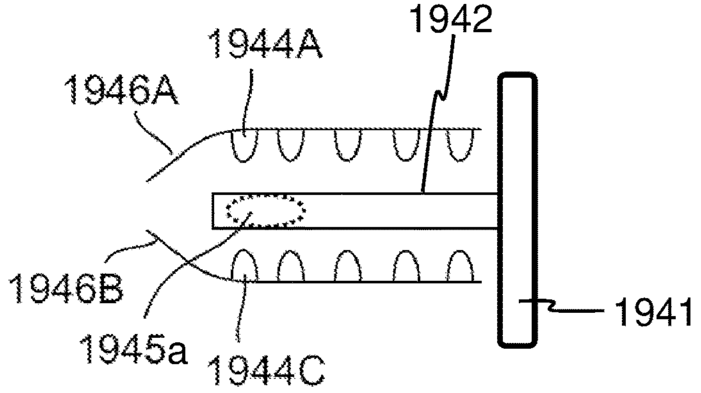
FIG. 19F is a simplified schematic cross section of a backside cheek retractor, within a mouth, according to some embodiments of the invention.

FIG. 19F is a simplified schematic cross section of a backside cheek retractor 1942*a*, within a mouth, according to some embodiments of the invention.

In some embodiments, FIG. 19F shows a side view while the jaws are a little open, (e.g.

optionally held open by a biting element/s). In some embodiments, and mirror/s 1945*a* are tilted e.g. in a superior or inferior direction, in order to capture the upper or lower jaw and/or mirror/s are curved.

FIG. 19D, FIG. 19E, and FIG. 19F, in some embodiments, illustrate the same cheek retractor 1940.

In some embodiments, cheek retractor 1940 includes one or more feature as illustrated in and/or described regarding cheek retractor 1902 FIG. 19A and/or cheek retractor 1921 FIG. 19B and/or cheek retractor 1931 FIG. 19C.

In some embodiments, cheek retractor 1940 includes one or more back-side cheek retractor 1942*a*, 1942*b*. In some embodiments, back-side cheek retractor/s 1942*a*, 1942*b* are optionally elongate elements which are connected to a body 1941 of cheek retractor 1940, and extend into a subject's mouth e.g. when cheek retractor 1942 is in position. In an exemplary embodiment, cheek retractor 1940 includes two back-side cheek retractors 1942*a*, 1942*b*, each one configured to retract a back side of a different cheek e.g. away from distal teeth 1944A e.g. molars, of a subject.

In some embodiments, one or both of back-side cheek retractors 1942*a*, 1942*b* include a mirror 1945*a*, 1945*b*. Where, in some embodiments, mirror/s 1945*a*, 1945*b* are disposed (e.g. attached to) a distal part of back-side cheek retractors 1942*a* 1942*b*. In some embodiments, mirror/s 1945*a*, 1945*b* enable capture of image/s of a buccal side of the teeth 1944A (e.g. refer to FIG. 19D and/or FIG. 19E) adjacent to the back-side cheek retractor side and/or lingual side of the distal teeth 1944B (e.g. refer to FIG. 19E) on an opposite region of the jaw and/or mouth e.g. opposite to a location of a distal portion of back-side cheek retractor 1942*a*.

In some embodiments, mirror 1945*a* includes different portion/s (or includes two mirrors) at different angles, for example, a first portion of mirror 1945*a* tilted in a superior direction e.g. to reflect an image of a tooth (e.g. a distal tooth) 1944A in the upper jaw and a second portion of mirror 1945*a* is tilted in an inferior direction e.g. to reflect an image of a tooth (e.g. a distal tooth) 1944C in the lower jaw.

Figure 19G:
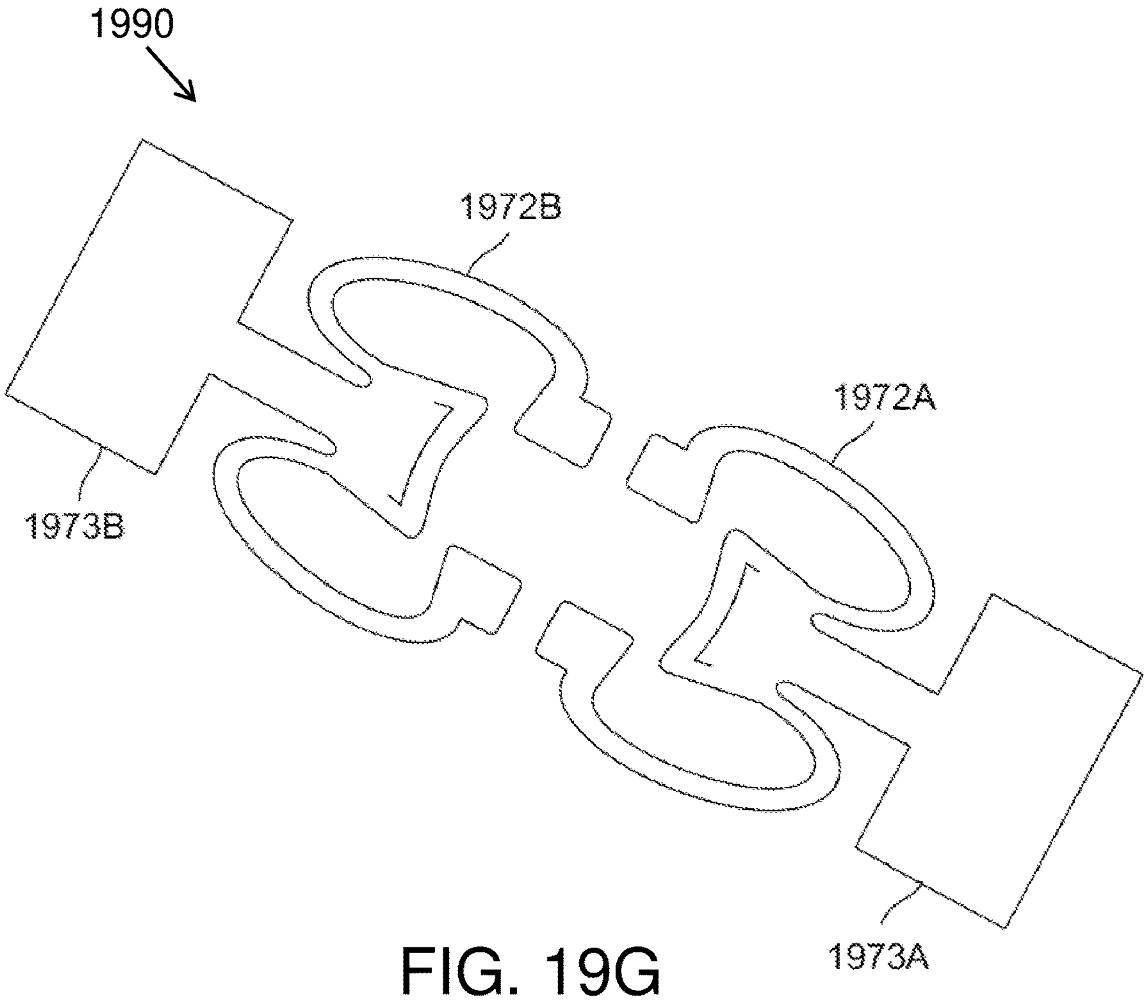
FIG. 19G is a simplified schematic of a cheek retractor, according to some embodiments of the invention.

FIG. 19G is a simplified schematic of a cheek retractor 1990, according to some embodiments of the invention.

Figure 19H:
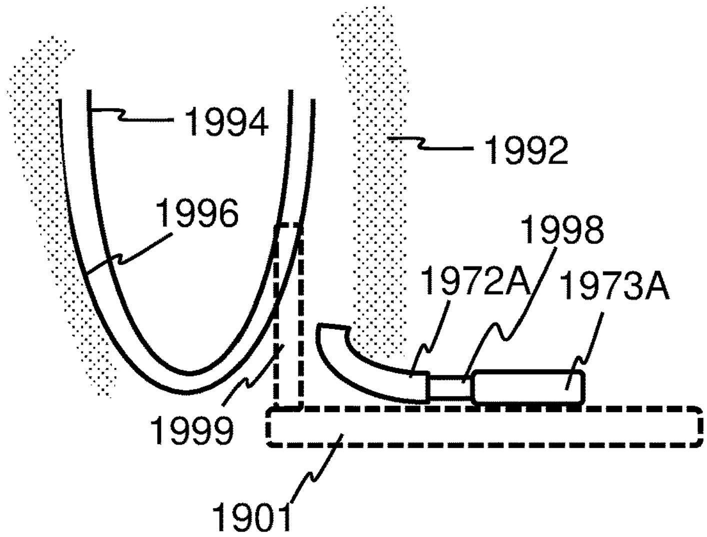
FIG. 19H is a simplified schematic of a cheek retractor, according to some embodiments of the invention.

FIG. 19H is a simplified schematic of a cheek retractor 1972A, according to some embodiments of the invention.

In some embodiments, cheek retractor 1990 includes one or more feature as illustrated in and/or described regarding cheek retractor 1902 FIG. 19A and/or cheek retractor 1921 FIG. 19B and/or cheek retractor 1931 FIG. 19C and/or cheek retractor 1940 FIGS. 19D-F.

In some embodiments, cheek retractor 1990 includes two portions (also herein termed "sides") 1972A and 1972B.

Where, in some embodiments, portions 1972A and 1972B are separate and not connected. In some embodiments, each side 1972A, 1972B moves separately from the other side. In some embodiments, each side is used to retract one cheek.

In some embodiments, one or both portions of retractor 1990 include a smartphone cradle 1973A, 1973B. Where, in some embodiments, the cradle allows movement of the portion 1972A of the retractor, while holding the smartphone e.g. as illustrated in FIG. 19H.

FIG. 19H, in some embodiments, illustrates use of a single side of the cheek retractor 1990.

In some embodiments, cheek tissue 1992 is held away from jaw/s 1994, 1996. Where, in some embodiments, a first portion 1972 holds cheek tissue 1992 and phone cradle 1973 is attached to first portion 1972 by a connecting portion 1998.

In some embodiments, a user holds cheek 1992 in a retracted position by applying pressure to cradle 1973A e.g. via pressure applied to smartphone 1901.

In some embodiments, a two part cheek retractor (and/or a single cheek retractor where sides are flexibly and/or elastically connected) enables adaptive opening of the mouth according to a position of the smartphone potentially increasing a size of opening to the teeth e.g. increasing speed of imaging.

In some embodiments, cheek retractor 1990 is used with an add-on 1999. Where add-on includes one or more features of add-ons described and/or illustrated elsewhere in this document.

Exemplary Monitoring

Figure 20:
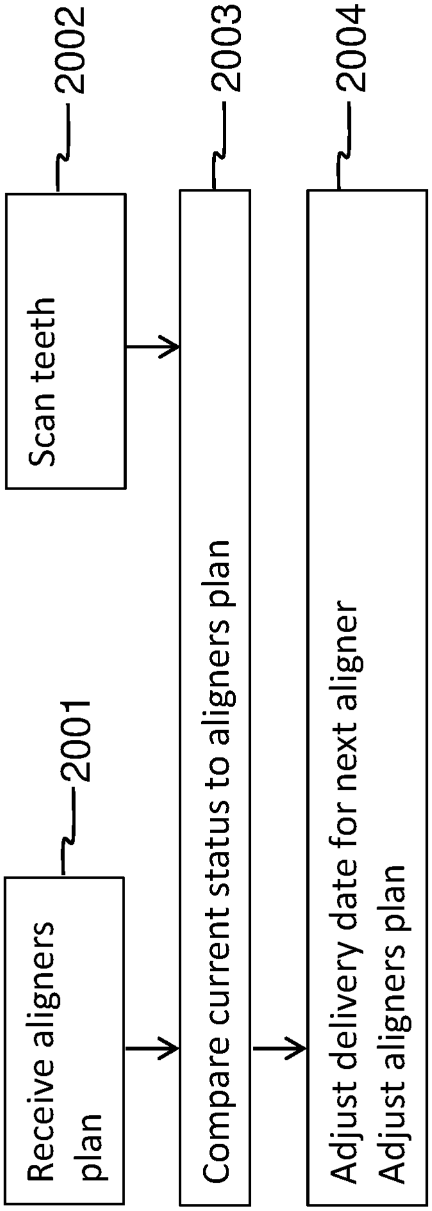
FIG. 20 is a flow chart of a method of monitoring teeth alignment, according to some embodiments of the invention.

FIG. 20 is a flow chart of a method of monitoring teeth alignment, according to some embodiments of the invention.

At 2001, in some embodiments, an alignment plan is received. For example, a plan associated with an alignment tool e.g. transparent aligners. In some embodiments, the user is treated by wearing aligners. Where, in some embodiments, as the teeth move, the user moves from using an initial set to using a subsequent set of aligners, where, in some embodiments, there are 1-5 sets of aligners. of aligners and replaces them with a new set of aligners.

At 2002, in some embodiments, teeth are scanned e.g. by a user, for example, using an add-on attached to the user's smartphone.

At 2003, in some embodiments, a position of teeth measured by scanning of step 2002 is compared with the alignment plan. Where, in some embodiments, the alignment plan includes plan models e.g. for each aligner.

In some embodiments, it is confirmed that the position of the teeth is between a first aligner start position and a second aligner start position.

At 2004, in some embodiments, new aligners delivery date and/or a design of a future set of aligners is determined based on the scanned position of the teeth (e.g. at step 2003).

For example, if scans indicate that the teeth have moved faster than initially expected, a future set of aligners will arrive earlier than an initial plan. Scanning potentially reducing a time taken to align teeth.

For example, if scans indicate that the teeth are moving slower than initially expected delay in use of a future set of aligners and/or change in design of a future set of aligners potentially reduce pain of treatment and/or damage to the teeth.

General

It is expected that during the life of a patent maturing from this application many relevant dental measurement and/or scanning technologies will be developed and the scope of the terms measurements and scanning are intended to include all such new technologies a priori.

As used herein the term "about" refers to ±20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A dental add-on for an electronic communication device having a screen and at least one optical element, said dental add-on comprising:

a. a body comprising:

i. a distal portion sized and shaped to be at least partially inserted into a human mouth within, in one or more dimension, one or both dental arches;

ii. at least one first optical path extending from said at least one optical element of said electronic communication device, through said body to said distal portion and configured to adapt a FOV of said at least one optical element for dental imaging; and iii. a connector for connection of said dental add-on body to said electronic communication device, wherein said dental add-on includes a patterning element disposed within a second optical path; said second optical path extending between one or more illuminators of said electronic communication device and said FOV of said at least one optical element.

2. The dental add-on according to claim 1, wherein said at least one optical element comprises an imager.

3. The dental add-on according to claim 1, wherein said at least one first optical path adapts said FOV for dental imaging by directing said FOV into said human mouth.

4. The dental add-on according to claim 1, wherein said at least one first optical path transfers a FOV including a view of at least a portion of said human mouth to said imager.

5. The dental add-on according to claim 1, wherein:

said screen is disposed on a front face of said electronic communication device, said imager is disposed on a back face of said electronic communication device, and when said body is connected to said electronic communication device, said at least one first optical path extends in a direction generally parallel to one or both of an orientation of said front face and an orientation of said back face.

6. The dental add-on according to claim 1, wherein said dental add-on comprises an add-on illuminator, where a FOV of said illuminator overlaps with said imaging FOV.

7. The dental add-on according to claim 6, wherein said dental add-on illuminator is powered by an add-on power source.

8. The dental add-on according to claim 6, wherein said dental add-on illuminator is powered by said electronic communication device.

9. The dental add-on according to claim 1, wherein said dental add-on comprises a pattern projector.

10. The dental add-on according to claim 9, wherein said pattern projector comprises said one or more dental add-on illuminator.

11. The dental add-on according to claim 1, wherein said at least one first optical path includes one or more optical path element which changes optical power of light received by said optical path element to focus light within said at least one first optical path.

12. The dental add-on according to claim 11, wherein said one or more optical path elements are selected from the group consisting of: a curved mirror, lens, prism, and any combination of the forgoing.

13. The dental add-on according to claim 1, wherein said at least one first optical path includes one or more mirror changing a direction of said optical path.

14. The dental add-on according to claim 1, wherein said connector is configured to align said at least one first optical path with said imager of said electronic communication device.

15. The dental add-on according to claim 14, wherein a position of said connector is adjustable with respect to said body.

16. The dental add-on according to claim 1, when said dental add-on body is elongate.

17. The dental add-on according to claim 1, wherein a ratio of a length of said body measured along a longitudinal axis is at least 2 times a maximum transverse dimension of said body taken perpendicular to said longitudinal axis.

18. The dental add-on according to claim 1, wherein said one or more illuminators illuminates with near infrared light (NIR).

19. The dental add-on according to claim 1, wherein said patterning element comprises one or more lens disposed within said second optical path.

20. The dental add-on according to claim 1, wherein said one or more illuminators of said electronic communication device are configured to illuminate UV light and/or 300 nm-440 nm light; and wherein said dental add-on is configured to be used for performing fluorescence measurements.

21. The dental add-on according to claim 6, wherein said add-on illuminator is configured to illuminate UV light and/or 300 nm-440 nm light; and wherein said dental add-on is configured to be used for performing fluorescence measurements.

22. The dental add-on according to claim 1, further comprising one or more filters, comprising one or more of:

a. a first filter positioned on said first optical path and configured for removing light of wavelengths projected by said one or more illuminators of said electronic communication device;

b. a second filter positioned on said second optical path and configured for filtering a light emitted by said one or more illuminators of said electronic communication device to allow emission of only one or more desired wavelengths through said second optical path.

23. A method of intraoral imaging comprising:

aligning at least one optical element of an electronic communication device to one or more optical paths of an add-on to transfer a FOV of said at least one optical element into said one or more add-on optical paths;

attaching said add-on to said electronic communication device; and positioning said FOV of said at least one optical element within a mouth, by positioning at least a portion of said add-on within said mouth, wherein said method comprises adding a patterning element to a second optical path; said second optical path extending between one or more illuminators of said electronic communication device and said FOV of said at least one optical element.

24. The method according to claim 23, wherein said method comprises acquiring one or more image of a dental feature using said at least one optical element.

* * * * *